US006288088B1

(12) United States Patent
Kando et al.

(10) Patent No.: US 6,288,088 B1
(45) Date of Patent: Sep. 11, 2001

(54) OXADIAZOLINE DERIVATIVE AND THEIR USE AS INSECTICIDES

(75) Inventors: Yasuyuki Kando; Makota Noguchi; Akayama Atsuo; Shinichi Masada; Toshiyuki Kiji, all of Tsukuba (JP)

(73) Assignee: Takeda Chemical Industries, Ltd., Osaka-Fu (JP)

( * ) Notice: Subject to any disclaimer, the term of this patent is extended or adjusted under 35 U.S.C. 154(b) by 0 days.

(21) Appl. No.: 09/701,544

(22) PCT Filed: May 31, 1999

(86) PCT No.: PCT/JP99/02876

§ 371 Date: Nov. 30, 2000

§ 102(e) Date: Nov. 30, 2000

(87) PCT Pub. No.: WO99/62903

PCT Pub. Date: Dec. 9, 1999

(30) Foreign Application Priority Data

Jun. 2, 1998 (JP) .................................. 10-153166
Aug. 20, 1998 (JP) .................................. 10-234733
Apr. 1, 1999 (JP) .................................. 11-095559

(51) Int. Cl.[7] .................... A61K 31/4245; C07D 413/04; C07D 271/06

(52) U.S. Cl. ...................... 514/340; 546/269.1; 548/131; 514/364

(58) Field of Search .................. 548/131; 546/269.1; 514/364, 340

(56) References Cited

U.S. PATENT DOCUMENTS

| | | | |
|---|---|---|---|
| 5,124,341 | * 6/1992 | Tomioka et al. | 514/364 |
| 5,556,867 | * 9/1996 | Hirose et al. | 514/340 |
| 6,194,441 | * 2/2000 | Roberts et al. | 514/340 |

FOREIGN PATENT DOCUMENTS

| | | |
|---|---|---|
| 0 911 329 | 4/1999 | (EP) . |
| 97 28126 | 8/1997 | (WO) . |
| WO-97/28126 | * 8/1997 | (WO) . |

* cited by examiner

Primary Examiner—Deborah C. Lambkin
Assistant Examiner—Golam M. M. Shameem
(74) Attorney, Agent, or Firm—Wenderoth, Lind & Ponack, L.L.P.

(57) ABSTRACT

The present invention relates to a compound of the formula [I]:

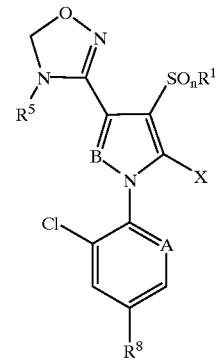

wherein $R^1$ is $C_{1-6}$ alkyl or $C_{1-6}$ haloalkyl; n is 0, 1 or 2; X is (1) group of $-NR^2R^3$ wherein $R^2$ and $R^3$ independently represent (i) hydrogen or (ii) $C_{1-6}$ alkyl which may optionally be substituted with pyridyl, (2) group of $-N=CHOR^4$ wherein $R^4$ represents $C_{1-6}$ alkyl, (3) group of $-N=CHNR^6R^7$ wherein $R^6$ and $R^7$ independently represent (i) hydrogen or (ii) $C_{1-6}$ alkyl, (4) group of $-N=CHAr$ wherein Ar represents phenyl which may optionally be substituted with substituents selected from the group consisting of hydroxy and $C_{1-3}$ alkoxy, or (5) pyrrolyl; $R^5$ is optionally substituted alkyl or optionally substituted acyl; $R^8$ is (1) halogen, (2) $C_{1-6}$ haloalkyl, (3) $C_{1-6}$ haloalkoxy or (4) phenyl which may optionally be substituted with $C_{1-6}$ haloalkyl;

A is (1) nitrogen atom or (2) group of

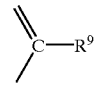

wherein $R^9$ is chlorine atom or cyano; and B is nitrogen atom or

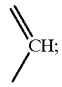

or a salt thereof.

The compounds [I] or their salts have excellent insecticidal activities and less toxicity against fishes. Therefore, the agrochemical compositions containing the compound [I] or a salt thereof can protect crops, etc. from harmful pests so as to contribute to an agricultural success.

19 Claims, No Drawings

OXADIAZOLINE DERIVATIVE AND THEIR USE AS INSECTICIDES

This application is a 371 of PCT/JP99/02876 filed May 31, 1999.

TECHNICAL FIELD

The present invention relates to a novel oxadiazoline derivative and agrochemical composition comprising it.

BACKGROUND ART

A large number of synthetic compounds having pest-controlling activities have so far been used as insecticides. Most of them, however, belong to the family of organic phosphoric acid esters, carbamic acid esters, organic chlorine-containing compounds or pyrethroid compounds.

On the other hand, it isreportedthat 1-arylpyrazole derivatives having a hydrogen or halogen atom or an alkyl, cycloalkyl, haloalkyl, cyano, nitro, carbamoyl or thiocarbamoyl group at position 3 of the pyrazole ring exhibit insecticidal activity [JP-A-228065/1987, 207259/1987, 148240/1993, 282366/1990, 86054/1993, and JP-A-500319/1995, etc.].

However, while these pyrazole derivatives are high in insecticidal activity, they show high toxicity to man, animals and fish. In some cases, they show toxicity even in natural enemies to pests. Moreover, these compounds tend to remain in soil to a considerable extent. For these and other reasons, satisfactory effects are not always obtained under the existing circumstances.

DISCLOSURE OF INVENTION

The present inventors have long been engaged in intensive investigations in an attempt to discover insecticides quite different in structure from the insecticides that have so far been used. As a result, they unexpectedly found that novel oxadiazolinylpyrazole derivatives represented by the formula [I], inclusive of salts thereof, have very strong insecticidal activity. It was further found that they have little phytotoxicity, are low in toxicity and safe to humans and animals, to fish and to natural enemies to pests, among others. Based on these findings, the present inventors have continued their research, and have now completed the present invention.

Namely, the present invention relates to: [1] a compound represented by the formula [I]:

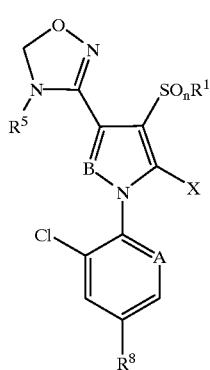

[I]

wherein $R^1$ is a $C_{1-6}$ alkyl group or a $C_{1-6}$ haloalkyl group; n is 0, 1 or 2;

X is (1) a group of $—NR^2R^3$ wherein $R^2$ and $R^3$ independently represent (i) a hydrogen atom or (ii) a $C_{1-6}$ alkyl group which may optionally be substituted with pyridyl group,
(2) a group of $—N{=}CHOR^4$ wherein $R^4$ represents a $C_{1-6}$ alkyl group,
(3) a group of $—N{=}CHNR^5R^7$ wherein $R^6$ and $R^7$ independently represent (i) a hydrogen atom or (ii) a $C_{1-6}$ alkyl group,
(4) a group of $—N{=}CHAr$ wherein Ar represents a phenyl group which may optionally be substituted with a substituent or substituents selected from the group consisting of hydroxy and $C_{1-3}$ alkoxy groups, or
(5) a pyrrolyl group;
$R^5$ is an optionally substituted alkyl group or an optionally substituted acyl group;
$R^8$ is (1) a halogen atom, (2) a $C_{1-6}$ haloalkyl group, (3) a $C_{1-6}$ haloalkoxy group or (4) phenyl which may optionally be substituted with a $C_{1-6}$ haloalkyl group;
A is (1) a nitrogen atom or (2) a group of

wherein $R^9$ is a chlorine atom or cyano; and
B is a nitrogen atom or

(hereinafter sometimes referred to as "Compound [I]"); or a salt thereof,
[2] the compound as described in above [1], wherein $R^1$ is a trifluoromethyl group, or a salt thereof,
[3] the compound as described in above [1], wherein X is (1) a group of $—NR^2R^3$ wherein $R^2$ and $R^3$ independently represent (i) a hydrogen atom or (ii) a $C_{1-6}$ alkyl group, or (2) a group of $—N{=}CHOR^4$ wherein $R^4$ represents a $C_{1-6}$ alkyl group, or a salt thereof,
[4] the compound as described in above [1], wherein X is $—NH_2$ or a group of $—N{=}CHOR^4$ wherein $R^4$ represents a $C_{1-6}$ alkyl group, or a salt thereof,
[5] the compound as described in above [1], wherein $R^5$ is an optionally substituted carbamoyl group, or a salt thereof,
[6] the compound as described in above [1], wherein $R^5$ is (1) a $C_{1-6}$ alkyl group which may optionally be substituted with one to three $C_{1-6}$ alkoxy groups, (2) a $C_{2-10}$ alkanoyl group which may optionally be substituted with one to three substituents selected from the group consisting of (i) amino which may optionally be substituted with one or two $C_{1-6}$ alkyl groups, (ii) a $C_{1-6}$ alkoxy group, (iii) phenyl and (iv) a halogen atom, (3) a $C_{4-10}$ cycloalkanoyl group, (4) a $C_{3-10}$ alkenylcarbonyl group, (5) benzoyl, (6) carbamoyl which may optionally be substituted with one or two substituents selected from the group consisting of (i) a $C_{1-6}$ alkyl group which may optionally be substituted with the substituents selected from the group consisting of phenyl, halogen and amino which may optionally be substituted with $C_{1-6}$ alkyl, (ii) a $C_{3-9}$ cycloalkyl group, (iii) a $C_{2-6}$ alkenyl group, (iv) a $C_{2-6}$ alkynyl group, (v) phenyl, (vi) amino which may optionally be substituted with one or two $C_{1-6}$ alkyl groups, (vii) a cyclic amino group, (viii) hydroxy and (ix) a $C_{1-6}$ alkoxy group, (7) a cyclic amino-carbonyl group, or (8) a $C_{1-6}$ alkoxy-carbonyl group or (9) formyl, or a salt thereof,

[7] the compound as described in above [1], wherein $R^8$ is a trifluoromethyl group, or a salt thereof,

[8] the compound as described in above [1], wherein A is

or a salt thereof,

[9] the compound as described in above [1], wherein B is a nitrogen atom, or a salt thereof,

[10] the compound as described in above [1], wherein X is (1) a group of —$NR^2R_3$ wherein $R^2$ and $R^3$ independently represent (i) a hydrogen atom or (ii) a $C_{1-6}$ alkyl group, (2) a group of —N=CHOR$^4$ wherein $R^4$ represents a $C_{1-6}$ alkyl group, or (3) a group of —N=CHNR$_6$R$^7$ wherein $R^6$ and $R^7$ independently represent (i) a hydrogen atom or (ii) a $C_{1-6}$ alkyl group;

$R^8$ is trifluoromethyl;

A is

and

B is a nitrogen atom, or a salt thereof,

[11] the compound as described in above [10], wherein X is (1) a group of —$NR^2R^3$ wherein $R^2$ and $R^3$ independently represent (i) a hydrogen atom or (ii) a $C_{1-6}$ alkyl group, or (2) a group of —N=CHOR$^4$ wherein $R^4$ represents a $C_{1-6}$ alkyl group, or a salt thereof,

[12] the compound as described in above [1], which is 1-(2,6-dichloro-4-trifluoromethylphenyl)-3-{4-(N,N-dimethylcarbamoyl)-Δ$^2$-1,2,4-oxadiazolin-3-yl}-5-isopropoxymethyleneamino-4-trifluoromethylsulfinylpyrazole or a salt thereof,

[13] the compound as described in above [1], which is 1-(2,6-dichloro-4-trifluoromethylphenyl)-3-{4-(N,N-dimethylcarbamoyl)-Δ$^2$-1,2,4-oxadiazolin-3-yl}-5-ethoxymethyleneamino-4-trifluoromethylsulfinylpyrazole or a salt thereof,

[14] the compound as described in above [1], which is 1-(2,6-dichloro-4-trifluoromethylphenyl)-5-ethoxymethyleneamino-3-{4-(morpholinocarbonyl)-Δ$^2$-1,2,4-oxadiazolin-3-yl}-4-trifluoromethylsulfinylpyrazole or a salt thereof,

[15] the compound as described in above [1], which is 1-(2,6-dichloro-4-trifluoromethylphenyl)-5-ethoxymethyleneamino-3-{4-isobutylyl-Δ$^2$-1,2,4-oxadiazolin-3-yl}-4-trifluoromethylsulfinylpyrazole or a salt thereof,

[16] an agrochemical composition which comprises an effective amount of the compound as described in above [1] or a salt thereof,

[17] the agrochemical composition as described in above [16], which is an insecticidal composition,

[18] a method of combatting an insect, which comprises applying or administering an effective dose of the compound as described in above [1] or a salt thereof to a vertebrate, a paddy field, plowland, orchard, non-cropland or house,

[19] use of the compound as described in above [1] or a salt thereof for the manufacture of an agrochemical composition, and

[20] use of the compound as described in above [1] or a salt thereof for combatting an insect.

BEST MODE FOR CARRYING OUT THE INVENTION

The compound of the above formula [I] or a salt thereof of the present invention sometimes have geometrical isomers and/or stereoisomers, and the present invention includes all of these isomers or mixtures of them.

The $C_{1-6}$ alkyl group for $R^1$ includes methyl, ethyl, n-propyl, isopropyl, n-butyl, isobutyl, sec-butyl, or tert-butyl.

The $C_{1-6}$ haloalkyl group for $R^1$ includes a $C_{1-6}$ alkyl group which is substituted with one to ten (preferably one to five) halogen atoms (e.g. fluorine, chlorine, bromine, iodine) such as chloromethyl, fluoromethyl, bromomethyl, 2-chloroethyl, dichloromethyl, trichloromethyl, trifluoromethyl, 2,2,2-trifluoroethyl, pentafluoroethyl, heptafluoropropyl or nonafluorobutyl.

n is 0, 1 or 2, and preferred is 1.

$R^1$ is especially preferably $C_{1-6}$ haloalkyl group such as trifluoromethyl.

The $C_{1-6}$ alkyl group in "$C_{1-6}$ alkyl group which may optionally be substituted with pyridyl group" includes the same ones as mentioned in the above $C_{1-6}$ alkyl group for $R^1$.

The pyridyl group in the definition of $R^2$ and $R^3$ includes 2-, 3- or 4-pyridyl. The alkyl group may be substituted with one or two pyridyl groups.

$R^2$ and $R^3$ preferably represent a hydrogen atom or methyl. Particularly, both $R^2$ and $R^3$ are preferably a hydrogen atom.

The $C_{1-6}$ alkyl group for $R_4$, $R^6$ and $R^7$ includes the same ones as mentioned in the above $C_{1-6}$ alkyl group for $R^1$.

$R^4$ is preferably a $C_{1-6}$ alkyl group. Especially preferred is ethyl or isopropyl.

$R_6$ and $R_7$ are preferably a $C_{1-6}$ alkyl group such as methyl.

The $C_{1-3}$ alkoxy group which may be on the phenyl group for Ar includes methoxy, ethoxy, propoxy or isopropoxy. Especially preferred is methoxy. The phenyl group for Ar may optionally be substituted with one to three substituents selected from the group consisting of hydroxy and the $C_{1-3}$ alkoxy group. Ar is preferably 3-methoxy-4-hydroxyphenyl group.

The pyrrolyl group for X includes 1-, 2- or 3-pyrrolyl group. X is preferably a group of —$NR^2R^3$ ($R^2$ and $R^3$ have the same meanings as defined above) or a group of —N=CHOR$^4$ ($R^4$ has the same meaning as defined above). Especially preferable X is —$NH_2$ or a group of —N=CHOR$^4$ ($R^4$ has the same meaning as defined above).

The alkyl group in "an optionally substituted alkyl group" for $R_5$ includes the same ones as mentioned in the $C_{1-6}$ alkyl group for $R^1$. The substituent of the alkyl group includes hydroxy, amino, a mono- or di-$C_{1-6}$ alkylamino group (e.g. methylamino, ethylamino, propylamino, dimethylamino, diethylamino, etc.), a $C_{1-6}$ alkoxy group (e.g. methoxy, ethoxy, propoxy, isopropoxy, butoxy, etc.), a $C_{1-4}$ alkylthio group (e.g. methylthio, ethylthio, n-propylthio, isopropylthio, butylthio, etc.), halogen (e.g. fluorine, chlorine, bromine, iodine), carboxyl, nitro or cyano. As the substituent, a $C_{1-6}$ alkoxy group is particularly preferable. The number of the substituents is one to six, preferably one to three, within the substitutable range.

As the acyl group in the optionally substituted acyl group, for example, a $C_{1-20}$ acyl group derived from carboxylic acid is used. Specifically, for example, (1) formyl, (2) an alkanoyl group, preferably a $C_{2-10}$ alkanoyl group (e.g. $C_{1-9}$ alkyl-carbonyl such as acetyl, propionyl, butylyl, isobutylyl, pentanoyl, hexanoyl, heptanoyl, pivaloyl, etc.), (3) a cycloalkanoyl group, preferably a $C_{4-10}$ cycloalkanoyl group (e.g. cyclopropylcarbonyl, cyclobutylcarbonyl, cyclopentylcarbonyl, cyclohexylcarbonyl, etc.), (4) an alkenylcarbonyl group, preferably a $C_{3-10}$ alkenylcarbonyl group (e.g. acryloyl, allylcarbonyl, isopropenylcarbonyl, isobutenylcarbonyl, 1-methylallylcarbonyl, cinnamoyl, etc.), (5) an alkynylcarbonyl group, preferably a $C_{3-7}$ alkynylcarbonyl group (e.g. propargylcarbonyl, 2-butynylcarbonyl, 3-butynylcarbonyl, 3-pentynylcarbonyl, etc.), (6) an arylcarbonyl group, preferably a $C_{6-14}$ arylcarbonyl group (e.g. benzoyl, 1-naphthoyl, 2-naphthoyl, etc.), (7) an alkoxycarbonyl group, preferably a $C_{1-6}$ alkoxycarbonyl group (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, etc.), (8) an aryloxycarbonyl group, preferably a $C_{6-14}$ aryloxy-carbonyl group (e.g. phenoxycarbonyl), (9) an aralkylcarbonyl group, preferably a $C_{7-19}$ aralkyl-carbonyl group (e.g. phenyl-$C_{1-4}$ alkylcarbonyl such as benzylcarbonyl, phenethylcarbonyl or phenylpropylcarbonyl; benzhydrylcarbonyl; naphthyl-$C_{1-4}$ alkylcarbonyl such as 1-naphthylethylcarbonyl, etc.), (10) an aralkyloxycarbonyl group, preferably a $C_{7-19}$ aralkyloxycarbonyl group (e.g. phenyl-$C_{1-4}$ alkyloxycarbonyl such as benzyloxycarbonyl, phenethyloxycarbonyl, phenylpropyloxycarbonyl, etc.), (11) carbamoyl or (12) a cyclic aminocarbonyl group (e.g. 1-pyrrolidinocarbonyl, piperidinocarbonyl, morpholinocarbonyl, thiomorpholinocarbonyl, 1-perhydroazepinylcarbonyl, etc.) is used.

When the acyl group is alkanoyl, alkenylcarbonyl or alkynylcarbonyl, each group may optionally have one to six (preferably one to three) substituents selected from the group consisting of hydroxy, amino, a mono- or di-$C_{1-6}$ alkylamino group (e.g. methylamino, ethylamino, propylamino, dimethylamino, diethylamino, etc.), a $C_{1-6}$ alkoxy group (e.g. methoxy, ethoxy, propoxy, isopropoxy, butoxy, etc.), a $C_{1-6}$ alkylthio group (e.g. methylthio, ethylthio, n-propylthio, isopropylthio, n-butylthio, etc.), halogen (e.g. fluorine, chlorine, bromine, iodine), carboxyl, nitro, cyano and phenyl.

When the acyl group is cycloalkanoyl, arylcarbonyl, alkoxycarbonyl, aryloxycarbonyl, aralkylcarbonyl or aralkyloxycarbonyl, each group may optionally have one to five (preferably one to three) substituents selected from the group consisting of hydroxy, amino, a mono- or di-$C_{1-6}$ alkylamino group (e.g. methylamino, ethylamino, propylamino, dimethylamino, diethylamino, etc.), a $C_{1-6}$ alkoxy group (e.g. methoxy, ethoxy, propoxy, isopropoxy, butoxy, etc.), a $C_{1-6}$ alkylthio group (e.g. methylthio, ethylthio, n-propylthio, isopropylthio, n-butylthio, etc.), halogen (e.g. fluorine, chlorine, bromine, iodine), carboxyl, nitro, cyano, phenyl, a $C_{1-6}$ alkyl group (e.g. methyl, ethyl, n-propyl, isopropyl, n-butyl, isobutyl, sec-butyl, tert-butyl, etc.), a $C_{2-6}$ alkenyl group (e.g. vinyl, allyl, 1-propenyl, 1-butenyl, 2-butenyl, etc.) and a $C_{2-6}$ alkynyl group (e.g. ethynyl, 1-propynyl, propargyl, 1-butynyl, etc.).

When the acyl group is carbamoyl, the carbamoyl may optionally have one or two substituents selected from the group consisting of (1) a $C_{1-6}$ alkyl group (e.g. methyl, ethyl, n-propyl, isopropyl, n-butyl, isobutyl, sec-butyl, tert-butyl, etc.), (2) a $C_{3-9}$ cycloalkyl group (e.g. cyclopropyl, cyclobutyl, cyclopentyl, cyclohexyl, etc.), (3) a $C_{2-6}$ alkenyl group (e.g. vinyl, allyl, 1-propenyl, 1-butenyl, 2-butenyl, etc.), (4) a $C_{26}$ alkynyl group (e.g. ethynyl, 1-propynyl, propargyl, 1-butynyl, etc.), (5) hydroxy, (6) a $C_{1-6}$ alkoxy group (e.g. methoxy, ethoxy, propoxy, isopropoxy, butoxy, etc.), (7) amino, (8) a mono- or di-$C_{1-6}$ alkylamino group (e.g. methylamino, ethylamino, propylamino, dimethylamino, diethylamino, etc.), (9) a cyclic amino group (e.g. 1-pyrrolidino, piperidino, morpholino, 4-methyl-1-piperadino, etc.) and (10) phenyl. Further, such substituents may form a cyclic amino group (e.g. 1-pyrrolidino, piperidino, morpholino, thiomorpholino, 4-methyl-1-piperadino, etc.) together with an adjacent nitrogen atom. Moreover, these substituents may further optionally be substituted with one to six (preferably one to three) substituents selected from the group consisting of hydroxy, amino, a mono- or di-$C_{1-6}$ alkylamino group (e.g. methylamino, ethylamino, propylamino, dimethylamino, diethylamino, etc.), a $C_{1-6}$ alkoxy group (e.g. methoxy, ethoxy, propoxy, isopropoxy, butoxy, etc.), a $C_{1-6}$ alkylthio group (e.g. methylthio, ethylthio, n-propylthio, isopropylthio, n-butylthio, etc.),halogen (e.g. fluorine, chlorine, bromine, iodine), phenyl, carboxyl, nitro and cyano.

Among them, $R^5$ is preferably an optionally substituted alkyl group, an optionally substituted alkanoyl group, an optionally substituted cycloalkanoyl group, an optionally substituted alkenylcarbonyl group, an optionally substituted arylcarbonyl group, an optionally substituted alkoxycarbonyl group or an optionally substituted carbamoyl group, and is more preferably an optionally substituted carbamoyl group. Among them, particularly preferred is (1) a $C_{1-6}$ alkyl group which may optionally be substituted with one to three $C_{1-6}$ alkoxy groups, (2) a $C_{2-10}$ alkanoyl group which may optionally be substituted with one to three substituents selected from the group consisting of amino which may optionally be substituted with one or two $C_{1-6}$ alkyl groups, $C_{1-6}$ alkoxy group, phenyl and halogen atom, (3) a $C_{4-10}$ cycloalkanoyl group, (4) a $C_{3-10}$ alkenylcarbonyl group, (5) benzoyl, (6) carbamoyl which may optionally be substituted with one or two substituents selected from the group consisting of (i) a $C_{1-6}$ alkyl group which may optionally be substituted with one to three substituents selected from the group consisting of phenyl, halogen and amino which may optionally be substituted with one or two $C_{1-6}$ alkyl groups, (ii) a $C_{3-9}$ cycloalkyl group, (iii) a $C_{2-6}$ alkenyl group, (iv) a $C_{2-6}$ alkynyl group, (v) phenyl, (vi) amino which may optionally be substituted with one or two $C_{1-6}$ alkyl groups, (vii) cyclic amino group (e.g. pyrrolidino, piperidino), (viii) hydroxy and (ix) a $C_{1-6}$ alkoxy group, (7) cyclic aminocarbonyl group (e.g. pyrrolidinocarbonyl, piperidinocarbonyl, 1-perhydroazepinylcarbonyl, 4-methyl-1-piperazinylcarbonyl, morpholinocarbonyl), (8) a $C_{1-6}$ alkoxy-carbonyl group or (9) formyl.

The halogen for $R^8$ includes fluorine, chlorine, bromine or iodine.

The $C_{1-6}$ haloalkyl group for $R^8$ includes the same ones as mentioned in the $C_{1-6}$ haloalkyl group for $R^1$.

The $C_{1-6}$ haloalkoxy group for $R^8$ includes a $C_{1-6}$ alkoxy group which is substituted with one to ten (preferably one to five) halogen atoms (e.g. fluorine, chlorine, bromine, iodine) such as chloromethoxy, fluoromethoxy, bromomethoxy, 2-chloroethoxy, dichloroethoxy, trichloromethoxy, trifluoromethoxy, 2,2,2-trifluoroethoxy, pentafluoroethoxy, heptafluoropropoxy or nonafluorobutoxy. Particularly preferred is trifluoromethoxy.

The $C_{1-6}$ haloalkyl group in the "phenyl which may optionally be substituted with a $C_{1-6}$ haloalkyl group" includes the same ones as mentioned in the $C_{1-6}$ haloalkyl group for $R^1$. The number of the substituents on the phenyl is one to five, preferably one to three. Particularly, phenyl which may optionally be substituted with one to three trifluoromethyl groups is preferable.

A is preferably

B is preferably a nitrogen atom.

As a compound [I], a compound represented by the formula:

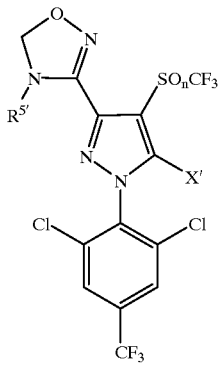

wherein n is 0, 1 or 2;

X' is —$NH_2$, —$N=CHOR^{4'}$ ($R^{4'}$ represents a $C_{1-6}$ alkyl group) or —$N=CHNR^{6'}R^{7'}$ ($R^{6'}$ and $R^{7'}$ independently represent a $C_{1-6}$ alkyl group); and $R^{5'}$ is (1) a $C_{1-6}$ alkyl group which may optionally be substituted with a $C_{1-6}$ alkoxy group, (2) a $C_{1-9}$ alkyl-carbonyl group which may optionally be substituted with one to three substituents selected from the group consisting of a mono- or di-$C_{1-6}$ alkylamino group, phenyl, a $C_{1-6}$ alkoxy group and halogen, (3) benzoyl, (4) a $C_{4-20}$ cycloalkanoyl group, (5) a $C_{3-10}$ alkenylcarbonyl group which may optionally be substituted with one or two phenyl, (6) formyl, (7) a $C_{1-6}$ alkoxy-carbonyl group, (8) carbamoyl which may optionally be substituted with one or two substituents selected from the group consisting of a $C_{1-6}$ alkyl group, a $C_{2-6}$ alkenyl group, a $C_{2-6}$ alkynyl group, phenyl, benzyl, a mono- or di-$C_{1-6}$ alkylamino, hydroxy, a $C_{1-6}$ alkoxy group, a $C_{3-9}$ cycloalkyl group and piperidino, or (9) cyclic amino-carbonyl group selected from pyrrolidinocarbonyl, piperidinocarbonyl, 1-perhydroazepinylcarbonyl, 4-methyl-1-piperazinylcarbonyl and morpholinocarbonyl; is preferable.

More preferable compound II is a compound represented by the formula:

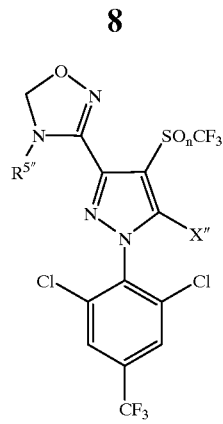

wherein n is 0, 1 or 2;

X" is —$NH_2$ or -$N=CHOR^{4''}$ ($R^{4''}$ is a $C_{1-6}$ alkyl group); and $R^{5''}$ is (1) a $C_{1-9}$ alkyl-carbonyl group or (2) carbamoyl which may optionally be substituted with one or two $C_{1-6}$ alkyl groups.

Further more preferable compound [I] is a compound represented by the formula:

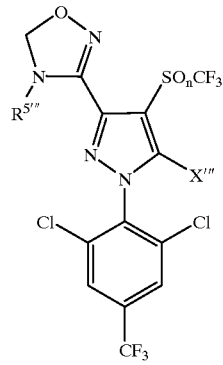

wherein n is 0, 1 or 2;

X''' is —$N=CHOR^{4'''}$ ($R^{4'''}$ is a $C_{1-6}$ alkyl group); and $R^{5'''}$ is carbamoyl which may optionally be substituted with one or two $C_{1-6}$ alkyl groups.

The salt of the compound [I] of the present invention may be any agrochemically acceptable salt. That is, when the compound [I] has an acidic group such as a carboxyl group, a sulfo group, etc. in the molecule, the compound [I] may form a salt with a base. As the base, for example, there can be used inorganic bases such as alkali metal, e.g. sodium, potassium, lithium; alkaline earth metal, e.g. calcium, magnesium; ammonia and the like; and organic bases such as pyridine, collidine, triethylamine, triethanolamine and the like. Also, when the compound [I] has a basic group such as an amino group, etc. in the molecule, the compound [I] may form a salt with an acid. As the acid, for example, there can be used salts of inorganic acids such as hydrochloric acid, hydrobromic acid, hydroiodic acid, phosphoric acid, sulfuric acid, perchloric acid and the like; and salts of organic acids such as formic acid, acetic acid, tartaric acid, malic acid, citric acid, oxalic acid, succinic acid, benzoic acid, picric acid, methanesulfonic acid, p-toluenesulfonic acid and the like. The compound [I] may form an intramolecular salt and the case is also included in the present invention.

The compound [I] or a salt thereof of the present invention and the compound [II] shown below which serve as starting materials in the production of the compound [I] or a salt thereof can be produced by the process described in WO 97/28126 or analogous processes thereof.

Generally, the compound [I] or a salt thereof according to the present invention can be synthesized by reacting the starting compound [II] with an acylating agent or an alkylating agent, optionally in the presence of an appropriate acid or base catalyst. The acylating agent to be used in such reaction includes known acylating agents such as carboxylic acid halides (e.g. acetyl chloride, propionyl bromide, etc.), carbamoyl halides (e.g. N,N-dimethylcarbamoyl chloride, N,N-diethylcarbamoyl chloride, etc.), halocarbonic acid esters (e.g. methyl chlorocarbonate, phenyl chlorocarbonate, etc.), dialkyl dicarboantes (e.g. di-tert-butyl dicarbonate, dimethyl dicarbonate, etc.), and carboxylic acid anhydrides (e.g. acetic anhydride, propionic anhydride, etc.). The alkylating agent to be used in such reaction includes known alkylating agents such as alkyl halides (e.g. methyl iodide, ethyl bromide, etc.), alkyl sulfonates (e.g. methyl methanesulfonate, ethyl p-toluenesulfonate, methyl trifluoromethane sulfonate, etc.), dialkyl sulfates (e.g. dimethyl sulfate, diethyl sulfate, etc.), and trialkyl orthoformates (e.g. trimethyl orthoformate, triethyl orthoformate, etc.). In this reaction, the amount of the acylating agent or alkylating agent mentioned above is not particularly restricted. Said agent may be used in large excess so that it may serve as a solvent as well.

The base catalyst to be used in this reaction includes alkali metal alcoholates such as sodium ethylate, sodium imethylate and potassium tert-butoxide; organic bases such as triethylamine, diisopropylethylamine, pyridine, 4-dimethylaminopyridine and N,N-dimethylaniline; and inorganic bases such as potassium carbonate, sodium carbonate, sodium hydroxide, potassium hydroxide, sodium hydrogen carbonate, potassium hydrogen carbonate and sodium hydride. The amount of the base to be used is not particularly restricted provided that it does not adversely affect the reaction. The base may be used in large excess so that it may serve as a solvent as well. A preferred amount is 0.1 to 20 equivalents, however.

The acid catalyst to be used in this reaction includes inorganic protic acids such as hydrochloric acid, hydrobromic acid, hydroiodic acid, phosphoric acid and sulfuric acid; organic protic acids such as formic acid, acetic acid, tartaric acid, malic acid, citric acid, oxalic acid, succinic acid, benzoic acid, trifluoroacetic acid and p-toluenesulfonic acid; and Lewis acids such as aluminum chloride, ferric chloride, zinc chloride, titanium tetrachloride and boron trifluoride. The amount of the acid catalyst to be submitted to the reaction is not particularly restricted unless it adversely affects the reaction. The acid catalyst may be used in large excess so that it may serve as a solvent as well. Preferably, it is used in an amount of 0.1 to 20 equivalents.

This reaction can be carried out using an appropriate solvent. Such solvent is not restricted to any particular species provided that it does not react with the substrate, reagent or product of the reaction. Those solvents which can dissolve both the reaction substrate and reaction reagent are preferred, however. As such solvents, there may be mentioned, for example, aliphatic hydrocarbons such as pentane, hexane, heptane and petroleum ether; aromatic hydrocarbons such as benzene, toluene and xylene; esters such as methyl acetate, ethyl acetate, ethyl formate and ethyl propionate; ketones such as acetone and methyl ethyl ketone; ethers such as diethyl ether, dipropyl ether, diusopropyl ether, dibutyl ether, tetrahydrofuran and dioxane; nitriles such as acetonitrile and propionitrile; acid amides such as dimethylformamide and dimethylacetamide; sulfoxides such as dimethyl sulfoxide; sulfones such as sulfolane; phosphoric acid amides such as hexamethylphosphoramide; halogenated hydrocarbons such as dichloromethane, chloroform, 1,2-dichloroethane and carbon tetrachloride; aromatic amines such as pyridine, picoline, lutidine and quinoline; mixtures of these solvents; water; and, further, mixed solvents composed of any of said solvents and water.

The reaction temperature is generally within the range of about −50° C. to 200° C., and the reaction time is generally within the range of about 0.1 to 96 hours.

When the compounds [I] are obtained in the free form, they may be converted to a form of salts such as mentioned above and, when they are obtained in the form of salts, they may respectively be converted to the free form in the conventional manner. In cases where a compound included in the group of compounds [I] is used as a starting material for the production of another compound of formula [I], the starting compound may be used either in the free form or in the form of a salt. If other raw materials can take the form of salts such as mentioned above, they also may be used either in the free form or in the form of such salts. Therefore, it is to be noted that the raw materials and products mentioned in the description of the production processes given below include also salts thereof (e.g. salts with acids such as mentioned with reference to the compounds [I]).

Specifically, the compounds [I] and salts thereof can be produced by the following processes, for instance. [Reaction schema (A)]

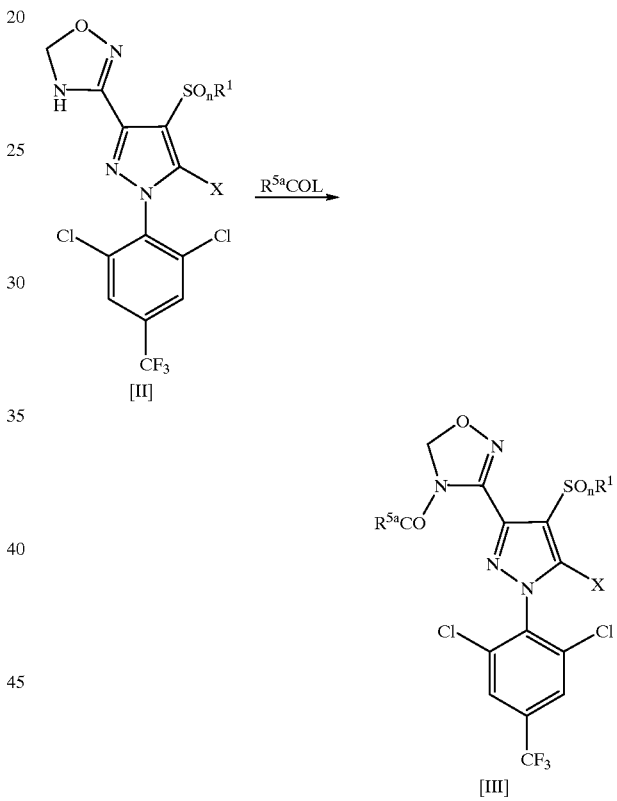

[Reaction schema (B)]

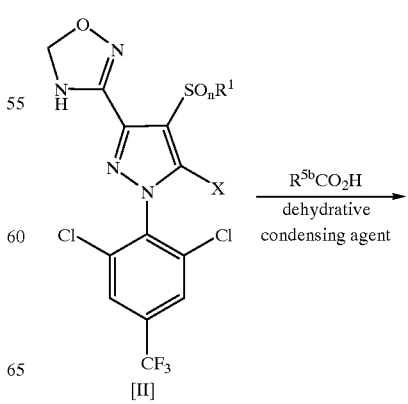

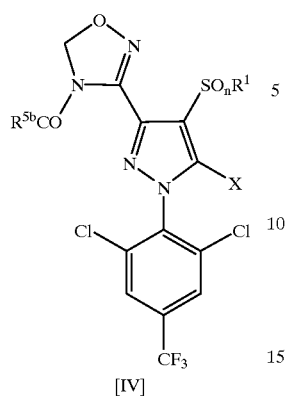
[IV]
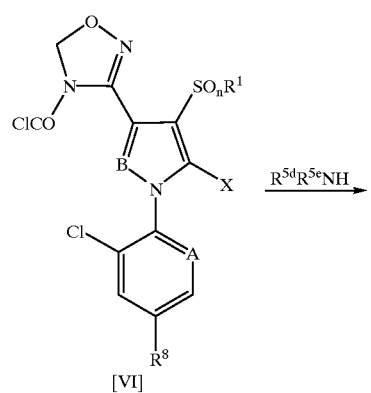
[VI]
[Reaction schema (C)]
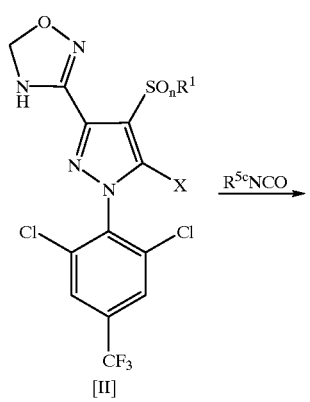
[II]
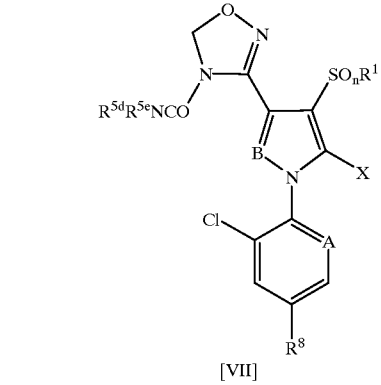
[VII]
[Reaction schema (E)]
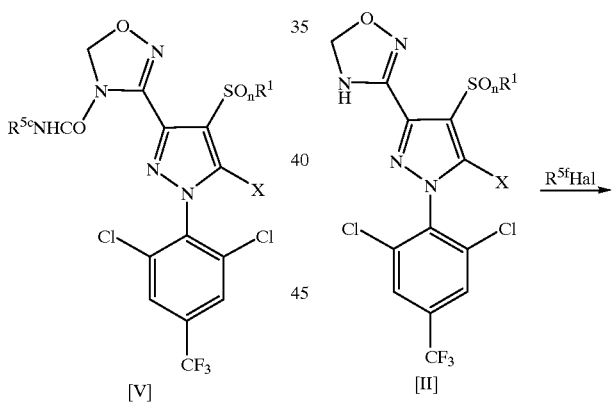
[V] [II]
[Reaction schema (D)]
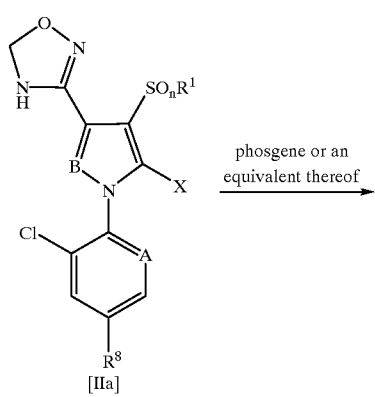
[IIa]
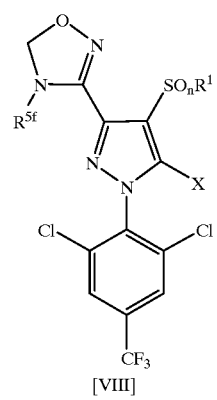
[VIII]

[Reaction schema (F)]
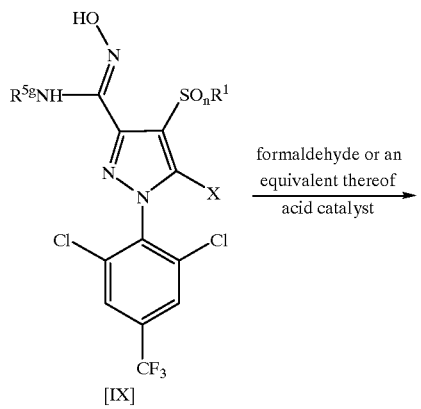
formaldehyde or an equivalent thereof
acid catalyst
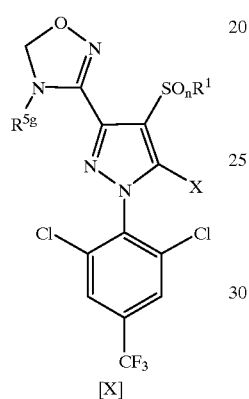
[Reaction schema (G)]
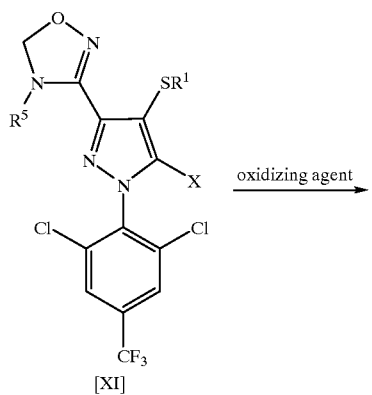
oxidizing agent
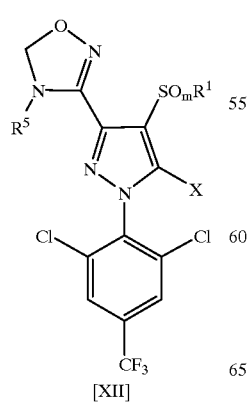
[Reaction schema (H)]
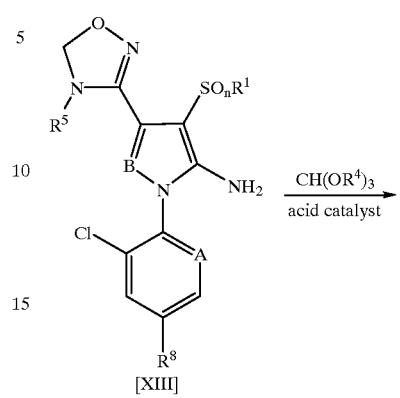
$CH(OR^4)_3$
acid catalyst
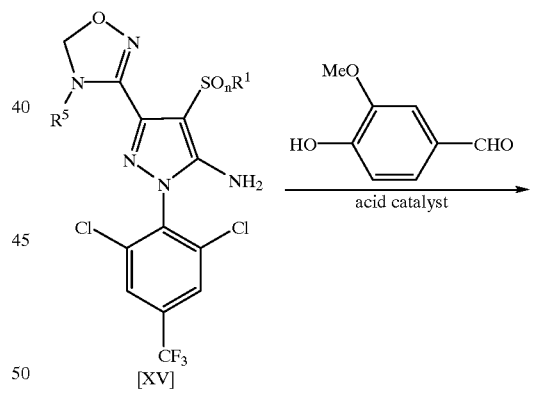
[Reaction schema (I)]
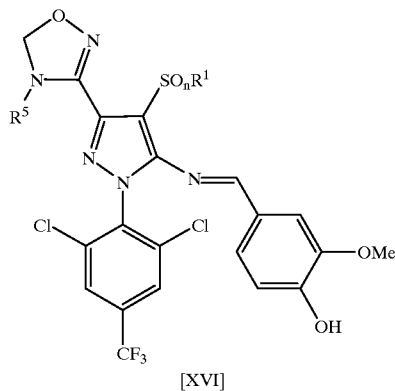

-continued
[Reaction schema (J)]

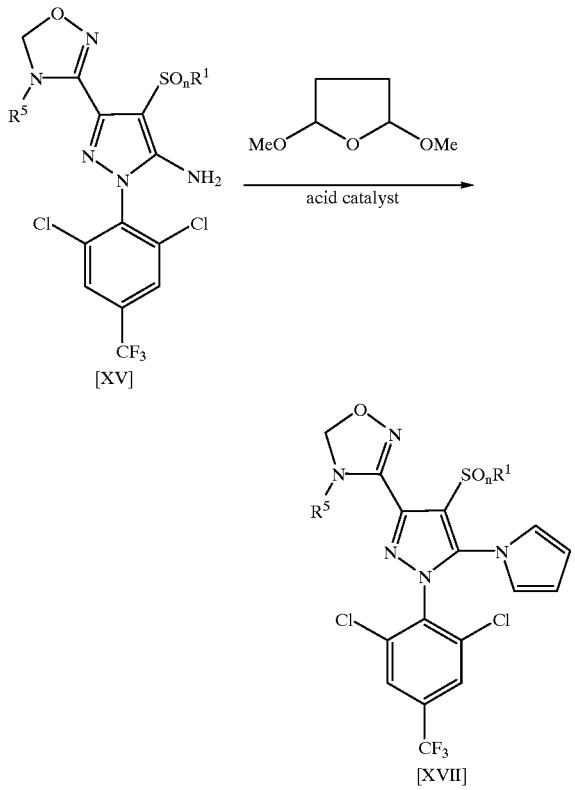

In the above reaction schema (A) to (J), each symbol of A, B, X, n, $R^1$, $R^4$, $R_5$ and $R^8$ has the same meaning as defined above. $R^{5a}$ represents an optionally substituted $C_{1-9}$ alkyl group, an optionally substituted $C_{3-9}$ cycloalkyl group, an optionally substituted $C_{2-6}$ alkenyl group, an optionally substituted phenyl group, a $C_{1-6}$ alkoxy group, or a mono- or di-$C_{1-6}$ alkylamino group; $R^{5b}$ represents an optionally substituted $C_{1-6}$ alkyl group, an optionally substituted $C_{3-9}$ cycloalkyl group, an optionally substituted $C_{2-6}$ alkenyl group, or an optionally substituted phenyl group; $R^{5c}$, $R^{5f}$ and $R_{5g}$ independently represent an optionally substituted $C_{1-6}$ alkyl group; m is 1 or 2; $R^{5d}$ and $R^{5e}$ independently represent a hydrogen atom, an optionally substituted $C_{1-6}$ alkyl group, an optionally substituted $C_{3-9}$ cycloalkyl group, an optionally substituted $C_{2-6}$ alkenyl group, an optionally substituted $C_{2-6}$ alkynyl group, an optionally substituted phenyl group, a mono- or di-$C_{1-6}$ alkylamino group, a cyclic amino group, hydroxy, a $C_{1-6}$ alkoxy group, or $R^{5d}$ and $R^{5e}$ may be combined to form a cyclic amino group together with an adjacent nitrogen atom.

The alkyl group in the optionally substituted $C_{1-9}$ alkyl group for $R^{5a}$ and $R^{5b}$ includes methyl, ethyl, n-propyl, isopropyl, n-butyl, isobutyl, sec-butyl, tert-butyl, n-pentyl, neo-pentyl, 1-ethylpropyl, 1-propylbutyl, n-hexyl, n-heptyl, n-octyl, or n-nonyl, etc. The substituent for the alkyl group includes the same ones as mentioned for the substituent of the optionally substituted alkyl group of $R^5$. The number of the substituents is one to six, preferably one to three, within the substitutable range.

The optionally substituted $C_{1-6}$ alkyl group for $R^{5c}$, $R^{5d}$, $R^{5e}$, $R^{5f}$ and $R_{5g}$ includes the same ones as mentioned for the optionally substituted alkyl group of above-mentioned $R^5$.

The substituent for the phenyl group of $R_{5a}$, $R^{5b}$, $R^{5d}$ and $R_{5e}$ includes the same ones as mentioned for the substituent on the acyl group (arylcarbonyl group) of above-mentioned $R^5$. The number of the substituents is one to five, preferably one to three.

The $C_{1-6}$ alkoxy group for $R^{5a}$, $R^{5d}$ and $R^{5e}$ includes methoxy, ethoxy, propoxy, isopropoxy, butoxy, isobutoxy, sec-butoxy, or tert-butoxy, etc.

The $C_{1-6}$ alkyl group in the mono- or di-$C_{1-6}$ alkylamino group for $R_{5a}$, $R^{5d}$ and $R_{5e}$ includes the same ones as mentioned for the alkyl group of above-mentioned $R^1$.

The cycloalkyl group in the optionally substituted $C_{3-9}$ cycloalkyl group includes cyclopropyl, cyclobutyl, cyclopentyl, or cyclohexyl, etc.

The alkenyl group in the optionally substituted $C_{2-6}$ alkenyl group for $R_{5a}$, $R^{5b}$, $R^{5d}$ and $R^{5e}$ includes vinyl, allyl, 1-propenyl, 1-butenyl, or 2-butenyl, etc.

The alkynyl group in the optionally substituted $C_{2-6}$ alkynyl group for $R_{5d}$ and $R^{5e}$ includes ethynyl, 1-propynyl, propargyl, or 1-butynyl, etc.

The cyclic amino group for $R^{5d}$ and $R^{5e}$ includes 1-pyrrolidino, piperidino, morpholino, or 4-methyl-1-piperazino, etc.

The above-mentioned cycloalkyl, alkenyl, alkynylor cyclic amino group may optionally be substituted with one to six (preferably one to three) substituents selected from the group consisting of hydroxy, amino, a mono- or di-$C_{1-6}$ alkylamino group (e.g. methylamino, ethylamino, propylamino, dimethylamino, diethylamino, etc.), a $C_{1-6}$ alkoxy group (e.g. methoxy, ethoxy, propoxy, isopropoxy, butoxy, etc.), a $C_{1-6}$ alkylthio group (e.g. methylthio, ethylthio, n-propylthio, isopropylthio, n-butylthio, etc.), halogen (e.g. fluorine, chlorine, bromine, iodine), phenyl, carboxyl, nitro and cyano.

Also, the cyclic amino group in which $R^{5d}$ and $R^{5e}$ may form together with an adjacent nitrogen atom includes 1-pyrrolidino, piperidino, morpholino, or 4-methyl-1-piperazino, etc.

The reaction schema (A) represents the reaction of a compound [II] with an acylating agent of the formula $R^{5a}$COL [wherein L represents a leaving group such as a halogen atom (e.g. fluorine, chlorine, bromine, iodine) or an acyloxy group such as a $C_{1-10}$ acyloxy group (e.g. formyloxy; or a $C_{1-6}$ alkyl-carbonyloxy group which may optionally be substituted with 1 to 3 halogen atoms, such as acetoxy, propionyloxy or trifluoroacetoxy; or a $C_{1-6}$ alkoxy-carbonyloxy group such as methoxycarbonyloxy or t-butoxycarbonyloxy)] to give the corresponding compound [III].

The compound [II] not only serves as the starting material for this reaction but also has excellent insecticidal activity by itself. As preferred examples of the compound [III], there may be mentioned 1-(2,6-dichloro-4-trifluoromethylphenyl)-5-ethoxymethyleneamino-3-($\Delta^2$-1,2,4-oxadiazolin-3-yl)-4-trifluoromethylsulfinylpyrazole, 1-(2,6-dichloro-4-trifluoromethylphenyl)-3-($\Delta^2$-1,2,4-oxadiazolin-3-yl)- 5-(n-propoxymethyleneamino)-4-trifluoromethylthiopyrazole and 1-(2,6-dichloro-4-trifluoromethylphenyl)-3-($\Delta^2$-1,2,4-oxadiazolin-3-yl)-5-(n-propoxymethyleneamino)-4-trifluoromethylsulfonylpyrazole, among others.

In this reaction, the amount of the acylating agent mentioned above is not particularly restricted. Said agent may be used in large excess so that it may serve as a solvent as well. Preferably, it is used in an amount of about 0.8 to 5 equivalents.

In some instances, when the reaction is carried out in the presence of a base for the purpose of promoting the reaction and reducing the byproduct formation or when the starting material is treated with a base prior to the reaction or the reaction mixture after the reaction is treated with a base, favorable results can be obtained. Usable as such base are, for example, alkali metal alcoholates such as sodium ethylate, sodium methylate and potassium tert-butoxide; organic bases such as triethylamine, diisopropylethylamine, pyridine, 4-dimethylaminopyridine and N,N-dimethylaniline; and inorganic bases such as potassium carbonate, sodium carbonate, sodium hydroxide, potassium hydroxide, sodium hydrogen carbonate, potassium hydrogen carbonate and sodium hydride. The amount of the base to be used is not particularly restricted unless it adversely affects the reaction. Said base may be used in large excess so that it may serve as a solvent as well.

This reaction can be carried out using an appropriate solvent. Such solvent is not restricted to any particular species provided that it does not react with the substrate, reagent or product of the reaction, hence does not cause byproduct formation. Those solvents which can dissolve both the reaction substrate and reaction reagent are preferred, however. As such solvents, there may be mentioned, for example, aliphatic hydrocarbons such as pentane, hexane, heptane and petroleum ether; aromatic hydrocarbons such as benzene, toluene and xylene; esters such as methyl acetate, ethyl acetate, ethyl formate and ethyl propionate; ketones such as acetone and methyl ethyl ketone; ethers such as diethyl ether, dipropyl ether, diisopropyl ether, dibutyl ether, tetrahydrofuran and dioxane; nitriles such as acetonitrile and propionitrile; acid amides such as dimethylformamide and dimethylacetamide; sulfoxides such as dimethyl sulfoxide; sulfones such as sulfolane; phosphoric acid amides such as hexamethylphosphoramide; halogenated hydrocarbons such as dichloromethane, chloroform, 1,2-dichloroethane andcarbontetrachloride; aromaticaminessuchaspyridine, picoline, lutidine and quinoline; mixtures of these solvents; water and, further, mixed solvents composed of any of said solvents and water.

The reaction temperature is generally within the range of about −50° C. to 200° C., preferably about −30° C. to 150° C., and the reaction time is generally within the range of about 0.1 to 96 hours, preferably 0.1 to 72 hours, more preferably about 0.1 to 24 hours.

The compound obtained can be isolated and purified by per se known means, such as concentration, concentration under reduced pressure, pH adjustment, solvent exchange, solvent extraction, distillation, crystallization, recrystallization, chromatography and the like. Said compound may be submitted to the next reaction either after such isolation/purification or in the form of a reaction mixture.

The reaction schema (B) represents the reaction of a compound [II] with a carboxylic acid derivative of the formula $R^{5a}CO_2H$ [wherein $R^{5a}$ is as defined above] in the presence of a dehydrative condensing agent to give the corresponding compound [IV].

The dehydrative condensing agent to be used in this reaction includes known dehydrative condensing agents such as DCC (dicyclohexylcarbodiimide), carbonyldiimidazole, and BOP reagent (benzotriazol-1-yloxy-tris(dimethylamino)phosphonium hexafluorophosphate). The amount to be used is not particularly restricted but preferably is 0.8 to 5 equivalents.

The amount of the carboxylic acid derivative to be used in this reaction is not particularly restricted. Said derivative may be used in large excess so that it may serve as a solvent as well. Generally, it is used in an amount of about 0.8 to 5 equivalents.

The reaction schema (C) represents the reaction of a compound [II] with an isocyanate derivative of the formula $R_{5c}NCO$ [wherein $R^{5c}$ is as defined above] to give the corresponding compound [V].

The amount of the isocyanate derivative to be used in this reaction is not particularly restricted. Said derivative may be used in large excess so that it may serve as a solvent as well. Preferably, it is used in an amount of about 0.8 to 5 equivalents. In some instances, when the reaction is carried out in the presence of a base for the purpose of promoting the reaction and reducing the byproduct formation or when the starting material is treated with a base prior to the reaction or the reaction mixture after the reaction is treated with a base, favorable results can be obtained. Examples and the amount to be used of such base are the same as those mentioned above in relation to reaction schema (A).

The reaction schema (D) represents the reaction of a compound [IIa] with phosgene or an equivalent thereof to give the corresponding intermediate [VI] and the subsequent reaction of [VI] with an amine of the formula $R^{5d}R^{5e}NH$ [wherein $R_{5d}$ and $R^{5e}$ are as defined above] to give the corresponding compound [VII]. In the compound [IIa], a compound wherein B represents =CH— can be produced according to a method described in the above-mentioned WO97/28126, or analogous methods thereof.

The phosgene or an equivalent thereof to be used in this reaction includes phosgene, trichloromethyl chloroformate (diphosgene), bis(trichloromethyl) carbonate (triphosgene) and the like. Although the amount to be used is not particularly restricted, an amount of 0.3 to 5 equivalents is preferred.

The intermediate [VI] may be used as the starting material in the next reaction either after isolation/purification by per se known means such as concentration, concentration under reduced pressure, pH adjustment, solvent exchange, solvent extraction, distillation, crystallization, recrystallization, chromatography and the like, or in the form of a reaction mixture.

The amount of the amine of the formula: $R^{5d}R^{5e}NH$ to be used in this reaction is not particularly restricted. The amine may be used in large excess so that it may serve as a solvent as well. Generally, it is used in an amount of about 0.8 to 5 equivalents.

The reaction schema (E) represents the reaction of a compound [II] with an alkyl halide of the formula: $R^{5f}Hal$ [wherein $R^{5f}$ is as defined above and Hal represents a halogen atom (e.g. fluorine, chlorine, bromine, iodine)] to give the corresponding compound [VIII].

The amount of the alkyl halide of the formula: $R^{5f}Hal$ to be used in this reaction is not particularly restricted. The alkyl halide may be used in large excess so that it may serve as a solvent as well. Generally, it is used in an amount of about 0.8 to 5 equivalents. In some instances, when the reaction is carried out in the presence of a base for the purpose of promoting the reaction and reducing the byproduct formation or when the starting material is treated with a base prior to the reaction or the reaction mixture after the reaction is treated with a base, favorable results can be obtained. Examples and the amount to be used of such base are the same as those mentioned above in relation to reaction schema (A).

The reaction schema. (F) represents the reaction of a compound [IX] with formaldehyde or an equivalent thereof to give the corresponding compound [X].

The formaldehyde or an equivalent thereof to be used in this reaction includes formaldehyde and paraformaldehyde, among others. The amount to be used is not particularly restricted. This reagent may be used in large excess so that it may serve as a solvent as well. Preferably, it is used in an amount of 0.8 to 15 equivalents. In some instances, when the reaction is carried out in the presence of an acid for the purpose of promoting the reaction and reducing the byproduct formation or when the starting material is treated with an acid prior to the reaction or the reaction mixture after the reaction is treated with an acid, favorable results can be obtained. Usable as such acid catalyst are inorganic prbtic acids such as hydrochloric acid, hydrobromic acid, hydroiodic acid, phosphoric acid and sulfuric acid; organic protic acids such as formic acid, acetic acid, tartaric acid, malic acid, citric acid, oxalic acid, succinic acid, benzoic acid, trifluoroacetic acid and p-toluenesulfonic acid; and Lewis acids such as aluminum chloride, ferric chloride, zinc chloride, titanium tetrachloride and boron trifluoride. The amount of such acid catalyst to be used in the reaction is not particularly restricted unless it adversely affects the reaction. The acid catalyst may be used in large excess so that it may serve as a solvent as well.

The reaction schema (G) represents the oxidation reaction of a compound [XI] with an oxidizing agent to give the corresponding compound [XII].

The oxidizing agent to be used in this reaction includes, among others, hydrogen peroxide, peracetic acid, perbenzoic acid, m-chloroperbenzoic acid, sodium metaperiodate, ozone, selenium dioxide, chromic acid, bromine, N-bromosuccinimide, iodosylbenzene, t-butyl hypochlorite and the like. The amount to be used is not particularly restricted. The oxidizing agent may be used in large excess so that it may serve as a solvent as well. Preferably, it is used in an amount of 0.8 to 5 equivalents.

The reaction schema (H) represents the reaction of a compound [XIII] with a trialkyl orthoformate of the formula: $CH(OR^4)_3$ to give the corresponding compound [XIV]. The amount of the trialkyl orthoformate to be used in this reaction is not particularly restricted. Said orthoformate may be used in large excess so that it may serve as a solvent as well. Preferably, it is used in an amount of 0.8 to 15 equivalents. In some instances, when the reaction is carried out in the presence of an acid for the purpose of promoting the reaction and reducing the byproduct formation or when the starting material is treated with an acid prior to the reaction or the reaction mixture after the reaction is treated with an acid, favorable results can be obtained. Usable as such acid catalyst are inorganic protic acids such as hydrochloric acid, hydrobromic acid, hydroiodic acid, phosphoric acid and sulfuric acid; organic protic acids such as formic acid, acetic acid, tartaric acid, malic acid, citric acid, oxalic acid, succinic acid, benzoic acid, trifluoroacetic acid, methanesulfonic acid and p-toluenesulfonic acid; and Lewis acids such as aluminum chloride, ferric chloride, zinc chloride, titanium tetrachloride and boron trifluoride. The amount of such acid catalyst to be used in the reaction is not particularly restricted unless it adversely affects the reaction. The acid catalyst may be used in large excess so that it may serve as a solvent as well.

The reaction schema (I) represents the reaction of a compound [XV] with a vanillin of the formula:

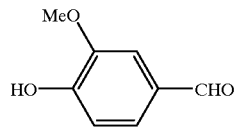

[wherein Me represents a methyl group] to give the corresponding compound [XVI]. The amount of the vanillin to be used in this reaction is not particularly restricted. Said vanillin may be used in large excess so that it may serve as a solvent as well. Preferably, it is used in an amount of 0.8 to 15 equivalents. In some instances, when the reaction is carried out in the presence of an acid for the purpose of promoting the reaction and reducing the byproduct formation or when the starting material is treated with an acid prior to the reaction or the reaction mixture after the reaction is treated with an acid, favorable results can be obtained. Usable as such acid catalyst are inorganic protic acids such as hydrochloric acid, hydrobromic acid, hydroiodic acid, phosphoric acid and sulfuric acid; organic protic acids such as formic acid, acetic acid, tartaric acid, malic acid, citric acid, oxalic acid, succinic acid, benzoic acid, trifluoroacetic acid and p-toluenesulfonic acid; and Lewis acids such as aluminum chloride, ferric chloride, zinc chloride, titanium tetrachloride and boron trifluoride. The amount of such acid catalyst to be used in the reaction is not particularly restricted unless it adversely affects the reaction. The acid catalyst may be used in large excess so that it may serve as a solvent as well.

The reaction schema (J) represents the reaction of a compound [XV] with 2,5-dimethoxytetrahydrofuran to give the corresponding compound [XVII]. The amount of 2,5-dimethoxytetrahydrofuran to be used in this reaction is not particularly restricted. Said 2,5-dimethoxytetrahydrofuran may be used in large excess so that it may serve as a solvent as well. Preferably, it is used in an amount of 0.8 to 15 equivalents. In some instances, when the reaction is carried out in the presence of an acid for the purpose of promoting the reaction and reducing the byproduct formation or when the starting material is treated with an acid prior to the reaction or the reaction mixture after the reaction is treated with an acid, favorable results can be obtained. Usable as such acid catalyst are inorganic protic acids such as hydrochloric acid, hydrobromic acid, hydroiodic acid, phosphoric acid and sulfuric acid; organic protic acids such as formic acid, acetic acid, tartaric acid, malic acid, citric acid, oxalic acid, succinic acid, benzoic acid, trifluoroacetic acid and p-toluenesulfonic acid; and Lewis acids such as aluminum chloride, ferric chloride, zinc chloride, titanium tetrachloride and boron trifluoride. The amount of such acid catalyst to be used in the reaction is not particularly restricted unless it adversely affects the reaction. The acid catalyst may be used in large excess so that it may serve as a solvent as well.

The reactions shown in the reaction schemes (B) to (J) may each be carried out in an appropriate solvent. Useful as such solvent are those mentioned above in reference to the reaction schema (A). The temperature to be employed in each of the reactions shown in the reaction schemes (B) to (J) is generally within the range of about −50° C. to 200° C., preferably about −30° C. to 150° C. The reaction time is generally within the range of about 0.1 to 96 hours, preferably about 0.1 to 72 hours, more preferably about 0.1 to 24 hours. The compounds respectively obtained by the reactions shown in the reaction schemes (B) to (J) can be isolated and purified by such per se known means as mentioned with reference to the reaction schema (A). They may be used as the starting materials in the next reaction either after such isolation/purification or in the reaction mixture form.

The compounds [I] or salts thereof are effective in preventing sanitary or horticultural insect pests and animal and plant parasites and can exert potent insecticidal activities when they are applied to harmed living animals or plants. Moreover, the compounds [I] and their salts possess safe and advantageous properties as agents for preventing sanitary, stockbreeding, pet-animal, horticultural or agricultural injurious insects, such as no substantial damage on plants and less toxicity against fishes.

The compounds [I] or salts thereof can be used as an agricultural chemical, particularly, insecticide in any application form suited for general agricultural chemicals. That is, one or two, or more than (preferably one to three) kinds of the compounds [I] or salts thereof are used in the form of preparation such as emulsifiable concentrates, liquid preparation, micro emulsion, flowable concentrates, oil solution, wettable powders, dusts, granules, fine granules, seed coating, smoking pesticides, tablets, microcapsule, sprays, EW, ointments, poisonous bait or the like, according to the purpose of use, by dissolving or dispersing them in suitable liquid carriers or mixing them with or adsorbing them on suitable solid carriers. These formulations may contain, if necessary, emulsifying agent, suspending agent, spreading agent, penetrating agent, wetting agent, thickening agent, stabilizer, etc., and can be prepared by any conventional method known per se., e.g. mixing each ingredient.

Suitable examples of the liquid carriers, include solvents such as water, alcohols (e.g. methanol, ethanol, n-propanol, iso-propanol or ethylene glycol), ketones (e.g. acetone or methyl ethyl ketone), ethers (e.g. dioxane, tetrahydrofuran, ethylene glycol monomethyl ether, diethylene glycol monomethyl ether or propylene glycol monomethyl ether), aliphatic hydrocarbons (e.g. kerosine, kerosine oil, fuel oil or machine oil), aromatic hydrocarbons (e.g. benzene, toluene, xylene, solvent naphtha or methylnaphthalene), halogenated hydrocarbons (e.g. dichloromethane, chloroform or carbon tetrachloride), acid amides (e.g. N,N-dimethylformamide or N,N-dimethylacetamide), esters (e.g. ethyl acetate, butyl acetate or fatty acid glycerol ester) or nitrites (e.g. acetonitrile or propionitrile). These solvents are used individually or as a suitable mixture of two or more (preferably one to three) of them.

Suitable examples of the solid carriers (diluents or dust carrier) include vegetable powder (e.g. soy-been meal, tobacco meal, wheat flour or wood flour), mineral powders (e.g. clays such as kaolin, bentonite, or acid clay; talcs such as talc powder or pyrophyllite powder; silicas such as diatomaceous earth or mica powder), aluminas, sulfur powder or activated charcoal. They are used individually or as a suitable mixture of two or more (preferably one to three) of them.

Also, suitable examples of bases for ointments include polyethylene glycol, pectin, polyalcohol esters of higher aliphatic acids (e.g. glycerin mono-stearate), cellulose derivatives (e.g. methyl cellulose), sodium alginate, bentonite, higher alcohols, polyalcohols (e.g. glycerin), vaseline, white vaseline, liquid paraffin, lard, various vegetable oils, lanolin, dehydrates lanolin, hard oil or resins. These are used individually, or as a suitable mixture of two or more (preferably one to three) of them or together with surface active agents mentioned below.

As surface active agents used as the emulsifying agent, spreading agent, penetrating agent or dispersing agent, nonionic or anionic surface active agents such as soaps; polyoxyethylene alkyl aryl ethers (e.g. Noigene® and EA 142® from Dai-ichi Kogyo Seiyaku K. K., Japan, and Nonal® from Toho Chemical, Japan); alkyl sulfates (e.g. Emal 10® and Emal 40® from Kao K. K., Japan), alkyl sulfonates (e.g. Neogen® and Neogen T® from Dai-ichi Kogyo Seiyaku K. K., and Neopellex® from Kao K. K.); polyethylene glycol ethers (e.g. Nonipol 85®, Nonipol 100® and Nonipol 160® from Sanyo Kasei K. K., Japan); or polyhydric alcohol estes (e.g., Tween 20® and Tween 800® from Kao K. K.) are used, if necessary.

The compounds [I] or salts thereof can also be used, as occasion demands, in combination with or as an admixture with other insecticides (for example, pyrethroid insecticides, organophosphorus insecticides, carbamate insecticides, neonicotinoid insecticides or natural insecticides), acaricides, nematicides, herbicides, plant hormones, plant growth regulators, fungicides (for example, copper fungicides, organic chloride fungicides, organic sulfur fungicides or phenolic fungicides), synergistic agents, attractants, repellents, pigments and/or fertilizers.

The amount of the compound [I] or a salt thereof contained in an agrocemical composition (an insecticidal composition) of the present invension is suitably about 0.1 to 80% by weight, preferably about 1 to 20% by weight, relative to the whole composition. Specifically, the amount is suitably about 1 to 80% by weight, preferably about 1 to 20% by weight in the case of emulsifiable concentrates, liquid preparations or wettable powders (e.g. granulated wettable powders); about 0.1 to 50% by weight, preferably about 0.1 to 20% by weight in the case of oil solution or dusts; about 5 to 50% by weight, preferably about 1 to 20% weight in the case of granules.

The other agricultural active ingredients (e.g. insecticide, herbicide, acaricide and/or fungicide) incorporated into the composition of the present invention may be used in an amount of about 1 to 80% by weight, preferably about 1 to 20% by weight, relative to the whole composition.

The amount of each of the additives other than the above-described active ingredients usually ranges, which varies depending on the variety and content of the agricultural active ingredient or the form of the composition, is usually about 0.001 to 99.9% by weight, preferably about 1 to 99% by weight, relative to the whole composition. More concretely, the surface active agent may be used in an amount of about 1 to 20% by weight, preferably about 1 to 15% by weight; the fluidizing agent may be used in an amount of about 1 to 20% by weight; and the carrier may be used in an amount of about 1 to 90% by weight, preferably about 1 to 70% by weight, relative to the whole composition. For example, the surface active agent may be used in an amount of about 1 to 20% by weight, preferably about 1 to 10% by weight and water may be used in rate of about 20 to 90% by weight in the case of liquid preparation. Emulsifiable concentrates, wettable powders (e.g. granulated wettable powders) or the like can be suitably diluted or extended (for example, to about 100 to 5,000 times) with water or the like, on the occasion of use, and then applied.

Typical examples of the insecticide, acaricide and fungicide which may be employed in admixture with the compound III or a salt thereof of the present invention will be given below:

EPN, acephate, isoxathion, isofenphos, isoprocarb, etrimfos, oxydeprofos, quinalphos, cadusafos, chlorethoxyfos, chlorpyrifos, chlorpyrifos-methyl, chlorofenvinphos, salithion, cyanophos, disulfoton, dimethoate, sulprofos, diazinon, thiometon, tetrachlorvinphos, tebupirimfos, trichlorphon, naled, vamidothion, pyraclophos, pyridafenthion, pirimiphos-methyl, fenitrothion, fenthion, phenthoate, fosthiazate, butathiofos, prothiofos, propaphos, profenofos, phosalone, fosthiazate, malathion, methidathion, metolcarb, monocrotophos, BPMC, XMC, alanycarb, ethiofencarb, carbaryl, carbosulfan, carbofuran, xylylcarb, cloethocarb, thiodicarb, triazamate, pirimicarb, fenoxycarb, fenothiocarb, furathiocarb, propoxur, bendiocarb, benfuracarb, methomyl, acrinathrin, imiprothrin, ethofenprox, cycloprothrin, sigma-cypermethrin, cyhalothrin, cyfluthrin, cypermethrin, silafluofen, tefluthrin, deltamethrin, tralomethrin, fenvalerate, fenpropathrin, flucythrinate, fluvalinate, flufenoprox, fluproxyfen, flumethrin, prallethrin, beta-cyfluthrin, benfluthrin, permethrin, acetamiprid, imidacloprid, cartap, thiocyclam, nitenpyram, clotianidine, tefuranidine, AKD-1022, thiomethoxam, bensultap, avermectin, emamectin-benzoate, clofentezine, chlorfluazuron, cyromazine, diafenthiuron, dienochlor, dichlorvos, diflubenzuron, spynosyn, sulfluramid, teflubenzuron, tebufenozide, tebufenpyrad, hydroprene, vaniliprole, pymetrozine, pyridaben, pyriproxyfen, pyrimidifen, fipronil, fenazaquin, fenpyroximate, fluazuron, flucycloxuron, flufenoxuron, buprofezin, hexaflumuron, hexythiazox, milbemycin, metoxadiazone, luf enuron, levamisol, chlorphenapyr, NC-184, etoxazole, IBP, ampropylfos, edifenphos, chlorthiophos, tolclofos-methyl, fosetyl, ipconazole, imazalil, imibenconazole, etaconazole, epoxiconazole, cyproconazole, diniconazole, difenoconazole, tetraconazole, tebuconazole, triadimenol, triadimefon, triticonazole, triforine, bitertanol, viniconazole, fenarimol, fenbuconazole, fluotrimazole, furconazole-cis, flusilazole, flutriafol,. bromuconazole, propiconazole, hexaconazole, pefurazoate, penconazole, myclobutanil, metconazole, cabendazin, debacarb, prothiocarb, benomyl, maneb, TPN, isoprothiolane, iprodione, iminoctadine-albesil, iminoctadine-triacetate, ethirimol, etridiazole, oxadixyl, oxycarboxin, oxolinic acid, ofurace, kasugamycin, carboxin, captan, clozylacon, chlobenthiazone, cyprodinil, cyprofuram, diethofencarb, dichlofluanid, diclomezine, zineb, dimethirimol, dimethomorph, dimefluazole, thiabendazole, thiophanate-methyl, thifluzamide, tecloftalam, triazoxide, triclamide, tricyclazole, tridemorph, triflumizole, validamycin A, hymexazol, pyracarbolid, pyrazophos, pyrifenox, pyrimethanil, pyroquilon, ferimzone, fenpiclonil, fenpropidin, fenpropimorph, fthalide, furametpyr, furalaxyl, fluazinam, furcarbanil, fluquinconazole, fludioxonil, flusulfamide, flutolanil, butiobate, prochloraz, procymidone, probenazole, benalaxyl, benodanil, pencycuron, myclozolin, metalaxyl, metsulfovax, methfuroxam, mepanipyrim, mepronil, kresoxim-methyl, azoxystrobin, SSF-126, carpropamid Specifically, the formulations containing the compound [I] or a salt thereof of the present invention are especially effective in preventing Hemiptera injurious insects such as *Eurydema rugosum, Scotinophara lurida, Riptortus clavatus, Stephanitis nashi, Laodelphax striatellus, Nilaparvata lugens, Nephotettix cincticeps, Unaspis yanonensis, Aphis glycines, Lipaphis erysimi, Brevicoryne brassicae, Aphis qossypii, Myzys persicae, Aulacorthum solani, Aphis spiraecola, Bemisia tabaci, Trialeurodes vaporariorum, Sogatella furcifera, Empoasca onukii, Pseudococcus comstocki, Planococcus citri, Icerya purchasi, Plautia stali, Eysarcoris parvus*; Lepidoptera injurious insects such as *Spodoptera litura, Plutella xylostella, Pieris rapae crucivora, Chilo suppressalis, Autographa nigrisigna, Helicoverpa assulta, Pseudaletia separate, Mamestra brassicae, Adoxophyes orana fasciata, Notarcha derogata, Cnaphalocrocis medinalis, Phthorimaea operculella, Chilo polychrysus, Tryporvza incertulas, Spodoptera exigua, Agrotis segetum, Agrotis ipsilon, Heliothis armiqera, Heliothis virescens, Heliothis zea, Naranga aenescens, Ostrinia nubilalis, Ostrinia furnacalis, Parnara Quttata, Adoxophyes sp., Caloptilia theivora, Phyllonorycter rinaoneella, Carposina niponensis, Gracholita molesta*; Coleoptera injurious insects such as *Elilachna vigintioctopunctata, Aulacophora femoralis, Phyllotreta striatata, Oulema orzae, Echinocnemus squameus, Lissorhoptrus oryzophilus, Anthonomus grandis, Callosobruchus chinensis, SDhenophorus venatus, Popillia japonica, Anomala cuprea,* Diabrotica spp., *Leptinotarsa decemlineata,* Aariotes spp., *Lasioderma serricorne, Anthrenus verbasci, Tribolium castaneum, Lyctus brunneus, Anoplophora malasiaca, Tomicus piniperda*; Diptera injurious insects such as *Musca domestica, Culex pipiens pallens, Tabanus triqonus, Delia antiqua, Delia platura, Anopheles sinensis, Agromvza oryzae, Hydrellia griseola, Chlorops oryzae, Dacus cucurbitae, Ceratitis capitata, Liriomyza trifolii*; Orthoptera injurious insects such as *Locusta migratoria, Gryllotalpa africana, Oxya yezoensis, Oxya laponica*; Thysanoptera injurious insects such as *Thrips tabaci, Thrips parmi, Frankliniella occidentalis, Baliothrips biformis, Scirtothrios dorsalis*; Hymenoptera injurious insects such as *Athalia rosae*; Dictyoptera injurious insects such as *Blattella germanica, Periplaneta fuliginosa, Periplaneta japonica, Periplaneta americana*; Tetranychidaes such as *Tetranychus urticae, Panonychus citri, Tetranychus kanzawai, Tetranychus cinnabarinus, Panonychus ulmi, Aculops pelekassi, Polyphagotarsonemus latus, Rhizoglyphus echinopus*; and Nematodes such as *Aphelenchoides besseyi, Meloidogyne incognita, Pratylenchus penetrans, Nothotylenchus acris*; Termites such as *Coptotermes formosanus, Resticulitermes speratus, Odontotermes formosanus, Cryptotermes domesticus*.

Further, the formulations containing the compound [I] or a salt thereof of the present invention are also effective in preventing or combatting arthropod or parasitic animals which parasites inside or outside of a vertebrate (e.g. human, cattle, sheep, goat, pig, fowl, dog, cat, fish, etc.) and in maintaining sanitary, in the field of therapeutics of diseases in livestock and stockbreeding. Such parasitic animals (parasite) include Ixodes spp., Boophilus spp. (e.g. *Boophilus microplus*), Amblyomma spp., Hyalomma spp., Rhipicephalus spp. (e.g. *Rhipicephalus appendiculatus*), Haemaphysalis spp., dermacentor spp., Ornithodoros spp. (e.g. *Ornithodoros moubata*), *Dermahyssus gallinae*, Sarcoptes spp.(e.g. *Sarcoptes scabiei*), Psoroptes spp., Chorioptes spp., Demodex spp., Eutrombicula spp., Aedes spp. Anopheles spp., Musca spp., Hypoderma spp., Gasterophilus spp., Simulium spp., Triatoma spp., Phthiraptera (e.g. Damalinia spp., Linognathus spp.), Ctenocephalides spp., monomorium pharaonis or Nematodes [e.g. Trichostrongylus such as *Nippostrongylus brasiliensis, Trichostrongylus axei* or *Trichostrongylus colubriformis*; Trichinella (e.g. *Trichinella spiralis*); Haemonchus contortus; Nematodirus (e.g. *Nematodirus battus*); *Ostertagia circumcincta*; Cooperia spp.; or *Hymenolepis nana*] etc.

The agrochemical composition which comprises a compound [I] or a salt thereof of the present invention can be used as excellent agrachemical composition (insecticidal composition) having excellent insecticidal effects, fairly low toxicity and good safety. It can be used in a similar way to the conventional insecticidal composition and can exert more excellent effects in comparison with the conventional composition. For example, occurred injurious insects as mentioned above can be prevented or combatted by applying the agrochemical composition of the present invention to a paddy field, plowland, orchard, non-cropland or house, according to per se known method, and contacting or ingesting to the injurious insects. As another embodiment of the present invention, arthropod or parasitic animals which parasites on a vertebrate can be prevented or combatted by administering the agrochemical composition to the inside (in the body) or the outside (on the surface of the body).

More specifically, the agrochemical composition of the present invention can be applied to the target insects, by seed treatment, nursery box treatment, planting hole treatment, planting foot treatment, soil treatment, foliar spray, infusion, poisonous bait, smoking, drenching, water application in paddy field. The amount of application may broadly vary depending on the season, place and method of application, and so forth. In general, the active ingredient (the compound [I] or a salt thereof) is used in amount of about 0.3 g to 3,000 g, preferably about 50 g to 1,000 g per hectare. When the agrochemical composition of the present invention is in a wettable powder, it can be used by diluting it so as to be about 0.1–1000 ppm, preferably about 10–500 ppm as the final concentration of the active ingredient.

EXAMPLE

The following reference examples, examples and test examples are further illustrative of the present invention.

In the column chromatographic purification procedure described in the examples and the reference examples, elutions were invariably carried out under TLC (thin-layer chromatography) monitoring. The TLC for monitoring was carried out using Merck's kieselgel 60F254 (70–230 mesh) as the TLC plate coating, the same solvent as the column chromatographic eluent for development, and a UV detector for detection. As the silica gel column packing, the same Merck's kieselgel 60 (70–230 mesh) was used. The NMR spectra are proton NMR spectra as recorded with Bruker AC-200P (200 MHz) spectrometer using tetramethylsilane as the internal standard and the δ values are shown in ppm. In cases where a mixed solvent was used as the eluent, the blending ratio of constituent solvents is shown in parentheses. The abbreviations used in the examples and the reference examples and in the tables have the following meanings. Me: methyl, Et: ethyl, Ph: phenyl, pr-n (or n-Pr): n-propyl, Pr-i (or i-Pr or $^i$Pr): isopropyl, Bu-n (or n-Bu): n-butyl, Bu-i (or i-Bu): isobutyl, Bu-s (or s-Bu): sec-butyl, Bu-t (or t-Bu): tert-butyl, s: singlet, br: broad, brs: broad singlet, d: doublet, t: triplet, q: quartet, qu: quintet, sep: septet, m: multiplet, dd: double doublet, dt: double triplet, J: coupling constant, Hz: Hertz, %: weight %, mp: melting point. Room temperature means about 15–25° C.

Reference Example 1

1-(2,6-Dichloro-4-trifluoromethylphenyl)-5-ethoxymethyleneamino-3-($\Delta^2$-1,2,4-oxadiazolin-3-yl)-4-trifluoromethylsulfinylpyrazole In 315 ml (1.89 nmuol) of triethyl orthoformate was dissolved 31.6 g (65.4 mmol) of 5-amino-1-(2,6-dichloro-4-trifluoromethylphenyl)-3-($\Delta^2$-1,2,4-oxadiazolin-3-yl)-4-trifluoromethylsulfinylpyrazole followed by addition of 1.25 g (6.54 mmol) of p-toluenesulfonic acid monohydrate, and the mixture was stirred at 40° C. for 4 hours. After this reaction, the triethyl orthoformate was distilled off under reduced pressure and the residue was triturated well in a small amount of n-hexane-chloroform and the resulting crystals were collected by filtration and dried to provide 7.94 g (14.8 mmol) of 1-(2,6-dichloro-4-trifluoromethylphenyl)-5-ethoxymethyleneamino-3-($\Delta^2$-1,2,4-oxadiazolin-3-yl)-4-trifluoromethylsulfinylpyrazole as colorless crystals. The filtrate was concentrated, and after addition of 200 ml of acetonitrile, 50 ml of water and 0.5 ml of 1.2N-hydrochloric acid, the mixture was allowed to stand at room temperature for 30 minutes. This reaction mixture was concentrated under reduced pressure and the residue was triturated well in n-hexane-acetone. The resulting crystals were collected by filtration and dried to recover additional 21.1 g (39.2 mmol) of 1-(2,6-dichloro-4-trifluoromethylphenyl)-5-ethoxymethyleneamino-3-($\Delta^2$-1,2,4-oxadiazolin-3-yl)-4-trifluoromethylsulfinylpyrazole.

yeild: 82% mp. 186–187° C.

NMR(CDCl$_3$, δ) 1.20 (3H,t,J=7 Hz), 4.08 (2H,m), 5.21 (1H,br), 5.44 (1H,s), 5.49 (1H,s), 7.75 (1H,s), 7.76 (1H,s), 8.50 (1H,br)

The following compounds were synthesized in substantially the same manner as above. 1-(2,6-Dichloro-4-trifluoromethylphenyl)-3-($\Delta^2$-1,2,4-oxadiazolin-3-yl)-5-(n-propoxymethyleneamino)-4-trifluoromethylthiopyrazole mp. 106–107° C.

1-(2,6-Dichloro-4-trifluoromethylphenyl)-3-($\Delta^2$-1,2,4-oxadiazolin-3-yl)-5-(n-propoxymethyleneamino)-4-trifluorometylsulfonylpyrazole mp. 111–112° C.

Reference Example 2

5-Amino-1-(2,6-dichloro-4-trifluoromethylphenyl)-3-(N$^1$-ethyl-N$^2$-hydroxyamidino)-4-trifluoromethylsulfinylpyrazole In 100 ml of THF was dissolved 10.1 g (20.5 mmol) of 5-amino-1-(2,6-dichloro-4-trifluoromethylphenyl)-3-(5-methyl-1,2,4-oxadiazol-3-yl)-4-trifluoromethylsulfinylpyrazole followed by addition of 5.58 g (40.9 mmol) of zinc chloride and 1.76 g (41.9 mmol) of sodium borohydride. The mixture was stirred at room temperature for 5 days and then poured in 150 ml of water. To this reaction mixture was added 100 ml of ethyl acetate, and the resulting precipitate was collected by filtration to be removed with the aid of Celite. The filtrate was washed with 100 ml of saturated aqueous solution of sodium chloride twice and dried over anhydrous magnesium sulfate and the solvent was then distilled off to provide yellowish brown amorphous powder. This crude product was subjected to silica gel column chromatography (ethyl acetate:hexane=1:2) to provide 6.45 g (13.0 mml) of 5-amino-1-(2,6-dichloro-4-trifluoromethylphenyl)-3-(N$^1$-ethyl-N$^2$-hydroxyamidino)-4-trifluoromethylsulfinylpyrazole as light-yellow amorphous powder.

yield: 63%

NMR(CDCl$_3$, δ) 1.15 (3H,t,J=7 Hz), 3.47–3.62 (2H,m), 5.07 (1H,t,J=6.3 Hz), 5.14 .(2H,br), 7.24 (1H,br), 7.80 (2H,s)

Reference Example 3

1-(2,6-Dichloro-4-trifluoromethylphenyl)-5-dimethylaminomethyleneamino-3-($\Delta^2$-1,2,4-oxadiazolin-3-yl)-4-trifluoromethylsulfinylpyrazole To 10 ml of toluene was added 0.91 g (1.89 mmol) of 5-amrino-1-(2, 6-dichloro-4-trifluoromethylphenyl)-3-($\Delta^2$-1,2,4-oxadiazolin-3-yl)-4-trifluoromethylsulfinylpyrazole followed by addition of 0.56 ml of N,N-dimethylformamide-dimethyl acetal (purity 90%; 3.79 mmol), and the mixture was stirred at 80 for 4 hours. The solvent was then distilled off and the residual colorless oil was subjected to silica gel column chromatography (ethyl acetate:chloroform=1:10). The crystals obtained were recrystallized from chloroform-hexane to provide 0.56 g (1.03 mmol) of 1-(2,6-dichloro-4-trifluoromethylphenyl)-5-dimethylaminomethyleneamino-3-($\Delta^2$-1,2,4-oxadiazolin-3-yl)-4-trifluoromethylsulfinylpyrazole as colorless crystals.

yield: 55% mp. 171–173° C.

NMR(CDCl$_3$, δ) 2.79 (3H,s), 3.08 (3H,s), 5.24 (br,1H), 5.41 (1H,dd,J=1 Hz,3 Hz,), 5.47 (1H,dd,J=1 Hz,3 Hz), 7.70–7.74 (2H,m), 8.56(1H,s)

Example 1
5-Amino-1-(2,6-dichloro-4-trifluoromethylphenyl)-3-(4-diisopropoxymethyl-$\Delta^2$-1,2,4-oxadiazolin-3-yl)-4-trifluoromethylsulfonylpyrazole In 5 ml of truisopropyl orthoformate was dissolved 1.00 g (2.01 mmol) of 5-amino-1-(2,6-dichloro-4-trifluoromethylphenyl)-3-($\Delta^2$-1,2,4-oxadiazolin-3-yl)-4-trifluoromethylsulfonylpyrazole, and following addition of 20 mg of p-toluenesulfonic acid monohydrate, the mixture was stirred at 90° C. for 34 hours. This reaction mixture was subjected to silica gel column chromatography (n-hexane:acetone=5:1) to provide light-yellow crystals. This crystal crop was recrystallized from petroleum ether-acetone to provide 360 mg (0.57 mmol) of 5-amino-1-(2,6-dichloro-4-trifluoromethylphenyl)-3-(4-diisopropoxymethyl-$\Delta^2$-1,2,4-oxadiazolin-3-yl)-4-trifluoromethylsulfonylpyrazole as colorless crystals.

yield: 29% mp. 173–176° C.

NMR(CDCl$_3$+DMSO-d$_6$, δ) 1.10 (6H,d,J=6 Hz), 1.11 (6H,d,J=6 Hz), 3.85 (2H,sep,J=6 Hz), 5.54 (2H,s), 5.66 (1H,s), 6.58 (2H,br), 7.80 (2H,d,J=0.5 Hz)

Example 2
3-(4-Acetyl-$\Delta^2$-1,2,4-oxadiazolin-3-yl)-1-(2,6-dichloro-4-trifluoromethylphenyl)-5-methoxymethyleneamino-4-trifluoromethylsulfinylpyrazole In 10 ml of acetonitrile was suspended 520 mg (1.00 mmol) of 1-(2,6-dichloro-4-trifluoromethylphenyl)-5-methoxymethyleneamino-3-($\Delta^2$-1,2,4-oxadiazolin-3-yl)-4-trifluoromethylsulfinylpyrazole. Then, 82 mg (1.04 mmol) of pyridine was added to the suspension and a solution of acetic anhydride (106 mg, 1.04 mmol) in acetonitrile (5 ml) was added dropwise at room temperature. The mixture was stirred at room temperature for 18 hours. Then, 127 mg (1.04 mmol) of 4-dimethylaminopyridine was added and the reaction mixture was further stirred at room temperature for 5 hours. This reaction mixture was concentrated under reduced pressure and the residue was subjected to silica gel column chromatography (n-hexane:ethyl acetate=5:1) to provide 530 mg of colorless crystals. This crystal crop was recrystallized from ethyl acetate-n-hexane to provide 400 mg (0.70 mmol) of 3-(4-acetyl-$\Delta^2$-1,2,4-oxadiazolin-3-yl)-1-(2,6-dichloro-4-trifluoromethylphenyl)-5-methoxymethyleneamino-4-trifluoromethylsulfinylpyrazole as colorless crystals.

yield: 70% mp. 126–127° C.

NMR(CDCl$_3$, δ) 2.14 (3H,s), 3.70 (3H,s), 5.82 (1H,d,J=3 Hz), 6.01 (1H,d,J=3 Hz), 7.78 (2H,m), 8.64 (1H,s)

Example 3
1-(2,6-Dichloro-4-trifluoromethylphenyl)-5-ethoxymethyleneamino-3-(4-propionyl-$\Delta^2$-1,2,4-oxadiazolin-3-yl)-4-trifluoromethylsulfinylpyrazole In 10 ml of acetonitrile was suspended 550 mg (1.02 mmol) of 1-(2,6-dichloro-4-trifluoromethylphenyl)-5-ethoxymethyleneamino-3-($\Delta^2$-1,2,4-oxadiazolin-3-yl)-4-trifluoromethylsulfinylpyrazole. To this suspension, 0.09 ml (1.23 mmol) of pyridine, 0.157 ml (1.23 mmol) of propionic anhydride and 150 mg (1.23 mmol) of 4-dimethylaminopyridine (DMAP) were added and the mixture was stirred at room temperature for 4 hours. This reaction mixture was concentrated under reduced pressure and the residue was subjected to silica gel column chromatography (n-hexane:ethyl acetate=2:1) to give colorless liquid. This liquid was crystallized from isopropyl ether-petroleum ether to provide 440 mg (0.74 mmol) of 1-(2,6-dichloro-4-trifluoromethylphenyl)-5-ethoxymethyleneamino-3-(4-propionyl-$\Delta^2$-1,2,4-oxadiazolin-3-yl)-4-trifluoromethylsulfinylpyrazole as colorless crystals.

yield: 72% mp. 114–115° C.

NMR(CDCl$_3$, δ) 1.07 (3H,t, J=7 Hz), 1.22 (3H,t,J=7 Hz), 2.37 (2H,m), 4.12 (2H,m), 5.81 (1H,d,J=3 Hz), 6.02 (1H,d, J=3 Hz), 7.76 (2H,m), 8.61 (1H,s)

Example 4
1-(2,6-Dichloro-4-trifluoromethylphenyl)-5-ethoxymethyleneamino-3-(4-methylcarbamoyl-$\Delta^2$-1,2,4-oxadiazolin-3-yl)-4-trifluoromethylsulfinylpyrazole In 10 ml of acetonitrile was suspended 550 mg (1.02 mmol) of 1-(2,6-dichloro-4-trifluoromethylphenyl)-5-ethoxymethyleneamino-3-($\Delta^2$-1,2,4-oxadiazolin-3-yl)-4-trifluoromethylsulfinylpyrazole. Then, 0.124 ml (2.04 mmol) of methyl isocyanate was added to the above suspension and the mixture was stirred at room temperature for 45 hours. To this reaction mixture, 0.285 ml (2.04 mmol) of triethylamine and 0.124 ml (2.04 mmol) of methyl isocyanate were further added and the mixture was stirred at room temperature for additional 24 hours. This reaction mixture was concentrated under reduced pressure and the residue was subjected to silica gel column chromatography (n-hexane:ethyl acetate=2:1) to give light-yellow liquid. This liquid was crystallized from ethyl acetate-petroleum ether to provide 370 mg (0.62 mmol) of 1-(2,6-dichloro-4-trifluoromethylphenyl)-5-ethoxymethyleneamino-3-(4-methylcarbamoyl-$\Delta^2$-1,2,4-oxadiazolin-3-yl)-4-trifluoromethylsulfinylpyrazole as colorless crystals.

yield: 61% mp. 115–116° C.

NMR(CDCl$_3$, δ) 1.21 (3H,t,J=7 Hz), 2.75 (3H,d,J=5 Hz), 4.11 (2H,m), 5.83 (1H,d,J=2 Hz), 6.13 (1H,d,J=2 Hz,), 7.22 (1H,m), 7.80 (2H,m), 8.56 (1H,s)

Example 5
1-(2,6-Dichloro-4-trifluoromethylphenyl)-3-(4-diethylcarbamoyl-$^2$-1,2,4-oxadiazolin-3-yl)-5-ethoxymethyleneamino-4-trifluoromethylsulfinylpyrazole In 5 ml of tetrahydrofuran (THF) was dissolved 56.2 mg (0.189 mmol) of bis(trichloromethyl) carbonate (BTC) followed by cooling on ice. To this cooled solution was added 0.0496 ml (0.613 mmol) of pyridine, and the mixture was stirred at room temperature for I hour. Then, a solution of 300 mg (0.557 mmol) of 1-(2,6-dichloro-4-trifluoromethylphenyl)-5-ethoxymethyleneamino-3-($\Delta^2$-1,2,4-oxadiazolin-3-yl)-4-trifluoromethylsulfinylpyrazole in 5 ml of THF was added dropwise over 5 minutes to the above mixture under ice-cooling and the mixture was stirred at room temperature for 1 hour. Thereafter, 0.115 ml (1.11 mmol) of diethylamine was added and the mixture was stirred at room temperature for 6 hours. The crystals formed were filtered off and the filtrate was concentrated under reduced pressure and subjected to silica gel column chromatography (n-hexane:ethyl acetate=3:1) to provide 220 mg (0.34 mmol) of 1-(2,6-dichloro-4-trifluoromethylphenyl)-3-($\Delta^2$-4-diethylcarbamoyl-1,2,4-oxadiazolin-3-yl)-5-ethoxymethyleneamino-4-trifluoromethylsulfinylpyrazole as colorless crystals.

yield: 62% mp. 107–108° C.

NMR(CDCl$_3$, δ) 1.14 (6H,t,J=7 Hz), 1.19 (3H,t,J=7 Hz), 3.30 (4H,q,J=7 Hz), 4.08 (2H,m), 5.48 (1H,d,J=1 Hz), 5.55 (1H,d,J=1 Hz), 7.72 (2H,m), 8.58 (1H,s)

Example 6
1-(2,6-Dichloro-4-trifluoromethylphenyl)-3-(4-dimethylaminoacetyl-$\Delta^2$-1,2,4-oxadiazolin-3-yl)-5-ethoxymethyleneamino-4-trifluoromethylsulfinylpyrazole In 10 ml of acetonitrile was suspended 500 mg (0.93 mmol) of 1-(2,6-dichloro-4-trifluoromethylphenyl)-5-ethoxymethyleneamino-3-($\Delta^2$-i,2,4-oxadiazolin-3-yl)-4-trifluoromethylsulfinylpyrazole. To this suspension, 127 mg (0.93 mmol) of N,N-dimethylglycine hydrochloride, 410 mg (0.93 mmol) of BOP reagent and 0.26 ml (1.86 mmol) of triethylamine were added, and the mixture was stirred at room temperature for 55 hours. This reaction mixture was concentrated under reduced pressure and the residue was subjected to silica gel column chromatography (n-hexane:ethyl acetate=2:1) to give 270 mg of colorless crystals. This crystal crop was recrystallized from propyl ether-hexane to provide 150 mg (0.24 mmol) of 1-(2,6-dichloro-4-trifluoromethylphenyl)-3-(4-dimethylaminoacetyl-$\Delta^2$-1,2,4-oxadiazolin-3-yl)-5-ethoxymethyleneamino-4-trifluoromethylsulfinylpyrazole as colorless crystals.

yield: 26%
mp. 135° C.
NMR(CDCl$_3$, δ) 1.22 (3H,t,J=7 Hz), 2.11 (6H,s), 2.95 (1H,d,J=14 Hz), 3.40 (1H,d,J=14 Hz), 4.11 (m,2H), 5.60 (1H,d,J=4 Hz), 6.11 (1H,d,J=4 Hz), 7.76 (2H,m), 8.72 (1H,s)

Example 7
5-Amimo-1-(2,6-dichloro-4-trifluoromethylphenyl)-3-(4-ethyl-$\Delta^2$-1,2,4-oxadiazolin-3-yl)-4-trifluoromethylsulfinylpyrazole In 15 ml of acetonitrile was dissolved 1.0 g (2.0 mmol) of 5-amino-1-(2,6-dichloro-4-trifluoromethylphenyl)-3-(N$^1$-ethyl-N$^2$-hydroxyamidino)-4-trifluoromethylsulfinylpyrazole. After addition of 0.8 ml (11 mmol) of 37% formalin and 3 drops of acetic acid, the mixture was refluxed for 7 hours. Thereafter, 60 ml of ethyl acetate was added and the reaction mixture was washed serially with 40 ml of saturated aqueous sodium hydrogen carbonate solution (x3) and 20 ml of saturated aqueous sodium chloride solution (x2) and dried over anhydrous magnesium sulfate. The solvent was then distilled off to give light-yellow amorphous powder. The powder was purified by silica gel column chromatography (n-hexane:ethyl acetate=3:1) to provide 500 mg (0.98 mmol) of 5-amino-1-(2,6-dichloro-4-trifluoro-methylphenyl)-3-(4-ethyl-$\Delta^2$-1,2,4-oxadiazolin-3-yl)-4-trifluoromethylsulfinylpyrazole as colorless amorphous powder.

yield: 49%
NMR (CDCl$_3$, δ) 1.14 (3H,t,J=7 Hz), 3.4–3.7 (2H,m), 5.18 (2H,br), 5.38 (2H,d,J=7 Hz), 7.82 (2H,s)

Example 8
3-(4-Acetyl-$\Delta^2$-1,2,4-oxadiazolin-3-yl)-1-(2,6-dichloro-4-trifluoromethylphenyl)-5-ethoxymethyleneamino-4-trifluoromethylsulfinylpyrazole In 10 ml of acetonitrile was dissolved 0.89 g (1.7 mmol) of 1-(2,6-dichloro-4-trifluoromethylphenyl)-5-ethoxymethyleneamino-3-($\Delta^2$-1,2,4-oxadiazolin-3-yl)-4-trifluoromethylsulfinylpyrazole. After addition of 0.21 g (1.72 mmol) of 4-dimethylaminopyridine and 0.16 ml (1.7 mmol) of acetic anhydride, the mixture was stirred at room temperature for 2.5 hours. After completion of the reaction, the solvent was distilled off and 70 ml of ethyl acetate was added to the residue. This mixture was washed serially with 20 ml of saturated aqueous sodium hydrogen carbonate solution (x2) and 30 ml of saturated aqueous sodium chloride solution (x2) and dried over anhydrous magnesium sulfate, and the solvent was then distilled off to recover light-yellow amorphous powder. The powder was purified by silica gel column chromatography (n-hexane:ethyl acetate=2:1) and the resulting colorless crystals were recrystallized from chloroform-n-hexane to provide 160 mg (0.27 mmol) of 3-(4-acetyl-$\Delta^2$-1,2,4-oxadiazolin-3-yl)-1-(2,6-dichloro-4-trifluoromethylphenyl)-5-ethoxymethyleneamino-4-trifluoromethylsulfinylpyrazole as colorless crystals.

yield: 16%
mp. 116–118° C.
NMR (CDCl$_3$, δ) 1.22 (3H,t,J=7 Hz), 2.14 (3H,s), 4.20–4.25 (2H,m), 5.83 (1H,d,J=3 Hz), 6.01 (1H,d,J=3 Hz), 7.76–7.80 (2H,m), 8.60 (1H,s)

Example 9
5-Amino-1-(2,6-dichloro-4-trifluoromethylphenyl)-3-{4-(N,N-diethylcarbamoyl)-$\Delta^2$-1,2,4-oxadiazolin-3-yl}-4 trifluoromethylthiopyrazole In 6 ml of THF was dissolved 318 mg (1.07 mmol) of bis(trichloromethyl) carbonate (BTC) followed by cooling on ice. To this solution was added 255 mg (3.22 mmol) of pyridine, and the mixture was stirred at room temperature for 30 minutes. To this reaction mixture, a solution of 1.00 g (2.15 mmol) of 5-amino-1-(2,6-dichloro-4-trifluoromethylphenyl)-3-($\Delta^2$-1,2,4-oxadiazolin-3-yl)-4-trifluoromethylthiopyrazole in 6 ml of THF was added dropwise under ice-cooling and the mixture was stirred at the same temperature for 30 minutes. After completion of the reaction, 472 mg (6.45 mmol) of diethylamine was added and the mixture was stirred under ice-cooling for 3 hours and then at room temperature for 3 hours. This reaction mixture was poured in 100 ml of iced water and extracted with 100 ml of ethyl acetate. The extract was dried over anhydrous magnesium sulfate and concentrated and the residue was subjected to silica gel column chromatography (n-hexane:ethyl acetate=1:1) to provide 370 mg (0.65 mmol) of the title compound as colorless crystals.

yield: 30%
mp. 81–83° C.
NMR (CDCl$_3$, δ) 1.16 (6H,t,J=7 Hz), 3.30 (4H,q,J=7 Hz), 4.34 (2H,s),5.51 (2H,s), 7.76 (2H,s)

Example 10
1-(2,6-Dichloro-4-trifluoromethylphenyl)-3-(4-(N,N-diethylcarbamoyl)-$\Delta^2$-1,2,4-oxadiazolin-3-yl)-5-ethoxymethyleneamino-4-trifluoromethylthiopyrazole In 3 ml of triethyl orthoformate was dissolved 370 mg (0.65 mmol) of 5-amino-1-(2,6-dichloro-4-trifluoromethylphenyl)-3-{4-(N,N-diethylcarbamoyl)-$\Delta^2$-1,2,4-oxadiazolin-3-yl}-4-trifluoromethylthiopyrazole. To this solution was added 50 mg of p-toluenesulfonic acid monohydrate, and the mixture was stirred at room temperature for 3 hours. This reaction mixture was concentrated under reduced pressure and the residue was subjected to silica gel column chromatography (n-hexane:ethyl acetate=2:1) to provide 290 mg (0.47 mmol) of the title compound as colorless crystals.

yield: 72%
mp. 93–95° C.
NMR (CDCl$_3$, δ) 1.26–1.14 (9H,m), 3.30 (4H,q,J=7 Hz), 4.13 (2H,q,J=7 Hz), 5.55 (2H,s), 7.70 (2H,s), 8.33 (1H,s)

Example 11
5-Amino-1-(2,6-dichloro-4-trifluoromethylphenyl)-3-(4-(N,N-dimethylcarbamoyl)-$\Delta^2$-1,2,4-oxadiazolin-3-yl)-4-trifluoromethylsulfinylpyrazole In 12 ml of THF was dissolved 615 mg (2.07 mmol) of bis(trichloromethyl) carbonate (BTC) followed by cooling on ice. To this solution was added 492 mg (6.22 mmol) of pyridine, and the mixture was stirred at room temperature for 30 minutes. Then, a solution of 2.00 9 (4.15 mmol) of 5-amino-1-(2,6-dichloro-4-trifluoromethylphenyl)-3-($\Delta^2$-1,2,4-oxadiazolin-3-yl)-4-trifluoromethylsulfinylpyrazole in 12 ml of THF was added dropwise to the above mixture under ice-cooling and the whole mixture was stirred at the same temperature for 30 minutes. Thereafter, 1.12 g (12.4 mmol) of 50% dimethylamine/water was added and the mixture was stirred under ice-cooling for 1 hour. This reaction mixture was poured in 100 ml of iced water and extracted with 100 ml of ethyl acetate. The extract was dried over anhydrous magnesium sulfate and concentrated to provide 2.26 g (4.08 mmol) of the title compound as colorless crystals.

yield: 98% mp. 207.0–207.5° C.

NMR (CDCl$_3$, δ) 2.93 (6H,s), 5.14 (2H,s), 5.46 (1H,d,J=2 Hz), 5.52 (1H,d,J=2 Hz), 7.78 (2H,s)

Example 12

5-Amino-1-(2,6-dichloro-4-trifluoromethylphenyl)-3-{4-(N,N-diethylcarbamoyl)-$\Delta^2$-1,2,4-oxadiazolin-3-yl}-4-trifluordmethylsulfinylpyrazole In 10 ml of THF was dissolved 113 mg (0.38 mmol) of bis(trichloromethyl) carbonate (BTC) followed by cooling on ice. To this solution was added 0.0923 ml (1.14 mmol) of pyridine, and the mixture was stirred at room temperature for 30 minutes. Then, a solution of 500 mg (1.04 mmol) of 5-amino-1-(2,6-dichloro-4-trifluoromethylphenyl)-3-($\Delta^2$-1,2,4-oxadiazolin-3-yl)-4-trifluoromethylsulfinylpyrazole in 5 ml of THF was added dropwise to the above mixture under ice-cooling and the whole mixture was stirred at room temperature for 1 hour. After completion of the reaction, 0.322 ml (3.11 mmol) of diethylamine was added and the mixture was stirred at room temperature for 15.5 hours. The precipitated crystals were filtered off and the filtrate was concentrated under reduced pressure. The residue was subjected to silica gel column chromatography (n-hexane:ethyl acetate=2:1) to give colorless crystals. This crystal crop was recrystallized from n-hexane-ethyl acetate to provide 260 mg (0.45 mmol) of the title compound as colorless crystals.

yield: 43% mp. 98.0–99.0° C.

NMR (CDCl$_3$, δ) 1.13 (6H,t,J=7 Hz), 3.30 (4H,q,J=7 Hz), 5.1 3 (2H,s), 5.43(1H,d,J=1 Hz), 5.50 (1H,d,J=1 Hz),7.78 (2H, s)

Example 13

1-(2,6-Dichloro-4-trifluoromethylphenyl)-3-{4-(N,N-diethylcarbamoyl)-$\Delta^2$-1,2,4-oxadiazolin-3-yl}-5-ethoxymethyleneamino-4-trifluoromethylsulfonylpyrazole In 10 ml of THF was dissolved 119 mg (0.401 mmol) of bis(trichloromethyl) carbonate (BTC) followed by cooling on ice. To this solution was added 0.0974 ml (1.20 mmol) of pyridine. Then, a solution of 400 mg (0.803 mmol) of 1-(2,6-dichloro-4-trifluoromethylphenyl)-5-ethoxymethyleneamino-3-($\Delta^2$-1,2,4-oxadiazolin-3-yl)-4-trifluoromethylsulfonylpyrazole in 5 ml of THF was added dropwise under ice-cooling and the mixture was stirred at the same temperature for 2 hours. After completion of the reaction, 0.332 ml (3.21 mmol) of diethylamine dissolved in 5 ml of THF was added and the mixture was stirred at room temperature for 30 minutes. This reaction mixture was concentrated under reduced pressure and the residue was subjected to silica gel column chromatography (n-hexane:ethyl acetate=1:1) to provide 130 mg (0.20 mmol) of the title compound as colorless crystals.

yield: 25% mp. 105.5–106.5° C.

NMR (CDCl$_3$, δ) 1.17 (6H,t,J=7 Hz), 1.23 (3H,t,J=6 Hz), 3.2 7 (4H,q,J=7 Hz),4.16 (2H,q,J=6 Hz), 5.64 (2H,s), 7.74 (2H, s), 8.04 (1H,s)

Example 14

1-(2,6-Dichloro-4-trifluoromethylphenyl)-3-{4-(N,N-dimethylcarbamoyl)-$\Delta^2$-1,2,4-oxadiazolin-3-yl}-5-ethoxymethyleneamino-4-trifluoromethylsulfinylpyrazole In 5 ml of THF was dissolved 91.2 mg (0.310 mmol) of bis(trichloromethyl) carbonate (BTC) followed by cooling on ice. To this solution was added 0.0751 ml (0.929 mmol) of pyridine, and the mixture was stirred at room temperature for 1 hour. Then, a solution of 500 mg (0.929 mmol) of 1-(2,6-dichloro-4-trifluoromethylphenyl)-5-ethoxymethyleneamino-3-($\Delta^2$-1,2,4-oxadiazolin-3-yl)-4-trifluoromethylsulfinylpyrazole in 5 ml of THF was added dropwise under ice-cooling and the mixture was stirred at room temperature for 1 hour. After completion of the reaction, 0.167 ml (1.86 mmol) of 50% dimethylamine/water, dissolved in 5 ml of THF beforehand, was added dropwise and the mixture was stirred at room temperature for 3.5 hours. This reaction mixture was concentrated under reduced pressure and the residue was subjected to silica gel column chromatography (n-hexane:ethyl acetate=2:1) to provide 210 mg (0.34 mmol) of the title compound as colorless amorphous powder.

yield: 37%

NMR(CDCl$_3$, δ) 1.20 (3H,t,J=7 Hz), 2.94 (6H,s), 4.10 (2H, nm), 5.51 (1H,d,J=2 Hz), 5.58 (1H,d,J=2 Hz), 7.72 (2H,m), 8. 56 (1H,s)

Example 15

1-(2,6-Dichloro-4-trifluoromethylphenyl)-3-(4-(N-ethyl-N-methylcarbamoyl)-$\Delta^2$-1,2,4-oxadiazolin-3-yl)-5-ethoxymethyleneamino-4-trifluoromethylsulfinylpyrazole In 3 ml of THF was dissolved 138 mg (0.47 mmol) of bis(trichloromethyl) carbonate (BTC) followed by cooling on ice. To this solution was added 111 mg (1.40 mmol) of pyridine, and the mixture was stirred under ice-cooling for 0.5 hours. Then, a solution of 500 mg (0.93 mmol) of 1-(2,6-dichloro-4-trifluoromethylphenyl)-5-ethoxymethyleneamino-3-($\Delta^2$-1,2,4-oxadiazolin-3-yl)-4-trifluoromethylsulfinylpyrazole in 3 ml of THF was added dropwise under ice-cooling and the mixture was stirred at the same temperature for 0.5 hours. After completion of the reaction, 110 mg (1.86 mmol) of ethylmethylamine, dissolved in 1 ml of THF beforehand, was added dropwise and the mixture was stirred at room temperature for 21 hours. This reaction mixture was poured in 100 ml of iced water and extracted with 100 ml of ethyl acetate. The extract was dried over anhydrous magnesium sulfate and concentrated and the residue was subjected to silica gel column chromatography (n-hexane:ethyl acetate=3:1) to provide 100 mg (0.16 mmol) of the title compound as colorless amorphous powder.

yield: 17% mp. 113–114° C.

NMR (CDCl$_3$, δ) 1.14 (3H,t,J=7 Hz), 1.20 (3H,t,J=7 Hz), 2.93 (3H,s), 3.31(2H,q,J=7 Hz), 4.30–3.90 (2H,m), 5.50 (1H,s), 5.57 (1H,s),7.72 (2H,s), 8.58 (1H,s)

Example 16
1-(2,6-Dichloro-4-trifluoromethylphenyl)-3-{4-(N,N-diethylcarbamoyl)-$\Delta^2$-1,2,4-oxadiazolin-3-yl)-5-isopropoxymethyleneamino-4-trifluoromethylsulfinylpyrazole In 10 ml of THF was dissolved 85.3 mg (0.287 mmol) of bis(trichloromethyl) carbonate (BTC) followed by cooling on ice. To this solution was added 0.0769 ml (0.951 mmol) of pyridine dropwise. Then, a solution of 500 mg (0.905 mmol) of 1-(2,6-dichloro-4-trifluoromethylphenyl)-5-isopropoxymethyleneamino-3-($\Delta^2$-1,2,4-oxadiazolin-3-yl)-4-trifluoromethylsulfinylpyrazole in 5 ml of THF was added dropwise under ice-cooling and the mixture was stirred at the room temperature for 1 hour. Then, under ice-cooling, a solution of 0.192 ml (1.86 mmol) of diethylamine in 5 ml of THF was added dropwise and the mixture was stirred at room temperature for 22.5 hours. This reaction mixture was concentrated under reduced pressure and the residue was subjected to silica gel column chromatography (n-hexane:ethyl acetate=2:1) to provide 240 mg (0.37 mmol) of the title compound as colorless liquid.

yield: 41%

NMR (CDCl$_3$, δ) 0.82 (3H,t,J=7 Hz), 1.14 (6H,t,J=7 Hz), 1.5 8 (2H,m), 3.30(4H,q,J=7 Hz), 3.99 (2H,m), 5.48 (1H,d, J=1 H z), 5.55 (1H,d,J=1 Hz), 7.72 (2H,m), 8.61 (1H,s)

Example 17
1-(2,6-Dichloro-4-trifluoromethylphenyl)-5-ethoxymethyleneamino-3-{4-pivaloyl-$\Delta^2$-1,2,4-oxadiazolin-3-yl}-4-trifluoromethylsulfinylpyrazole In 10 ml of acetonitrile was suspended 500 mg (0.929 mmol) of 1-(2, 6-dichloro-4-trifluoromethylphenyl)-5-ethoxymethyleneamino-3-($\Delta^2$-1,2,4-oxadiazolin-3-yl)-4-trifluoromethylsulfinylpyrazole. To this suspension, 0.142 ml (1.02 mmol) of triethylamine, 0.166 ml (1.02 mmol) of pivaloyl chloride and 5 mg of 4-dimethylaminopyridine were added, and the mixture was stirred at room temperature for 4 days. This reaction mixture was concentrated under reduced pressure and the residue was subjected to silica gel column chromatography (n-hexane:ethyl acetate=3:1) to provide 220 mg (0.35 mmol) of the title compound as colorless crystals.

yield: 38% mp. 133.5–134.0° C.

NMR(CDCl$_3$, δ) 1.21 (3H,t,J=7 Hz), 1.28 (9H,s), 4.11 (2H, m), 5.71 (1H,d,J=2 Hz), 5.88 (1H,d,J=2 Hz), 7.72 (1H,s), 7. 73 (1H,s), 8.54 (1H,s)

Example 18
3-(4-(t-Butoxycarbonyl)-$\Delta^2$-1,2,4-oxadiazolin-3-yl}-1-(2,6-dichloro-4-trifluoromethylphenyl)-5-ethoxymethyleneamino-4-trifluoromethylsulfinylpyrazole In 10 ml of acetonitrile was dissolved 538 mg (1.00 mmol) of 1-(2,6-dichloro-4-trifluoromethylphenyl)-5-ethoxymethyleneamino-3-($\Delta^2$-1,2,4-oxadiazolin-3-yl)-4-trifluoromethylsulfinylpyrazole. While this solution was stirred, 0.097 ml (1.20 mmol) of pyridine and 270 mg (1.20 mmol) of di-t-butyl dicarbonate were added. After 147 mg (1.20 mmol) of 4-dimethylaminopyridine was further added, the mixture was stirred at room temperature for 2 hours. This reaction mixture was concentrated under reduced pressure and the residue was subjected to silica gel column chromatography (n-hexane:ethyl acetate=4:1) to provide 485 mg (0.76 mmol) of the title compound as colorless amorphous powder.

yield: 76%

NMR (CDCl$_3$, δ) 1.22 (3H,t,J=7 Hz), 1.45 (9H,s), 3.98–4.26 (2H,m), 5.73 (1H,d,J=2 Hz), 5.78 (1H,d,J=2 Hz), 7.72–7.78 (2H,m), 8.61 (1H,s)

Example 19
1-(2,6-Dichloro-4-trifluoromethylphenyl)-3-{4-(N,N-diethylcarbamoyl)-$\Delta^2$-1,2,4-oxadiazolin-3-yl}-5-dimethylaminomethyleneamino-4-trifluoromethylsulfinylpyrazole In 5 ml of THF was dissolved 0.14 g (0.47 mmol) of bis(trichloromethyl) carbonate (BTC) followed by cooling on ice. Then, 0.13 ml (1.62 mmol) of pyridine was added and the mixture was stirred at room temperature for 35 minutes. To this mixture was added a solution of 0.45 g (0.84 mmol) of 1-(2,6-dichloro-4-trifluoromethylphenyl)-5-dimethylaminomethyleneamino-3-($\Delta^2$-1,2,4-oxadiazolin-3-yl)-4-trifluoromethylsulfinylpyrazole in 5 ml of THF dropwise under ice-cooling. After completion of the addition, the mixture was stirred at room temperature for 1 hour and 0.18 ml (1.74 mmol) of diethylamine was added under ice-cooling. Thereafter, the mixture was stirred under ice-cooling for 30 minutes and then at room temperature for 12 hours. After 0.09 ml (0.86 mmol) of diethylamine was further added, the mixture was stirred at room temperature for another 1.5 hours. This reaction mixture was diluted with 20 ml of water and 20 ml of saturated aqueous sodium chloride solution and extracted with 40 ml of ethyl acetate. The ethyl acetate layer was washed with 20 ml of saturated aqueous sodium chloride solution (x2) and dried over anhydrous magnesium sulfate. The solvent was then distilled off and the residue was purified by silica gel column chromatography (ethyl acetate:hexane=1:1). The resulting crystals were rinsed with ethyl acetate-hexane (1:5).and recrystallized from 20 ml of ethyl acetate-hexane to provide 0.30 g (0.47 mmol) of the title compound as colorless crystals.

yield: 57% mp. 156–158° C.

NMR (CDCl$_3$, δ) 1.14 (6H,t,J=7.2 Hz), 2.78 (3H,s), 3.07 (3H,s), 3.30 (4H,q,J=7 Hz), 5.47 (1H,d,J=1 Hz); 5.54 (1H, d,J=1 Hz,), 7.66–7.71 (2H,m), 8.65 (s,1H)

Example 20
1-(2,6-dichloro-4-trifluoromethylphenyl)-3-{3-(N,N-dimethylcarbamoyl)-$\Delta^2$-1,2,4-oxadiazolin-3-yl}-5-isopropoxymethyleneamino-4-trifluoromethylsulfinylpyrazole The mixture of 516 mg (2.71 nmmol) of truisopropyl orthoformate, 50 mg of p-toluenesulfonic acid monohydrate, and 500 mg (0.90 mmol) of 5-amino-1-(2,6-dichloro-4-trifluoromethylphenyl)-3-(4-(N,N-dimethylcarbamoyl)-$\Delta^2$-1,2,4-oxadiazolin-3-yl)-4-trifluoromethylsulfinylpyrazole was reacted for 1 hour at room temperature. After addition of 1.2 g (6.3 mmol) of truisopropyl orthoformate, the mixture was stirred for 18 hours. The mixture was further refluxed with stirring for 10 hours. This reaction mixture was poured in 100 ml of iced water and extracted with 100 ml of ethyl acetate. The extract was dried over anhydrous magnesium sulfate and concentrated to give yellow oil. The oil was subjected to silica gel column chromatography (n-hexane:ehtylacetate=1:1) to provide 240 mg (0.39 mmol) of 1-(2,6-dichloro-4-trifluoromethylphenyl)-3-{4-(N,N-dimethylcarbamoyl)-$\Delta^2$-1,2,4-oxadiazolin-3-yl}-5-isopropoxymethyleneamino-4-trifluoromethylsulfinylpyrazole as colorless crystals.

yield: 43% mp. 114–116° C.

NMR (CDC$_3$, δ) 1.10 (3H,d,J=6 Hz), 1.23 (3H,d,J=6 Hz), 2.95 (6H,s), 4.84 (1H,qu,J=6 Hz), 5.51 (1H,d,J=2 Hz), 5.59 (1H,d,J=2 Hz), 7.73 (2H,s), 8.56 (1H,s)

Example 21
1-(2,6-dichloro-4-trifluoromethylphenyl)-3-{4-(N,N-dimethylcarbamoyl)-$\Delta^2$-1,2,4-oxadiazolin-3-yl}-5-(4-hydroxy-3-methoxyphenyl)methyleneamino-4-trifluoromethylsulfinylpyrazole A mixture of 300 mg (1.97 mmol) of vanillin, 40 mg of p-toluenesulfonic acid monohydrate, 730 mg (1.32 mmol) of 5-amino-1-(2,6-dichloro-4-trifluoromethylphenyl)-3-{4-(N,N-dimethylcarbamoyl)-$\Delta^2$-1,2,4-oxadiazolin-3-yl}-4-trifluoromethylsulfinylpyrazole and 30 ml of toluene was reacted for 5 hours at 90° C., and the reaction mixture was further reacted with refluxing for 9 hours. This reaction mixture was poured in 30 ml of iced saline solution and extracted with 50 ml of ethyl acetate. The extract was dried over anhydrous magnesium sulfate and concentrated to give brown oil. The oil was subjected to silica gel column chromatography (n-hexane:acetone=2:1) to provide 240 mg (0.39 mmol) of 1-(2,6-dichloro-4-trifluoromethylphenyl)-3-(4-(N,N-dimethylcarbamoyl)-$\Delta^2$-1,2,4-oxadiazolin-3-yl)-5-(4-hydroxy-3-methoxyphenyl)methyleneamino-4-trifluoromethylsulfinylpyrazole as yellow crystals.

yield: 30%
mp. 174–175° C.
NMR (CDCl$_3$, $\delta$) 2.96 (6H,s), 3.83 (3H,s), 5.54 (1H,d,J=2H z), 5.62 (1H,d,J=2 Hz), 6.18 (1H,s), 6.93 (1H,d,J=8 Hz), 7.19 (1H,d,J=2 Hz), 7.32 (1H,dd,J=1.8 Hz,8.2 Hz), 7.70–7.72 (1 H,m), 7.76–7.77 (1H,m), 9.08 (1H,s)

Example 22
1-(2,6-dichloro-4-trifluoromethylphenyl)-3-{4-(N,N-dimethylcarbamoyl)-$\Delta^2$-1,2,4-oxadiazolin-3-yl}-5-(1-pyrrolyl)-4-trifluoromethylsulfinylpyrazole A mixture of 0.15 ml (1.16 mmol) of 2,5-dimethoxytetrahydrofuran, 27 mg of p-toluenesulfonic acid monohydrate, 550 mg (0.99 mmol) of 5-amino-1-(2,6-dichloro-4-trifluoromethylphenyl)-3-{4-(N,N-dimethylcarbamoyl)-$\Delta^2$-1,2,4-oxadiazolin-3-yl}-4-trifluoromethylsulfinylpyrazole and 120 ml of toluene was reacted for 3 hours at 80° C. 50 ml of ethyl acetate was added to the reaction mixture, and then the organic layer was washed with 30 ml of saturated saline solution 3 times. The organic layer was dried over anhydrous magnesium sulfate and concentrated to give brown crystals. The crystals were washed with chloroform to provide 283 mg (0.47 mmol) of 1-(2,6-dichloro-4-trifluoromethylphenyl)-3-{4-(N,N-dimethylcarbamoyl)-$\Delta^2$-1,2,4-oxadiazolin-3-yl}-5-(1-pyrrolyl)-4-trifluoromethylsulfinylpyrazole as light brown crystals.

yield: 47%
mp. 244–246t
NMR (CDCl$_3$, $\delta$) 2.97 (6H,s), 5.66 (1H,d,J=2 Hz), 5.80 (1H,d,J=2 Hz), 6.19 (2H,d,J=2 Hz), 6.89 (2H,t,J=2 Hz), 8.02–8.04 (1H,m), 8.10–8.13 (1H,m)

Example 23
5-Amino-1-(2,6-dichloro-4-trifluoromethylphenyl)-3-{4-(N,N-dimethylcarbamoyl)-$\Delta^2$-1,2,4-oxadiazolin-3-yl}-4-ethylthiopyrazole In 20 ml of THF was dissolved 410 mg (1.39 mmol) of bis(trichloromethyl) carbonate (BTC) followed by cooling on ice. To this solution was added 0.30 ml (3.87 mmol) of pyridine, and the mixture was stirred for 30 minutes under ice-cooling. Then, a solution of 1.50 g (3.52 mmol) of 5-amino-1-(2,6-dichloro-4-trifluoromethylphenyl)-3-($\Delta^2$-1,2,4-oxadiazolin-3-yl)-4-ethylthiopyrazole in 10 ml of THF was added dropwise to the above mixture under ice-cooling and the whole mixture was stirred for 1.5 hours. After completion of the reaction, 0.94 ml (10.3 mmol) of diethylamine was added and the mixture was stirred at room temperature for 2 hours. The reaction mixture was concentrated and the residue was dissolved in 200 ml of ethyl acetate. This solution was washed with 200 ml of saturated saline solution, 200 ml of 1% aqueous hydrochloric acid and 200 ml of saturated saline solution again, and the solution was dried over anhydrous magnesium sulfate. The solvent was distilled off, and the residue was subjected to silica gel column chromatography (n-hexane:ethyl acetate=3:1) to give colorless crystals. This crystal crop was washed with n-hexane to provide 440 mg (0.885 mmol) of the title compound as colorless crystals.

yield: 25%
mp. 187.0–199.0° C.
NMR (CDCl$_3$, $\delta$) 1.21 (3H,t,J=7 Hz), 2.76 (2H,q,J=7 Hz), 3.0 5(6H,s), 4.10(2H,s),5.85(2H,s),7.75 (2H,s)

Example 24
5-Amino-1-(2,6-dichloro-4-trifluoromethylphenyl)-3-(4-(N,N-dimethylcarbamoyl)-$\Delta^2$-1,2,4-oxadiazolin-3-yl)-4-ethylsulfinylpyrazole In 10 ml of dichloromethane was dissolved 100 mg (0.201 mmol) of 5-amino-1-(2,6-dichloro-4-trifluoromethylphenyl)-3-{4-(N,N-dimethylcarbamoyl)-$\Delta^2$-1,2,4-oxadiazolin-3-yl}-4-ethylthiopyrazole followed by cooling on ice. To this solution was added 45 mg (0.258 mmol) of 3-chloroperbenzoic acid in 1 ml dichloromethane dropwise under ice-cooling and the whole mixture was stirred for 2 hours. To the reaction mixture was added 5 ml of saturated aqueous sodium hydrogen carbonate solution and extracted with 30 ml of chloroform. The organic phase was washed with 100 ml of saturated saline solution and dried over anhydrous magnesium sulfate. The solvent was distilled off, and the residue was subjected to silica gel column chromatography(ethyl acetate) to give colorless crystals. This crystal crop was recrystallized from n-hexane-ethyl acetate to provide 80 mg (0.156 mmol) of the title compound as colorless crystals.

yield: 78%
mp. 223.0–225.0° C.
NMR (CDCl$_3$, $\delta$) 1.37 (3H,t,J=7 Hz), 3.04 (6H,s),3.18 (2H,q,J=7 Hz),5.08 (2H,s),5.77 (2H,s),7.76 (2H,s)

Example 25
5-Amino-1-(2,6-dichloro-4-trifluoromethylphenyl)-3-{4-(N,N-dimethylcarbamoyl)-$\Delta^2$-1,2,4-oxadiazolin-3-yl}-4-ethylsulfonylpyrazole In 10 ml of dichloromethane was dissolved 100 mg (0.201 mmol) of 5-amino-1-(2,6-dichloro-4-trifluoromethylphenyl)-3-{4-(N,N-dimethylcarbamoyl)-$\Delta^2$-1,2,4-oxadiazolin-3-yl}-4-ethylthiopyrazole. To this solution was added 100 mg(0. 579 mmol) of 3-chloroperbenzoic acid in 5 ml dichloromethane dropwise and stirred for 18 hrs at room temperature. To the reaction mixture was added 10 ml of saturated aqueous sodium hydrogen carbonate solution and extracted with 30 ml of chloroform. The organic phase was washed with 100 ml of saturated saline solution and dried over anhydrous magnesium sulfate. The solvent was distilled off, and residual colorless crystals recrystallized from n-hexane-ethyl acetate to provide 80 lmg (0.151 mmol) of the title compound as colorless crystals.

yield: 75%
mp. 203.0–205.0° C.
NMR (CDCl$_3$, $\delta$) 1.33(3H,t,J=7 Hz),3.01(6H,s),3.57(2H,q,J=7 Hz),5.20(2H,s),5.86(2H,s),7.78 (2H,s)

The representative compounds of the invention as obtained in the same manner as in Examples 1–25, inclusive of the compounds synthesized in those Examples, are listed in Table 1 through Table 36.

TABLE 1

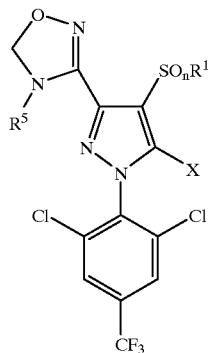

| Comp. No. | n | R¹ | R⁵ | X | mp. (° C.) |
|---|---|---|---|---|---|
| 1-1 | 0 | CF₃ | MeCO | N=CHOMe | |
| 1-2 | 1 | CF₃ | MeCO | N=CHOMe | 126–127 |
| 1-3 | 2 | CF₃ | MeCO | N=CHOMe | |
| 1-4 | 0 | CF₃ | MeCO | N=CHOEt | |
| 1-5 | 1 | CF₃ | MeCO | N=CHOEt | 116–118 |
| 1-6 | 2 | CF₃ | MeCO | N=CHOEt | |
| 1-7 | 0 | CF₃ | MeCO | N=CHOPr-n | 101–103 |
| 1-8 | 1 | CF₃ | MeCO | N=CHOPr-n | |
| 1-9 | 2 | CF₃ | MeCO | N=CHOPr-n | |
| 1-10 | 0 | CF₃ | MeCO | N=CHOPr-i | |
| 1-11 | 1 | CF₃ | MeCO | N=CHOPr-i | |
| 1-12 | 2 | CF₃ | MeCO | N=CHOPr-i | |
| 1-13 | 0 | CF₃ | MeCO | N=CHOBu-n | |
| 1-14 | 1 | CF₃ | MeCO | N=CHOBu-n | |
| 1-15 | 2 | CF₃ | MeCO | N=CHOBu-n | |
| 1-16 | 0 | CF₃ | MeCO | N=CHOBu-i | |
| 1-17 | 1 | CF₃ | MeCO | N=CHOBu-i | |
| 1-18 | 2 | CF₃ | MeCO | N=CHOBu-i | |
| 1-19 | 0 | CF₃ | MeCO | N=CHOBu-s | |
| 1-20 | 1 | CF₃ | MeCO | N=CHOBu-s | |
| 1-21 | 2 | CF₃ | MeCO | N=CHOBu-s | |
| 1-22 | 0 | CF₃ | MeCO | N=CHOBu-t | |
| 1-23 | 1 | CF₃ | MeCO | N=CHOBu-t | |
| 1-24 | 2 | CF₃ | MeCO | N=CHOBu-t | |
| 1-25 | 0 | CF₃ | MeCO | NH₂ | |
| 1-26 | 1 | CF₃ | MeCO | NH₂ | 161–164 |
| 1-27 | 2 | CF₃ | MeCO | NH₂ | |

TABLE 2

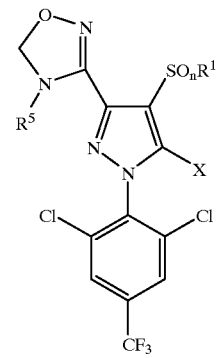

| Comp. No. | n | R¹ | R⁵ | X | mp. (° C.) |
|---|---|---|---|---|---|
| 2-1 | 0 | CF₃ | EtCO | N=CHOMe | |
| 2-2 | 1 | CF₃ | EtCO | N=CHOMe | |
| 2-3 | 2 | CF₃ | EtCO | N=CHOMe | |
| 2-4 | 0 | CF₃ | EtCO | N=CHOEt | |
| 2-5 | 1 | CF₃ | EtCO | N=CHOEt | 114–115 |
| 2-6 | 2 | CF₃ | EtCO | N=CHOEt | |
| 2-7 | 0 | CF₃ | EtCO | N=CHOPr-n | |
| 2-8 | 1 | CF₃ | EtCO | N=CHOPr-n | 85–86 |
| 2-9 | 2 | CF₃ | EtCO | N=CHOPr-n | |
| 2-10 | 0 | CF₃ | EtCO | N=CHOPr-i | |
| 2-11 | 1 | CF₃ | EtCO | N=CHOPr-i | |
| 2-12 | 2 | CF₃ | EtCO | N=CHOPr-i | |
| 2-13 | 0 | CF₃ | EtCO | N=CHOBu-n | |
| 2-14 | 1 | CF₃ | EtCO | N=CHOBu-n | |
| 2-15 | 2 | CF₃ | EtCO | N=CHOBu-n | |
| 2-16 | 0 | CF₃ | EtCO | N=CHOBu-i | |
| 2-17 | 1 | CF₃ | EtCO | N=CHOBu-i | |
| 2-18 | 2 | CF₃ | EtCO | N=CHOBu-i | |
| 2-19 | 0 | CF₃ | EtCO | N=CHOBu-s | |
| 2-20 | 1 | CF₃ | EtCO | N=CHOBu-s | |
| 2-21 | 2 | CF₃ | EtCO | N=CHOBu-s | |
| 2-22 | 0 | CF₃ | EtCO | N=CHOBu-t | |
| 2-23 | 1 | CF₃ | EtCO | N=CHOBu-t | |
| 2-24 | 2 | CF₃ | EtCO | N=CHOBu-t | |
| 2-25 | 0 | CF₃ | EtCO | NH₂ | |
| 2-26 | 1 | CF₃ | EtCO | NH₂ | |
| 2-27 | 2 | CF₃ | EtCO | NH₂ | |

TABLE 3

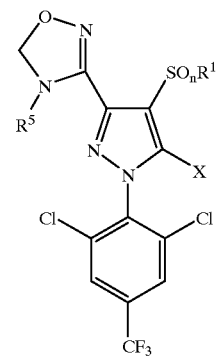

| Comp. No | n | R¹ | R⁵ | X | mp. (° C.) |
|---|---|---|---|---|---|
| 3-1 | 0 | CF₃ | n-PrCO | N=CHOMe | |
| 3-2 | 1 | CF₃ | n-PrCO | N=CHOMe | |
| 3-3 | 2 | CF₃ | n-PrCO | N=CHOMe | |
| 3-4 | 0 | CF₃ | n-PrCO | N=CHOEt | |
| 3-5 | 1 | CF₃ | n-PrCO | N=CHOEt | 88–89 |
| 3-6 | 2 | CF₃ | n-PrCO | N=CHOEt | |
| 3-7 | 0 | CF₃ | n-PrCO | N=CHOPr-n | |
| 3-8 | 1 | CF₃ | n-PrCO | N=CHOPr-n | |
| 3-9 | 2 | CF₃ | n-PrCO | N=CHOPr-n | |
| 3-10 | 0 | CF₃ | n-PrCO | N=CHOPr-i | |
| 3-11 | 1 | CF₃ | n-PrCO | N=CHOPr-i | |
| 3-12 | 2 | CF₃ | n-PrCO | N=CHOPr-i | |

TABLE 3-continued

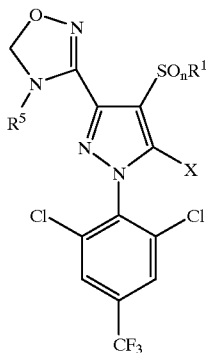

| Comp. No | n | R[1] | R[5] | X | mp. (° C.) |
|---|---|---|---|---|---|
| 3-13 | 0 | $CF_3$ | n-PrCO | N=CHOBu-n | |
| 3-14 | 1 | $CF_3$ | n-PrCO | N=CHOBu-n | |
| 3-15 | 2 | $CF_3$ | n-PrCO | N=CHOBu-n | |
| 3-16 | 0 | $CF_3$ | n-PrCO | N=CHOBu-i | |
| 3-17 | 1 | $CF_3$ | n-PrCO | N=CHOBu-i | |
| 3-18 | 2 | $CF_3$ | n-PrCO | N=CHOBu-i | |
| 3-19 | 0 | $CF_3$ | n-PrCO | N=CHOBu-s | |
| 3-20 | 1 | $CF_3$ | n-PrCO | N=CHOBu-s | |
| 3-21 | 2 | $CF_3$ | n-PrCO | N=CHOBu-s | |
| 3-22 | 0 | $CF_3$ | n-PrCO | N=CHOBu-t | |
| 3-23 | 1 | $CF_3$ | n-PrCO | N=CHOBu-t | |
| 3-24 | 2 | $CF_3$ | n-PrCO | N=CHOBu-t | |
| 3-25 | 0 | $CF_3$ | n-PrCO | $NH_3$ | |
| 3-26 | 1 | $CF_3$ | n-PrCO | $NH_3$ | |
| 3-27 | 2 | $CF_3$ | n-PrCO | $NH_3$ | |

TABLE 4

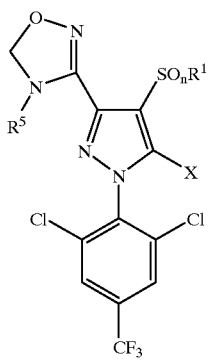

| Comp. No. | n | R[1] | R[5] | X | mp. (° C.) |
|---|---|---|---|---|---|
| 4-1 | 0 | $CF_3$ | i-PrCO | N=CHOMe | |
| 4-2 | 1 | $CF_3$ | i-PrCO | N=CHOMe | |
| 4-3 | 2 | $CF_3$ | i-PrCO | N=CHOMe | |
| 4-4 | 0 | $CF_3$ | i-PrCO | N=CHOEt | (Oil)[1)] |
| 4-5 | 1 | $CF_3$ | i-PrCO | N=CHOEt | (Oil)[2)] |
| 4-6 | 2 | $CF_3$ | i-PrCO | N=CHOEt | 99–100 |
| 4-7 | 0 | $CF_3$ | i-PrCO | N=CHOPr-n | |
| 4-8 | 1 | $CF_3$ | i-PrCO | N=CHOPr-n | |
| 4-9 | 2 | $CF_3$ | i-PrCO | N=CHOPr-n | |
| 4-10 | 0 | $CF_3$ | i-PrCO | N=CHOPr-i | |
| 4-11 | 1 | $CF_3$ | i-PrCO | N=CHOPr-i | |
| 4-12 | 2 | $CF_3$ | i-PrCO | N=CHOPr-i | |
| 4-13 | 0 | $CF_3$ | i-PrCO | N=CHOBu-n | |
| 4-14 | 1 | $CF_3$ | i-PrCO | N=CHOBu-n | |
| 4-15 | 2 | $CF_3$ | i-PrCO | N=CHOBu-n | |
| 4-16 | 0 | $CF_3$ | i-PrCO | N=CHOBu-i | |
| 4-17 | 1 | $CF_3$ | i-PrCO | N=CHOBu-i | |
| 4-18 | 2 | $CF_3$ | i-PrCO | N=CHOBu-i | |

TABLE 4-continued

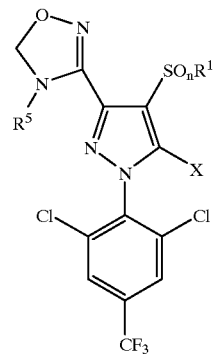

| Comp. No. | n | R[1] | R[5] | X | mp. (° C.) |
|---|---|---|---|---|---|
| 4-19 | 0 | $CF_3$ | i-PrCO | N=CHOBu-s | |
| 4-20 | 1 | $CF_3$ | i-PrCO | N=CHOBu-s | |
| 4-21 | 2 | $CF_3$ | i-PrCO | N=CHOBu-s | |
| 4-22 | 0 | $CF_3$ | i-PrCO | N=CHOBu-t | |
| 4-23 | 1 | $CF_3$ | i-PrCO | N=CHOBu-t | |
| 4-24 | 2 | $CF_3$ | i-PrCO | N=CHOBu-t | |
| 4-25 | 0 | $CF_3$ | i-PrCO | $NH_2$ | |
| 4-26 | 1 | $CF_3$ | i-PrCO | $NH_2$ | |
| 4-27 | 2 | $CF_3$ | i-PrCO | $NH_2$ | |

TABLE 5

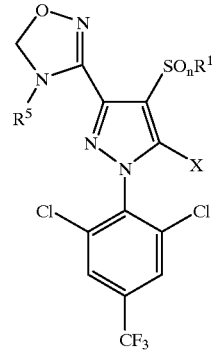

| Comp. No. | n | R[1] | R[5] | X | mp. (° C.) |
|---|---|---|---|---|---|
| 5-1 | 0 | $CF_3$ | n-BuCO | N=CHOMe | |
| 5-2 | 1 | $CF_3$ | n-BuCO | N=CHOMe | |
| 5-3 | 2 | $CF_3$ | n-BuCO | N=CHOMe | |
| 5-4 | 0 | $CF_3$ | n-BuCO | N=CHOEt | |
| 5-5 | 1 | $CF_3$ | n-BuCO | N=CHOEt | 96–96.5 |
| 5-6 | 2 | $CF_3$ | n-BuCO | N=CHOEt | |
| 5-7 | 0 | $CF_3$ | n-BuCO | N=CHOPr-n | |
| 5-8 | 1 | $CF_3$ | n-BuCO | N=CHOPr-n | |
| 5-9 | 2 | $CF_3$ | n-BuCO | N=CHOPr-n | |
| 5-10 | 0 | $CF_3$ | n-BuCO | N=CHOPr-i | |
| 5-11 | 1 | $CF_3$ | n-BuCO | N=CHOPr-i | |
| 5-12 | 2 | $CF_3$ | n-BuCO | N=CHOPr-i | |
| 5-13 | 0 | $CF_3$ | n-BuCO | N=CHOBu-n | |
| 5-14 | 1 | $CF_3$ | n-BuCO | N=CHOBu-n | |
| 5-15 | 2 | $CF_3$ | n-BuCO | N=CHOBu-n | |
| 5-16 | 0 | $CF_3$ | n-BuCO | N=CHOBu-i | |
| 5-17 | 1 | $CF_3$ | n-BuCO | N=CHOBu-i | |
| 5-18 | 2 | $CF_3$ | n-BuCO | N=CHOBu-i | |
| 5-19 | 0 | $CF_3$ | n-BuCO | N=CHOBu-s | |
| 5-20 | 1 | $CF_3$ | n-BuCO | N=CHOBu-s | |
| 5-21 | 2 | $CF_3$ | n-BuCO | N=CHOBu-s | |
| 5-22 | 0 | $CF_3$ | n-BuCO | N=CHOBu-t | |
| 5-23 | 1 | $CF_3$ | n-BuCO | N=CHOBu-t | |
| 5-24 | 2 | $CF_3$ | n-BuCO | N=CHOBu-t | |

TABLE 5-continued

| Comp. No. | n | R¹ | R⁵ | X | mp. (° C.) |
|---|---|---|---|---|---|
| 5-25 | 0 | CF$_3$ | n-BuCO | NH$_2$ | |
| 5-26 | 1 | CF$_3$ | n-BuCO | NH$_2$ | |
| 5-27 | 2 | CF$_3$ | n-BuCO | NH$_2$ | |

TABLE 6

| Comp. No. | n | R¹ | R⁵ | X | mp. (° C.) |
|---|---|---|---|---|---|
| 6-1 | 0 | CF$_3$ | i-BuCO | N=CHOMe | |
| 6-2 | 1 | CF$_3$ | i-BuCO | N=CHOMe | |
| 6-3 | 2 | CF$_3$ | i-BuCO | N=CHOMe | |
| 6-4 | 0 | CF$_3$ | i-BuCO | N=CHOEt | |
| 6-5 | 1 | CF$_3$ | i-BuCO | N=CHOEt | 104–105 |
| 6-6 | 2 | CF$_3$ | i-BuCO | N=CHOEt | |
| 6-7 | 0 | CF$_3$ | i-BuCO | N=CHOPr-n | |
| 6-8 | 1 | CF$_3$ | i-BuCO | N=CHOPr-n | |
| 6-9 | 2 | CF$_3$ | i-BuCO | N=CHOPr-n | |
| 6-10 | 0 | CF$_3$ | i-BuCO | N=CHOPr-i | |
| 6-11 | 1 | CF$_3$ | i-BuCO | N=CHOPr-i | |
| 6-12 | 2 | CF$_3$ | i-BuCO | N=CHOPr-i | |
| 6-13 | 0 | CF$_3$ | i-BuCO | N=CHOBu-n | |
| 6-14 | 1 | CF$_3$ | i-BuCO | N=CHOBu-n | |
| 6-15 | 2 | CF$_3$ | i-BuCO | N=CHOBu-n | |
| 6-16 | 0 | CF$_3$ | i-BuCO | N=CHOBu-i | |
| 6-17 | 1 | CF$_3$ | i-BuCO | N=CHOBu-i | |
| 6-18 | 2 | CF$_3$ | i-BuCO | N=CHOBu-i | |
| 6-19 | 0 | CF$_3$ | i-BuCO | N=CHOBu-s | |
| 6-20 | 1 | CF$_3$ | i-BuCO | N=CHOBu-s | |
| 6-21 | 2 | CF$_3$ | i-BuCO | N=CHOBu-s | |
| 6-22 | 0 | CF$_3$ | i-BuCO | N=CHOBu-t | |
| 6-23 | 1 | CF$_3$ | i-BuCO | N=CHOBu-t | |
| 6-24 | 2 | CF$_3$ | i-BuCO | N=CHOBu-t | |
| 6-25 | 0 | CF$_3$ | i-BuCO | NH$_2$ | |
| 6-26 | 1 | CF$_3$ | i-BuCO | NH$_2$ | |
| 6-27 | 2 | CF$_3$ | i-BuCO | NH$_2$ | |

TABLE 7

| Comp. No. | n | R¹ | R⁵ | X | mp. (° C.) |
|---|---|---|---|---|---|
| 7-1 | 0 | CF$_3$ | s-BuCO | N=CHOMe | |
| 7-2 | 1 | CF$_3$ | s-BuCO | N=CHOMe | |
| 7-3 | 2 | CF$_3$ | s-BuCO | N=CHOMe | |
| 7-4 | 0 | CF$_3$ | s-BuCO | N=CHOEt | (Oil)[3] |
| 7-5 | 1 | CF$_3$ | s-BuCO | N=CHOEt | 92–93 |
| 7-6 | 2 | CF$_3$ | s-BuCO | N=CHOEt | 102.5–105 |
| 7-7 | 0 | CF$_3$ | s-BuCO | N=CHOPr-n | |
| 7-8 | 1 | CF$_3$ | s-BuCO | N=CHOPr-n | |
| 7-9 | 2 | CF$_3$ | s-BuCO | N=CHOPr-n | |
| 7-10 | 0 | CF$_3$ | s-BuCO | N=CHOPr-i | |
| 7-11 | 1 | CF$_3$ | s-BuCO | N=CHOPr-i | |
| 7-12 | 2 | CF$_3$ | s-BuCO | N=CHOPr-i | |
| 7-13 | 0 | CF$_3$ | s-BuCO | N=CHOBu-n | |
| 7-14 | 1 | CF$_3$ | s-BuCO | N=CHOBu-n | |
| 7-15 | 2 | CF$_3$ | s-BuCO | N=CHOBu-n | |
| 7-16 | 0 | CF$_3$ | s-BuCO | N=CHOBu-i | |
| 7-17 | 1 | CF$_3$ | s-BuCO | N=CHOBu-i | |
| 7-18 | 2 | CF$_3$ | s-BuCO | N=CHOBu-i | |
| 7-19 | 0 | CF$_3$ | s-BuCO | N=CHOBu-s | |
| 7-20 | 1 | CF$_3$ | s-BuCO | N=CHOBu-s | |
| 7-21 | 2 | CF$_3$ | s-BuCO | N=CHOBu-s | |
| 7-22 | 0 | CF$_3$ | s-BuCO | N=CHOBu-t | |
| 7-23 | 1 | CF$_3$ | s-BuCO | N=CHOBu-t | |
| 7-24 | 2 | CF$_3$ | s-BuCO | N=CHOBu-t | |
| 7-25 | 0 | CF$_3$ | s-BuCO | NH$_2$ | |
| 7-26 | 1 | CF$_3$ | s-BuCO | NH$_2$ | |
| 7-27 | 2 | CF$_3$ | s-BuCO | NH$_2$ | |

TABLE 8

| Comp. No. | n | R¹ | R⁵ | X | mp. (° C.) |
|---|---|---|---|---|---|
| 8-1 | 0 | CF$_3$ | t-BuCO | N=CHOMe | |
| 8-2 | 1 | CF$_3$ | t-BuCO | N=CHOMe | |
| 8-3 | 2 | CF$_3$ | t-BuCO | N=CHOMe | |
| 8-4 | 0 | CF$_3$ | t-BuCO | N=CHOEt | (amorphous)[4] |
| 8-5 | 1 | CF$_3$ | t-BuCO | N=CHOEt | 133.5–134 |
| 8-6 | 2 | CF$_3$ | t-BuCO | N=CHOEt | 126–127 |

TABLE 8-continued

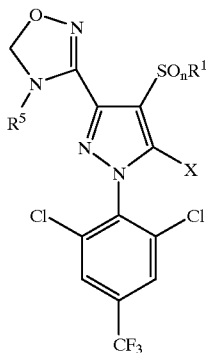

| Comp. No. | n | $R^1$ | $R^5$ | X | mp. (° C.) |
|---|---|---|---|---|---|
| 8-7 | 0 | $CF_3$ | t-BuCO | N=CHOPr-n | |
| 8-8 | 1 | $CF_3$ | t-BuCO | N=CHOPr-n | |
| 8-9 | 2 | $CF_3$ | t-BuCO | N=CHOPr-n | |
| 8-10 | 0 | $CF_3$ | t-BuCO | N=CHOPr-i | |
| 8-11 | 1 | $CF_3$ | t-BuCO | N=CHOPr-i | |
| 8-12 | 2 | $CF_3$ | t-BuCO | N=CHOPr-i | |
| 8-13 | 0 | $CF_3$ | t-BuCO | N=CHOBu-n | |
| 8-14 | 1 | $CF_3$ | t-BuCO | N=CHOBu-n | |
| 8-15 | 2 | $CF_3$ | t-BuCO | N=CHOBu-n | |
| 8-16 | 0 | $CF_3$ | t-BuCO | N=CHOBu-i | |
| 8-17 | 1 | $CF_3$ | t-BuCO | N=CHOBu-i | |
| 8-18 | 2 | $CF_3$ | t-BuCO | N=CHOBu-i | |
| 8-19 | 0 | $CF_3$ | t-BuCO | N=CHOBu-s | |
| 8-20 | 1 | $CF_3$ | t-BuCO | N=CHOBu-s | |
| 8-21 | 2 | $CF_3$ | t-BuCO | N=CHOBu-s | |
| 8-22 | 0 | $CF_3$ | t-BuCO | N=CHOBu-t | |
| 8-23 | 1 | $CF_3$ | t-BuCO | N=CHOBu-t | |
| 8-24 | 2 | $CF_3$ | t-BuCO | N=CHOBu-t | |
| 8-25 | 0 | $CF_3$ | t-BuCO | $NH_2$ | |
| 8-26 | 1 | $CF_3$ | t-BuCO | $NH_2$ | |
| 8-27 | 2 | $CF_3$ | t-BuCO | $NH_2$ | |

TABLE 9

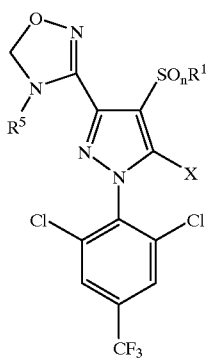

| Comp. No. | n | $R^1$ | $R^5$ | X | mp. (° C.) |
|---|---|---|---|---|---|
| 9-1 | 0 | $CF_3$ | PhCO | N=CHOMe | |
| 9-2 | 1 | $CF_3$ | PhCO | N=CHOMe | |
| 9-3 | 2 | $CF_3$ | PhCO | N=CHOMe | |
| 9-4 | 0 | $CF_3$ | PhCO | N=CHOEt | |
| 9-5 | 1 | $CF_3$ | PhCO | N=CHOEt | 138–139 |
| 9-6 | 2 | $CF_3$ | PhCO | N=CHOEt | |
| 9-7 | 0 | $CF_3$ | PhCO | N=CHOPr-n | |
| 9-8 | 1 | $CF_3$ | PhCO | N=CHOPr-n | |
| 9-9 | 2 | $CF_3$ | PhCO | N=CHOPr-n | |
| 9-10 | 0 | $CF_3$ | PhCO | N=CHOPr-i | |
| 9-11 | 1 | $CF_3$ | PhCO | N=CHOPr-i | |
| 9-12 | 2 | $CF_3$ | PhCO | N=CHOPr-i | |

TABLE 9-continued

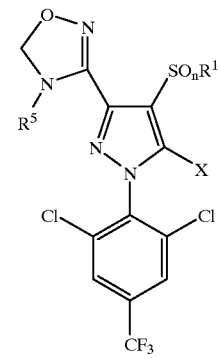

| Comp. No. | n | $R^1$ | $R^5$ | X | mp. (° C.) |
|---|---|---|---|---|---|
| 9-13 | 0 | $CF_3$ | PhCO | N=CHOBu-n | |
| 9-14 | 1 | $CF_3$ | PhCO | N=CHOBu-n | |
| 9-15 | 2 | $CF_3$ | PhCO | N=CHOBu-n | |
| 9-16 | 0 | $CF_3$ | PhCO | N=CHOBu-i | |
| 9-17 | 1 | $CF_3$ | PhCO | N=CHOBu-i | |
| 9-18 | 2 | $CF_3$ | PhCO | N=CHOBu-i | |
| 9-19 | 0 | $CF_3$ | PhCO | N=CHOBu-s | |
| 9-20 | 1 | $CF_3$ | PhCO | N=CHOBu-s | |
| 9-21 | 2 | $CF_3$ | PhCO | N=CHOBu-s | |
| 9-22 | 0 | $CF_3$ | PhCO | N=CHOBu-t | |
| 9-23 | 1 | $CF_3$ | PhCO | N=CHOBu-t | |
| 9-24 | 2 | $CF_3$ | PhCO | N=CHOBu-t | |
| 9-25 | 0 | $CF_3$ | PhCO | $NH_2$ | |
| 9-26 | 1 | $CF_3$ | PhCO | $NH_2$ | |
| 9-27 | 2 | $CF_3$ | PhCO | $NH_2$ | |

TABLE 10

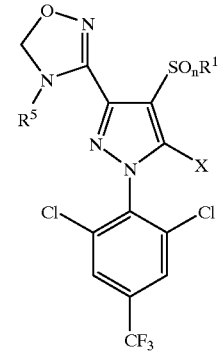

| Comp. No. | n | $R^1$ | $R^5$ | X | mp. (° C.) |
|---|---|---|---|---|---|
| 10-1 | 0 | $CF_3$ | $Me_2NCH_2CO$ | N=CHOMe | |
| 10-2 | 1 | $CF_3$ | $Me_2NCH_2CO$ | N=CHOMe | |
| 10-3 | 2 | $CF_3$ | $Me_2NCH_2CO$ | N=CHOMe | |
| 10-4 | 0 | $CF_3$ | $Me_2NCH_2CO$ | N=CHOEt | |
| 10-5 | 1 | $CF_3$ | $Me_2NCH_2CO$ | N=CHOEt | 135 |
| 10-6 | 2 | $CF_3$ | $Me_2NCH_2CO$ | N=CHOEt | |
| 10-7 | 0 | $CF_3$ | $Me_2NCH_2CO$ | N=CHOPr-n | |
| 10-8 | 1 | $CF_3$ | $Me_2NCH_2CO$ | N=CHOPr-n | |
| 10-9 | 2 | $CF_3$ | $Me_2NCH_2CO$ | N=CHOPr-n | |
| 10-10 | 0 | $CF_3$ | $Me_2NCH_2CO$ | N=CHOPr-i | |
| 10-11 | 1 | $CF_3$ | $Me_2NCH_2CO$ | N=CHOPr-i | |
| 10-12 | 2 | $CF_3$ | $Me_2NCH_2CO$ | N=CHOPr-i | |
| 10-13 | 0 | $CF_3$ | $Me_2NCH_2CO$ | N=CHOBu-n | |
| 10-14 | 1 | $CF_3$ | $Me_2NCH_2CO$ | N=CHOBu-n | |
| 10-15 | 2 | $CF_3$ | $Me_2NCH_2CO$ | N=CHOBu-n | |
| 10-16 | 0 | $CF_3$ | $Me_2NCH_2CO$ | N=CHOBu-i | |
| 10-17 | 1 | $CF_3$ | $Me_2NCH_2CO$ | N=CHOBu-i | |
| 10-18 | 2 | $CF_3$ | $Me_2NCH_2CO$ | N=CHOBu-i | |

TABLE 10-continued

| Comp. No. | n | R¹ | R⁵ | X | mp. (° C.) |
|---|---|---|---|---|---|
| 10-19 | 0 | $CF_3$ | $Me_2NCH_2CO$ | N=CHOBu-s | |
| 10-20 | 1 | $CF_3$ | $Me_2NCH_2CO$ | N=CHOBu-s | |
| 10-21 | 2 | $CF_3$ | $Me_2NCH_2CO$ | N=CHOBu-s | |
| 10-22 | 0 | $CF_3$ | $Me_2NCH_2CO$ | N=CHOBu-t | |
| 10-23 | 1 | $CF_3$ | $Me_2NCH_2CO$ | N=CHOBu-t | |
| 10-24 | 2 | $CF_3$ | $Me_2NCH_2CO$ | N=CHOBu-t | |
| 10-25 | 0 | $CF_3$ | $Me_2NCH_2CO$ | $NH_2$ | |
| 10-26 | 1 | $CF_3$ | $Me_2NCH_2CO$ | $NH_2$ | |
| 10-27 | 2 | $CF_3$ | $Me_2NCH_2CO$ | $NH_2$ | |

TABLE 11

| Comp. No. | n | R¹ | R⁵ | X | mp. (° C.) |
|---|---|---|---|---|---|
| 11-1 | 0 | $CF_3$ | $H_2NCO$ | N=CHOMe | |
| 11-2 | 1 | $CF_3$ | $H_2NCO$ | N=CHOMe | |
| 11-3 | 2 | $CF_3$ | $H_2NCO$ | N=CHOMe | |
| 11-4 | 0 | $CF_3$ | $H_2NCO$ | N=CHOEt | |
| 11-5 | 1 | $CF_3$ | $H_2NCO$ | N=CHOEt | 86.5–87 |
| 11-6 | 2 | $CF_3$ | $H_2NCO$ | N=CHOEt | |
| 11-7 | 0 | $CF_3$ | $H_2NCO$ | N=CHOPr-n | |
| 11-8 | 1 | $CF_3$ | $H_2NCO$ | N=CHOPr-n | |
| 11-9 | 2 | $CF_3$ | $H_2NCO$ | N=CHOPr-n | |
| 11-10 | 0 | $CF_3$ | $H_2NCO$ | N=CHOPr-i | |
| 11-11 | 1 | $CF_3$ | $H_2NCO$ | N=CHOPr-i | |
| 11-12 | 2 | $CF_3$ | $H_2NCO$ | N=CHOPr-i | |
| 11-13 | 0 | $CF_3$ | $H_2NCO$ | N=CHOBu-n | |
| 11-14 | 1 | $CF_3$ | $H_2NCO$ | N=CHOBu-n | |
| 11-15 | 2 | $CF_3$ | $H_2NCO$ | N=CHOBu-n | |
| 11-16 | 0 | $CF_3$ | $H_2NCO$ | N=CHOBu-i | |
| 11-17 | 1 | $CF_3$ | $H_2NCO$ | N=CHOBu-i | |
| 11-18 | 2 | $CF_3$ | $H_2NCO$ | N=CHOBu-i | |
| 11-19 | 0 | $CF_3$ | $H_2NCO$ | N=CHOBu-s | |
| 11-20 | 1 | $CF_3$ | $H_2NCO$ | N=CHOBu-s | |
| 11-21 | 2 | $CF_3$ | $H_2NCO$ | N=CHOBu-s | |
| 11-22 | 0 | $CF_3$ | $H_2NCO$ | N=CHOBu-t | |
| 11-23 | 1 | $CF_3$ | $H_2NCO$ | N=CHOBu-t | |
| 11-24 | 2 | $CF_3$ | $H_2NCO$ | N=CHOBu-t | |

TABLE 11-continued

| Comp. No. | n | R¹ | R⁵ | X | mp. (° C.) |
|---|---|---|---|---|---|
| 11-25 | 0 | $CF_3$ | $H_2NCO$ | $NH_2$ | |
| 11-26 | 1 | $CF_3$ | $H_2NCO$ | $NH_2$ | 121–122 |
| 11-27 | 2 | $CF_3$ | $H_2NCO$ | $NH_2$ | |

TABLE 12

| Comp. No. | n | R¹ | R⁵ | X | mp. (° C.) |
|---|---|---|---|---|---|
| 12-1 | 0 | $CF_3$ | MeNHCO | N=CHOMe | |
| 12-2 | 1 | $CF_3$ | MeNHCO | N=CHOMe | |
| 12-3 | 2 | $CF_3$ | MeNHCO | N=CHOMe | |
| 12-4 | 0 | $CF_3$ | MeNHCO | N=CHOEt | |
| 12-5 | 1 | $CF_3$ | MeNHCO | N=CHOEt | 115–116 |
| 12-6 | 2 | $CF_3$ | MeNHCO | N=CHOEt | |
| 12-7 | 0 | $CF_3$ | MeNHCO | N=CHOPr-n | |
| 12-8 | 1 | $CF_3$ | MeNHCO | N=CHOPr-n | |
| 12-9 | 2 | $CF_3$ | MeNHCO | N=CHOPr-n | |
| 12-10 | 0 | $CF_3$ | MeNHCO | N=CHOPr-i | |
| 12-11 | 1 | $CF_3$ | MeNHCO | N=CHOPr-i | |
| 12-12 | 2 | $CF_3$ | MeNHCO | N=CHOPr-i | |
| 12-13 | 0 | $CF_3$ | MeNHCO | N=CHOBu-n | |
| 12-14 | 1 | $CF_3$ | MeNHCO | N=CHOBu-n | |
| 12-15 | 2 | $CF_3$ | MeNHCO | N=CHOBu-n | |
| 12-16 | 0 | $CF_3$ | MeNHCO | N=CHOBu-i | |
| 12-17 | 1 | $CF_3$ | MeNHCO | N=CHOBu-i | |
| 12-18 | 2 | $CF_3$ | MeNHCO | N=CHOBu-i | |
| 12-19 | 0 | $CF_3$ | MeNHCO | N=CHOBu-s | |
| 12-20 | 1 | $CF_3$ | MeNHCO | N=CHOBu-s | |
| 12-21 | 2 | $CF_3$ | MeNHCO | N=CHOBu-s | |
| 12-22 | 0 | $CF_3$ | MeNHCO | N=CHOBu-t | |
| 12-23 | 1 | $CF_3$ | MeNHCO | N=CHOBu-t | |
| 12-24 | 2 | $CF_3$ | MeNHCO | N=CHOBu-t | |
| 12-25 | 0 | $CF_3$ | MeNHCO | $NH_2$ | |
| 12-26 | 1 | $CF_3$ | MeNHCO | $NH_2$ | |
| 12-27 | 2 | $CF_3$ | MeNHCO | $NH_2$ | |

TABLE 13

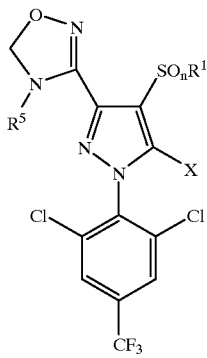

| Comp. No. | n | R¹ | R⁵ | X | mp. (° C.) |
|---|---|---|---|---|---|
| 13-1 | 0 | CF$_3$ | EtNHCO | N=CHOMe | |
| 13-2 | 1 | CF$_3$ | EtNHCO | N=CHOMe | |
| 13-3 | 2 | CF$_3$ | EtNHCO | N=CHOMe | |
| 13-4 | 0 | CF$_3$ | EtNHCO | N=CHOEt | |
| 13-5 | 1 | CF$_3$ | EtNHCO | N=CHOEt | 151–152 |
| 13-6 | 2 | CF$_3$ | EtNHCO | N=CHOEt | |
| 13-7 | 0 | CF$_3$ | EtNHCO | N=CHOPr-n | |
| 13-8 | 1 | CF$_3$ | EtNHCO | N=CHOPr-n | |
| 13-9 | 2 | CF$_3$ | EtNHCO | N=CHOPr-n | |
| 13-10 | 0 | CF$_3$ | EtNHCO | N=CHOPr-i | |
| 13-11 | 1 | CF$_3$ | EtNHCO | N=CHOPr-i | |
| 13-12 | 2 | CF$_3$ | EtNHCO | N=CHOPr-i | |
| 13-13 | 0 | CF$_3$ | EtNHCO | N=CHOBu-n | |
| 13-14 | 1 | CF$_3$ | EtNHCO | N=CHOBu-n | |
| 13-15 | 2 | CF$_3$ | EtNHCO | N=CHOBu-n | |
| 13-16 | 0 | CF$_3$ | EtNHCO | N=CHOBu-i | |
| 13-17 | 1 | CF$_3$ | EtNHCO | N=CHOBu-i | |
| 13-18 | 2 | CF$_3$ | EtNHCO | N=CHOBu-i | |
| 13-19 | 0 | CF$_3$ | EtNHCO | N=CHOBu-s | |
| 13-20 | 1 | CF$_3$ | EtNHCO | N=CHOBu-s | |
| 13-21 | 2 | CF$_3$ | EtNHCO | N=CHOBu-s | |
| 13-22 | 0 | CF$_3$ | EtNHCO | N=CHOBu-t | |
| 13-23 | 1 | CF$_3$ | EtNHCO | N=CHOBu-t | |
| 13-24 | 2 | CF$_3$ | EtNHCO | N=CHOBu-t | |
| 13-25 | 0 | CF$_3$ | EtNHCO | NH$_2$ | |
| 13-26 | 1 | CF$_3$ | EtNHCO | NH$_2$ | |
| 13-27 | 2 | CF$_3$ | EtNHCO | NH$_2$ | |

TABLE 14

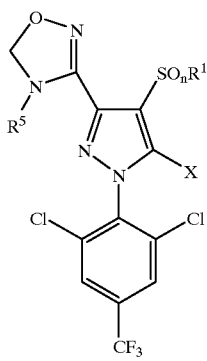

| Comp. No. | n | R¹ | R⁵ | X | mp. (° C.) |
|---|---|---|---|---|---|
| 14-1 | 0 | CF$_3$ | n-PrNHCO | N=CHOMe | |
| 14-2 | 1 | CF$_3$ | n-PrNHCO | N=CHOMe | |
| 14-3 | 2 | CF$_3$ | n-PrNHCO | N=CHOMe | |
| 14-4 | 0 | CF$_3$ | n-PrNHCO | N=CHOEt | |
| 14-5 | 1 | CF$_3$ | n-PrNHCO | N=CHOEt | 151–152 |
| 14-6 | 2 | CF$_3$ | n-PrNHCO | N=CHOEt | |

TABLE 14-continued

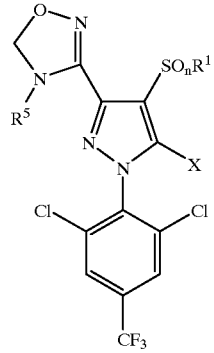

| Comp. No. | n | R¹ | R⁵ | X | mp. (° C.) |
|---|---|---|---|---|---|
| 14-7 | 0 | CF$_3$ | n-PrNHCO | N=CHOPr-n | |
| 14-8 | 1 | CF$_3$ | n-PrNHCO | N=CHOPr-n | |
| 14-9 | 2 | CF$_3$ | n-PrNHCO | N=CHOPr-n | |
| 14-10 | 0 | CF$_3$ | n-PrNHCO | N=CHOPr-i | |
| 14-11 | 1 | CF$_3$ | n-PrNHCO | N=CHOPr-i | |
| 14-12 | 2 | CF$_3$ | n-PrNHCO | N=CHOPr-i | |
| 14-13 | 0 | CF$_3$ | n-PrNHCO | N=CHOBu-n | |
| 14-14 | 1 | CF$_3$ | n-PrNHCO | N=CHOBu-n | |
| 14-15 | 2 | CF$_3$ | n-PrNHCO | N=CHOBu-n | |
| 14-16 | 0 | CF$_3$ | n-PrNHCO | N=CHOBu-i | |
| 14-17 | 1 | CF$_3$ | n-PrNHCO | N=CHOBu-i | |
| 14-18 | 2 | CF$_3$ | n-PrNHCO | N=CHOBu-i | |
| 14-19 | 0 | CF$_3$ | n-PrNHCO | N=CHOBu-s | |
| 14-20 | 1 | CF$_3$ | n-PrNHCO | N=CHOBu-s | |
| 14-21 | 2 | CF$_3$ | n-PrNHCO | N=CHOBu-s | |
| 14-22 | 0 | CF$_3$ | n-PrNHCO | N=CHOBu-t | |
| 14-23 | 1 | CF$_3$ | n-PrNHCO | N=CHOBu-t | |
| 14-24 | 2 | CF$_3$ | n-PrNHCO | N=CHOBu-t | |
| 14-25 | 0 | CF$_3$ | n-PrNHCO | NH$_2$ | |
| 14-26 | 1 | CF$_3$ | n-PrNHCO | NH$_2$ | |
| 14-27 | 2 | CF$_3$ | n-PrNHCO | NH$_2$ | |

TABLE 15

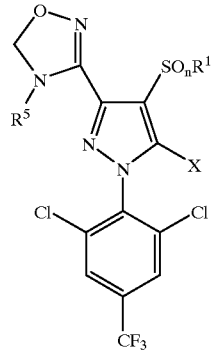

| Comp. No. | n | R¹ | R⁵ | X | mp. (° C.) |
|---|---|---|---|---|---|
| 15-1 | 0 | CF$_3$ | i-PrNHCO | N=CHOMe | |
| 15-2 | 1 | CF$_3$ | i-PrNHCO | N=CHOMe | |
| 15-3 | 2 | CF$_3$ | i-PrNHCO | N=CHOMe | |
| 15-4 | 0 | CF$_3$ | i-PrNHCO | N=CHOEt | |
| 15-5 | 1 | CF$_3$ | i-PrNHCO | N=CHOEt | 160–162 |
| 15-6 | 2 | CF$_3$ | i-PrNHCO | N=CHOEt | |
| 15-7 | 0 | CF$_3$ | i-PrNHCO | N=CHOPr-n | |
| 15-8 | 1 | CF$_3$ | i-PrNHCO | N=CHOPr-n | |
| 15-9 | 2 | CF$_3$ | i-PrNHCO | N=CHOPr-n | |
| 15-10 | 0 | CF$_3$ | i-PrNHCO | N=CHOPr-i | |
| 15-11 | 1 | CF$_3$ | i-PrNHCO | N=CHOPr-i | |
| 15-12 | 2 | CF$_3$ | i-PrNHCO | N=CHOPr-i | |

TABLE 15-continued

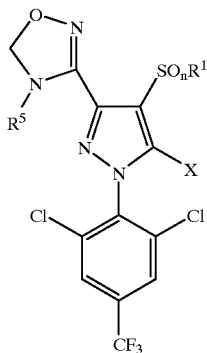

| Comp. No. | n | R¹ | R⁵ | X | mp. (° C.) |
|---|---|---|---|---|---|
| 15-13 | 0 | CF₃ | i-PrNHCO | N=CHOBu-n | |
| 15-14 | 1 | CF₃ | i-PrNHCO | N=CHOBu-n | |
| 15-15 | 2 | CF₃ | i-PrNHCO | N=CHOBu-n | |
| 15-16 | 0 | CF₃ | i-PrNHCO | N=CHOBu-i | |
| 15-17 | 1 | CF₃ | i-PrNHCO | N=CHOBu-i | |
| 15-18 | 2 | CF₃ | i-PrNHCO | N=CHOBu-i | |
| 15-19 | 0 | CF₃ | i-PrNHCO | N=CHOBu-s | |
| 15-20 | 1 | CF₃ | i-PrNHCO | N=CHOBu-s | |
| 15-21 | 2 | CF₃ | i-PrNHCO | N=CHOBu-s | |
| 15-22 | 0 | CF₃ | i-PrNHCO | N=CHOBu-t | |
| 15-23 | 1 | CF₃ | i-PrNHCO | N=CHOBu-t | |
| 15-24 | 2 | CF₃ | i-PrNHCO | N=CHOBu-t | |
| 15-25 | 0 | CF₃ | i-PrNHCO | NH₂ | |
| 15-26 | 1 | CF₃ | i-PrNHCO | NH₂ | |
| 15-27 | 2 | CF₃ | i-PrNHCO | NH₂ | |

TABLE 16

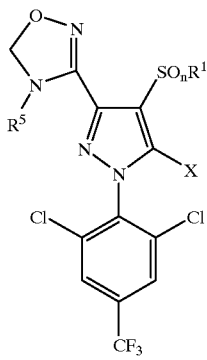

| Comp. No. | n | R¹ | R⁵ | X | mp. (° C.) |
|---|---|---|---|---|---|
| 16-1 | 0 | CF₃ | n-BuNHCO | N=CHOMe | |
| 16-2 | 1 | CF₃ | n-BuNHCO | N=CHOMe | |
| 16-3 | 2 | CF₃ | n-BuNHCO | N=CHOMe | |
| 16-4 | 0 | CF₃ | n-BuNHCO | N=CHOEt | |
| 16-5 | 1 | CF₃ | n-BuNHCO | N=CHOEt | 127–128 |
| 16-6 | 2 | CF₃ | n-BuNHCO | N=CHOEt | |
| 16-7 | 0 | CF₃ | n-BuNHCO | N=CHOPr-n | |
| 16-8 | 1 | CF₃ | n-BuNHCO | N=CHOPr-n | |
| 16-9 | 2 | CF₃ | n-BuNHCO | N=CHOPr-n | |
| 16-10 | 0 | CF₃ | n-BuNHCO | N=CHOPr-i | |
| 16-11 | 1 | CF₃ | n-BuNHCO | N=CHOPr-i | |
| 16-12 | 2 | CF₃ | n-BuNHCO | N=CHOPr-i | |
| 16-13 | 0 | CF₃ | n-BuNHCO | N=CHOBu-n | |
| 16-14 | 1 | CF₃ | n-BuNHCO | N=CHOBu-n | |
| 16-15 | 2 | CF₃ | n-BuNHCO | N=CHOBu-n | |
| 16-16 | 0 | CF₃ | n-BuNHCO | N=CHOBu-i | |
| 16-17 | 1 | CF₃ | n-BuNHCO | N=CHOBu-i | |
| 16-18 | 2 | CF₃ | n-BuNHCO | N=CHOBu-i | |

TABLE 16-continued

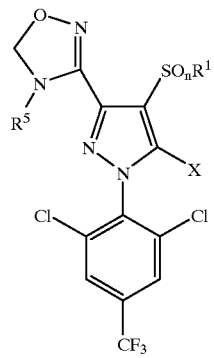

| Comp. No. | n | R¹ | R⁵ | X | mp. (° C.) |
|---|---|---|---|---|---|
| 16-19 | 0 | CF₃ | n-BuNHCO | N=CHOBu-s | |
| 16-20 | 1 | CF₃ | n-BuNHCO | N=CHOBu-s | |
| 16-21 | 2 | CF₃ | n-BuNHCO | N=CHOBu-s | |
| 16-22 | 0 | CF₃ | n-BuNHCO | N=CHOBu-t | |
| 16-23 | 1 | CF₃ | n-BuNHCO | N=CHOBu-t | |
| 16-24 | 2 | CF₃ | n-BuNHCO | N=CHOBu-t | |
| 16-25 | 0 | CF₃ | n-BuNHCO | NH₂ | |
| 16-26 | 1 | CF₃ | n-BuNHCO | NH₂ | |
| 16-27 | 2 | CF₃ | n-BuNHCO | NH₂ | |

TABLE 17

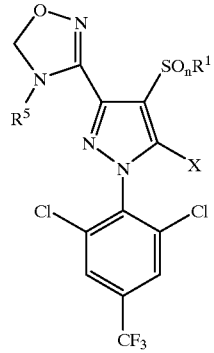

| Comp. No. | n | R¹ | R⁵ | X | mp. (° C.) |
|---|---|---|---|---|---|
| 17-1 | 0 | CF₃ | i-BuNHCO | N=CHOMe | |
| 17-2 | 1 | CF₃ | i-BuNHCO | N=CHOMe | |
| 17-3 | 2 | CF₃ | i-BuNHCO | N=CHOMe | |
| 17-4 | 0 | CF₃ | i-BuNHCO | N=CHOEt | |
| 17-5 | 1 | CF₃ | i-BuNHCO | N=CHOEt | |
| 17-6 | 2 | CF₃ | i-BuNHCO | N=CHOEt | |
| 17-7 | 0 | CF₃ | i-BuNHCO | N=CHOPr-n | |
| 17-8 | 1 | CF₃ | i-BuNHCO | N=CHOPr-n | |
| 17-9 | 2 | CF₃ | i-BuNHCO | N=CHOPr-n | |
| 17-10 | 0 | CF₃ | i-BuNHCO | N=CHOPr-i | |
| 17-11 | 1 | CF₃ | i-BuNHCO | N=CHOPr-i | |
| 17-12 | 2 | CF₃ | i-BuNHCO | N=CHOPr-i | |
| 17-13 | 0 | CF₃ | i-BuNHCO | N=CHOBu-n | |
| 17-14 | 1 | CF₃ | i-BuNHCO | N=CHOBu-n | |
| 17-15 | 2 | CF₃ | i-BuNHCO | N=CHOBu-n | |
| 17-16 | 0 | CF₃ | i-BuNHCO | N=CHOBu-i | |
| 17-17 | 1 | CF₃ | i-BuNHCO | N=CHOBu-i | |
| 17-18 | 2 | CF₃ | i-BuNHCO | N=CHOBu-i | |
| 17-19 | 0 | CF₃ | i-BuNHCO | N=CHOBu-s | |
| 17-20 | 1 | CF₃ | i-BuNHCO | N=CHOBu-s | |
| 17-21 | 2 | CF₃ | i-BuNHCO | N=CHOBu-s | |
| 17-22 | 0 | CF₃ | i-BuNHCO | N=CHOBu-t | |
| 17-23 | 1 | CF₃ | i-BuNHCO | N=CHOBu-t | |
| 17-24 | 2 | CF₃ | i-BuNHCO | N=CHOBu-t | |

TABLE 17-continued

Structure: oxadiazoline-pyrazole with 2,6-dichloro-4-trifluoromethylphenyl substituent, SO$_n$R$^1$ and X groups, R$^5$ on oxadiazoline N.

| Comp. No. | n | R$^1$ | R$^5$ | X | mp. (° C.) |
|---|---|---|---|---|---|
| 17-25 | 0 | CF$_3$ | i-BuNHCO | NH$_2$ | |
| 17-26 | 1 | CF$_3$ | i-BuNHCO | NH$_2$ | 215–217 |
| 17-27 | 2 | CF$_3$ | i-BuNHCO | NH$_2$ | |

TABLE 18

| Comp. No. | n | R$^1$ | R$^5$ | X | mp. (° C.) |
|---|---|---|---|---|---|
| 18-1 | 0 | CF$_3$ | t-BuNHCO | N=CHOMe | |
| 18-2 | 1 | CF$_3$ | t-BuNHCO | N=CHOMe | |
| 18-3 | 2 | CF$_3$ | t-BuNHCO | N=CHOMe | |
| 18-4 | 0 | CF$_3$ | t-BuNHCO | N=CHOEt | |
| 18-5 | 1 | CF$_3$ | t-BuNHCO | N=CHOEt | 120–121 |
| 18-6 | 2 | CF$_3$ | t-BuNHCO | N=CHOEt | |
| 18-7 | 0 | CF$_3$ | t-BuNHCO | N=CHOPr-n | |
| 18-8 | 1 | CF$_3$ | t-BuNHCO | N=CHOPr-n | |
| 18-9 | 2 | CF$_3$ | t-BuNHCO | N=CHOPr-n | |
| 18-10 | 0 | CF$_3$ | t-BuNHCO | N=CHOPr-i | |
| 18-11 | 1 | CF$_3$ | t-BuNHCO | N=CHOPr-i | |
| 18-12 | 2 | CF$_3$ | t-BuNHCO | N=CHOPr-i | |
| 18-13 | 0 | CF$_3$ | t-BuNHCO | N=CHOBu-n | |
| 18-14 | 1 | CF$_3$ | t-BuNHCO | N=CHOBu-n | |
| 18-15 | 2 | CF$_3$ | t-BuNHCO | N=CHOBu-n | |
| 18-16 | 0 | CF$_3$ | t-BuNHCO | N=CHOBu-i | |
| 18-17 | 1 | CF$_3$ | t-BuNHCO | N=CHOBu-i | |
| 18-18 | 2 | CF$_3$ | t-BuNHCO | N=CHOBu-i | |
| 18-19 | 0 | CF$_3$ | t-BuNHCO | N=CHOBu-s | |
| 18-20 | 1 | CF$_3$ | t-BuNHCO | N=CHOBu-s | |
| 18-21 | 2 | CF$_3$ | t-BuNHCO | N=CHOBu-s | |
| 18-22 | 0 | CF$_3$ | t-BuNHCO | N=CHOBu-t | |
| 18-23 | 1 | CF$_3$ | t-BuNHCO | N=CHOBu-t | |
| 18-24 | 2 | CF$_3$ | t-BuNHCO | N=CHOBu-t | |
| 18-25 | 0 | CF$_3$ | t-BuNHCO | NH$_2$ | |
| 18-26 | 1 | CF$_3$ | t-BuNHCO | NH$_2$ | |
| 18-27 | 2 | CF$_3$ | t-BuNHCO | NH$_2$ | |

TABLE 19

| Comp. No. | n | R$^1$ | R$^5$ | X | mp. (° C.) |
|---|---|---|---|---|---|
| 19-1 | 0 | CF$_3$ | s-BuNHCO | N=CHOMe | |
| 19-2 | 1 | CF$_3$ | s-BuNHCO | N=CHOMe | |
| 19-3 | 2 | CF$_3$ | s-BuNHCO | N=CHOMe | |
| 19-4 | 0 | CF$_3$ | s-BuNHCO | N=CHOEt | |
| 19-5 | 1 | CF$_3$ | s-BuNHCO | N=CHOEt | |
| 19-6 | 2 | CF$_3$ | s-BuNHCO | N=CHOEt | |
| 19-7 | 0 | CF$_3$ | s-BuNHCO | N=CHOPr-n | |
| 19-8 | 1 | CF$_3$ | s-BuNHCO | N=CHOPr-n | |
| 19-9 | 2 | CF$_3$ | s-BuNHCO | N=CHOPr-n | |
| 19-10 | 0 | CF$_3$ | s-BuNHCO | N=CHOPr-i | |
| 19-11 | 1 | CF$_3$ | s-BuNHCO | N=CHOPr-i | |
| 19-12 | 2 | CF$_3$ | s-BuNHCO | N=CHOPr-i | |
| 19-13 | 0 | CF$_3$ | s-BuNHCO | N=CHOBu-n | |
| 19-14 | 1 | CF$_3$ | s-BuNHCO | N=CHOBu-n | |
| 19-15 | 2 | CF$_3$ | s-BuNHCO | N=CHOBu-n | |
| 19-16 | 0 | CF$_3$ | s-BuNHCO | N=CHOBu-i | |
| 19-17 | 1 | CF$_3$ | s-BuNHCO | N=CHOBu-i | |
| 19-18 | 2 | CF$_3$ | s-BuNHCO | N=CHOBu-i | |
| 19-19 | 0 | CF$_3$ | s-BuNHCO | N=CHOBu-s | |
| 19-20 | 1 | CF$_3$ | s-BuNHCO | N=CHOBu-s | |
| 19-21 | 2 | CF$_3$ | s-BuNHCO | N=CHOBu-s | |
| 19-22 | 0 | CF$_3$ | s-BuNHCO | N=CHOBu-t | |
| 19-23 | 1 | CF$_3$ | s-BuNHCO | N=CHOBu-t | |
| 19-24 | 2 | CF$_3$ | s-BuNHCO | N=CHOBu-t | |
| 19-25 | 0 | CF$_3$ | s-BuNHCO | NH$_2$ | |
| 19-26 | 1 | CF$_3$ | s-BuNHCO | NH$_2$ | |
| 19-27 | 2 | CF$_3$ | s-BuNHCO | NH$_2$ | |

TABLE 20

| Comp. No. | n | R$^1$ | R$^5$ | X | mp. (° C.) |
|---|---|---|---|---|---|
| 20-1 | 0 | CF$_3$ | Me$_2$NCO | N=CHOMe | |
| 20-2 | 1 | CF$_3$ | Me$_2$NCO | N=CHOMe | 158–158.5 |
| 20-3 | 2 | CF$_3$ | Me$_2$NCO | N=CHOMe | |
| 20-4 | 0 | CF$_3$ | Me$_2$NCO | N=CHOEt | 93–94 |
| 20-5 | 1 | CF$_3$ | Me$_2$NCO | N=CHOEt | (amorphous)[5)] |
| 20-6 | 2 | CF$_3$ | Me$_2$NCO | N=CHOEt | 102–103 |

TABLE 20-continued

| Comp. No. | n | R¹ | R⁵ | X | mp. (° C.) |
|---|---|---|---|---|---|
| 20-7 | 0 | $CF_3$ | $Me_2NCO$ | N=CHOPr-n | 51–54 |
| 20-8 | 1 | $CF_3$ | $Me_2NCO$ | N=CHOPr-n | |
| 20-9 | 2 | $CF_3$ | $Me_2NCO$ | N=CHOPr-n | |
| 20-10 | 0 | $CF_3$ | $Me_2NCO$ | N=CHOPr-i | 112–113 |
| 20-11 | 1 | $CF_3$ | $Me_2NCO$ | N=CHOPr-i | 114–116[6] |
| 20-12 | 2 | $CF_3$ | $Me_2NCO$ | N=CHOPr-i | (amorphous)[7] |
| 20-13 | 0 | $CF_3$ | $Me_2NCO$ | N=CHOBu-n | (amorphous)[8] |
| 20-14 | 1 | $CF_3$ | $Me_2NCO$ | N=CHOBu-n | 130–131 |
| 20-15 | 2 | $CF_3$ | $Me_2NCO$ | N=CHOBu-n | 96.5–97.5 |
| 20-16 | 0 | $CF_3$ | $Me_2NCO$ | N=CHOBu-i | |
| 20-17 | 1 | $CF_3$ | $Me_2NCO$ | N=CHOBu-i | |
| 20-18 | 2 | $CF_3$ | $Me_2NCO$ | N=CHOBu-i | |
| 20-19 | 0 | $CF_3$ | $Me_2NCO$ | N=CHOBu-s | |
| 20-20 | 1 | $CF_3$ | $Me_2NCO$ | N=CHOBu-s | |
| 20-21 | 2 | $CF_3$ | $Me_2NCO$ | N=CHOBu-s | |
| 20-22 | 0 | $CF_3$ | $Me_2NCO$ | N=CHOBu-t | |
| 20-23 | 1 | $CF_3$ | $Me_2NCO$ | N=CHOBu-t | |
| 20-24 | 2 | $CF_3$ | $Me_2NCO$ | N=CHOBu-t | |
| 20-25 | 0 | $CF_3$ | $Me_2NCO$ | $NH_2$ | 191–193 |
| 20-26 | 1 | $CF_3$ | $Me_2NCO$ | $NH_2$ | 207–207.5 |
| 20-27 | 2 | $CF_3$ | $Me_2NCO$ | $NH_2$ | 240.5–241 |

TABLE 21

| Comp. No. | n | R¹ | R⁵ | X | mp. (° C.) |
|---|---|---|---|---|---|
| 21-1 | 0 | $CF_3$ | $Et_2NCO$ | N=CHOMe | |
| 21-2 | 1 | $CF_3$ | $Et_2NCO$ | N=CHOMe | |
| 21-3 | 2 | $CF_3$ | $Et_2NCO$ | N=CHOMe | |
| 21-4 | 0 | $CF_3$ | $Et_2NCO$ | N=CHOEt | 93–95 |
| 21-5 | 1 | $CF_3$ | $Et_2NCO$ | N=CHOEt | 107–108 |
| 21-6 | 2 | $CF_3$ | $Et_2NCO$ | N=CHOEt | 105.5–106.5 |
| 21-7 | 0 | $CF_3$ | $Et_2NCO$ | N=CHOPr-n | 100–102 |
| 21-8 | 1 | $CF_3$ | $Et_2NCO$ | N=CHOPr-n | (oil)[9] |
| 21-9 | 2 | $CF_3$ | $Et_2NCO$ | N=CHOPr-n | (oil)[10] |
| 21-10 | 0 | $CF_3$ | $Et_2NCO$ | N=CHOPr-i | (amorphous)[11] |
| 21-11 | 1 | $CF_3$ | $Et_2NCO$ | N=CHOPr-i | 106–107 |
| 21-12 | 2 | $CF_3$ | $Et_2NCO$ | N=CHOPr-i | (amorphous)[12] |

TABLE 21-continued

| Comp. No. | n | R¹ | R⁵ | X | mp. (° C.) |
|---|---|---|---|---|---|
| 21-13 | 0 | $CF_3$ | $Et_2NCO$ | N=CHOBu-n | (oil)[13] |
| 21-14 | 1 | $CF_3$ | $Et_2NCO$ | N=CHOBu-n | 104.5–105 |
| 21-15 | 2 | $CF_3$ | $Et_2NCO$ | N=CHOBu-n | (oil)[14] |
| 21-16 | 0 | $CF_3$ | $Et_2NCO$ | N=CHOBu-i | |
| 21-17 | 1 | $CF_3$ | $Et_2NCO$ | N=CHOBu-i | |
| 21-18 | 2 | $CF_3$ | $Et_2NCO$ | N=CHOBu-i | |
| 21-19 | 0 | $CF_3$ | $Et_2NCO$ | N=CHOBu-s | |
| 21-20 | 1 | $CF_3$ | $Et_2NCO$ | N=CHOBu-s | |
| 21-21 | 2 | $CF_3$ | $Et_2NCO$ | N=CHOBu-s | |
| 21-22 | 0 | $CF_3$ | $Et_2NCO$ | N=CHOBu-t | |
| 21-23 | 1 | $CF_3$ | $Et_2NCO$ | N=CHOBu-t | |
| 21-24 | 2 | $CF_3$ | $Et_2NCO$ | N=CHOBu-t | |
| 21-25 | 0 | $CF_3$ | $Et_2NCO$ | $NH_2$ | 81–83 |
| 21-26 | 1 | $CF_3$ | $Et_2NCO$ | $NH_2$ | 98–99 |
| 21-27 | 2 | $CF_3$ | $Et_2NCO$ | $NH_2$ | 197–198 |

TABLE 22

| Comp. No. | n | R¹ | R⁵ | X | mp. (° C.) |
|---|---|---|---|---|---|
| 22-1 | 0 | $CF_3$ | MeEtNCO | N=CHOMe | |
| 22-2 | 1 | $CF_3$ | MeEtNCO | N=CHOMe | |
| 22-3 | 2 | $CF_3$ | MeEtNCO | N=CHOMe | |
| 22-4 | 0 | $CF_3$ | MeEtNCO | N=CHOEt | 83–85 |
| 22-5 | 1 | $CF_3$ | MeEtNCO | N=CHOEt | 113–114 |
| 22-6 | 2 | $CF_3$ | MeEtNCO | N=CHOEt | (amorphous)[15] |
| 22-7 | 0 | $CF_3$ | MeEtNCO | N=CHOPr-n | |
| 22-8 | 1 | $CF_3$ | MeEtNCO | N=CHOPr-n | |
| 22-9 | 2 | $CF_3$ | MeEtNCO | N=CHOPr-n | |
| 22-10 | 0 | $CF_3$ | MeEtNCO | N=CHOPr-i | (oil)[16] |
| 22-11 | 1 | $CF_3$ | MeEtNCO | N=CHOPr-i | 126–128 |
| 22-12 | 2 | $CF_3$ | MeEtNCO | N=CHOPr-i | (amorphous)[17] |
| 22-13 | 0 | $CF_3$ | MeEtNCO | N=CHOBu-n | (oil)[18] |
| 22-14 | 1 | $CF_3$ | MeEtNCO | N=CHOBu-n | 126–126.5 |
| 22-15 | 2 | $CF_3$ | MeEtNCO | N=CHOBu-n | (oil)[19] |
| 22-16 | 0 | $CF_3$ | MeEtNCO | N=CHOBu-i | |
| 22-17 | 1 | $CF_3$ | MeEtNCO | N=CHOBu-i | |
| 22-18 | 2 | $CF_3$ | MeEtNCO | N=CHOBu-i | |

TABLE 22-continued

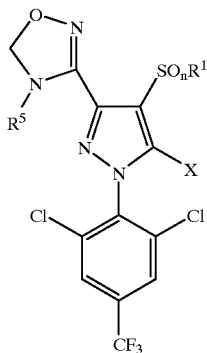

| Comp. No. | n | R¹ | R⁵ | X | mp. (° C.) |
|---|---|---|---|---|---|
| 22-19 | 0 | CF₃ | MeEtNCO | N=CHOBu-s | |
| 22-20 | 1 | CF₃ | MeEtNCO | N=CHOBu-s | |
| 22-21 | 2 | CF₃ | MeEtNCO | N=CHOBu-s | |
| 22-22 | 0 | CF₃ | MeEtNCO | N=CHOBu-t | |
| 22-23 | 1 | CF₃ | MeEtNCO | N=CHOBu-t | |
| 22-24 | 2 | CF₃ | MeEtNCO | N=CHOBu-t | |
| 22-25 | 0 | CF₃ | MeEtNCO | NH₂ | 141–143 |
| 22-26 | 1 | CF₃ | MeEtNCO | NH₂ | 165–166 |
| 22-27 | 2 | CF₃ | MeEtNCO | NH₂ | 215–215.5 |

TABLE 23

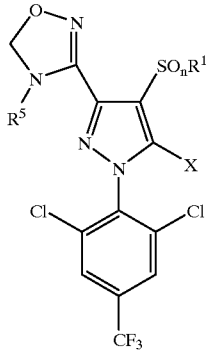

| Comp. No | n | R¹ | R⁵ | X | mp. (° C.) |
|---|---|---|---|---|---|
| 23-1 | 0 | CF₃ | (EtO)₂CH | N=CHOMe | |
| 23-2 | 1 | CF₃ | (EtO)₂CH | N=CHOMe | |
| 23-3 | 2 | CF₃ | (EtO)₂CH | N=CHOMe | |
| 23-4 | 0 | CF₃ | (EtO)₂CH | N=CHOEt | |
| 23-5 | 1 | CF₃ | (EtO)₂CH | N=CHOEt | |
| 23-6 | 2 | CF₃ | (EtO)₂CH | N=CHOEt | |
| 23-7 | 0 | CF₃ | (EtO)₂CH | N=CHOPr-n | |
| 23-8 | 1 | CF₃ | (EtO)₂CH | N=CHOPr-n | |
| 23-9 | 2 | CF₃ | (EtO)₂CH | N=CHOPr-n | |
| 23-10 | 0 | CF₃ | (EtO)₂CH | N=CHOPr-i | |
| 23-11 | 1 | CF₃ | (EtO)₂CH | N=CHOPr-i | |
| 23-12 | 2 | CF₃ | (EtO)₂CH | N=CHOPr-i | |
| 23-13 | 0 | CF₃ | (EtO)₂CH | N=CHOBu-n | |
| 23-14 | 1 | CF₃ | (EtO)₂CH | N=CHOBu-n | |
| 23-15 | 2 | CF₃ | (EtO)₂CH | N=CHOBu-n | |
| 23-16 | 0 | CF₃ | (EtO)₂CH | N=CHOBu-i | |
| 23-17 | 1 | CF₃ | (EtO)₂CH | N=CHOBu-i | |
| 23-18 | 2 | CF₃ | (EtO)₂CH | N=CHOBu-i | |
| 23-19 | 0 | CF₃ | (EtO)₂CH | N=CHOBu-s | |
| 23-20 | 1 | CF₃ | (EtO)₂CH | N=CHOBu-s | |
| 23-21 | 2 | CF₃ | (EtO)₂CH | N=CHOBu-s | |
| 23-22 | 0 | CF₃ | (EtO)₂CH | N=CHOBu-t | |
| 23-23 | 1 | CF₃ | (EtO)₂CH | N=CHOBu-t | |
| 23-24 | 2 | CF₃ | (EtO)₂CH | N=CHOBu-t | |

TABLE 23-continued

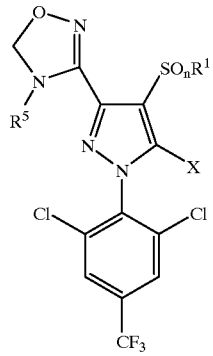

| Comp. No | n | R¹ | R⁵ | X | mp. (° C.) |
|---|---|---|---|---|---|
| 23-25 | 0 | CF₃ | (EtO)₂CH | NH₂ | |
| 23-26 | 1 | CF₃ | (EtO)₂CH | NH₂ | |
| 23-27 | 2 | CF₃ | (EtO)₂CH | NH₂ | 218–220 |

TABLE 24

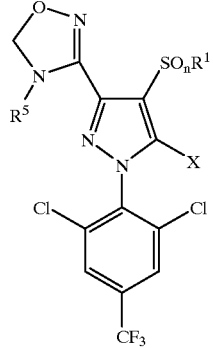

| Comp. No. | n | R¹ | R⁵ | X | mp. (° C.) |
|---|---|---|---|---|---|
| 24-1 | 0 | CF₃ | (ⁱPrO)₂CH | N=CHOMe | |
| 24-2 | 1 | CF₃ | (ⁱPrO)₂CH | N=CHOMe | |
| 24-3 | 2 | CF₃ | (ⁱPrO)₂CH | N=CHOMe | |
| 24-4 | 0 | CF₃ | (ⁱPrO)₂CH | N=CHOEt | |
| 24-5 | 1 | CF₃ | (ⁱPrO)₂CH | N=CHOEt | 95–97 |
| 24-6 | 2 | CF₃ | (ⁱPrO)₂CH | N=CHOEt | |
| 24-7 | 0 | CF₃ | (ⁱPrO)₂CH | N=CHOPr-n | |
| 24-8 | 1 | CF₃ | (ⁱPrO)₂CH | N=CHOPr-n | |
| 24-9 | 2 | CF₃ | (ⁱPrO)₂CH | N=CHOPr-n | |
| 24-10 | 0 | CF₃ | (ⁱPrO)₂CH | N=CHOPr-i | |
| 24-11 | 1 | CF₃ | (ⁱPrO)₂CH | N=CHOPr-i | |
| 24-12 | 2 | CF₃ | (ⁱPrO)₂CH | N=CHOPr-i | |
| 24-13 | 0 | CF₃ | (ⁱPrO)₂CH | N=CHOBu-n | |
| 24-14 | 1 | CF₃ | (ⁱPrO)₂CH | N=CHOBu-n | |
| 24-15 | 2 | CF₃ | (ⁱPrO)₂CH | N=CHOBu-n | |
| 24-16 | 0 | CF₃ | (ⁱPrO)₂CH | N=CHOBu-i | |
| 24-17 | 1 | CF₃ | (ⁱPrO)₂CH | N=CHOBu-i | |
| 24-18 | 2 | CF₃ | (ⁱPrO)₂CH | N=CHOBu-i | |
| 24-19 | 0 | CF₃ | (ⁱPrO)₂CH | N=CHOBu-s | |
| 24-20 | 1 | CF₃ | (ⁱPrO)₂CH | N=CHOBu-s | |
| 24-21 | 2 | CF₃ | (ⁱPrO)₂CH | N=CHOBu-s | |
| 24-22 | 0 | CF₃ | (ⁱPrO)₂CH | N=CHOBu-t | |
| 24-23 | 1 | CF₃ | (ⁱPrO)₂CH | N=CHOBu-t | |
| 24-24 | 2 | CF₃ | (ⁱPrO)₂CH | N=CHOBu-t | |
| 24-25 | 0 | CF₃ | (ⁱPrO)₂CH | NH₂ | |
| 24-26 | 1 | CF₃ | (ⁱPrO)₂CH | NH₂ | |
| 24-27 | 2 | CF₃ | (ⁱPrO)₂CH | NH₂ | 173–176 |

TABLE 25

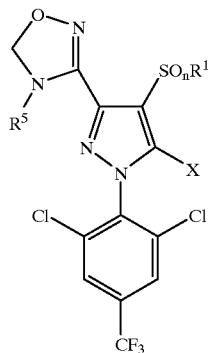

| Comp. No. | n | $R^1$ | $R^5$ | X | mp. (° C.) |
|---|---|---|---|---|---|
| 25-1 | 0 | $CF_3$ | Me | N=CHOMe | |
| 25-2 | 1 | $CF_3$ | Me | N=CHOMe | |
| 25-3 | 2 | $CF_3$ | Me | N=CHOMe | |
| 25-4 | 0 | $CF_3$ | Me | N=CHOEt | |
| 25-5 | 1 | $CF_3$ | Me | N=CHOEt | |
| 25-6 | 2 | $CF_3$ | Me | N=CHOEt | |
| 25-7 | 0 | $CF_3$ | Me | N=CHOPr-n | |
| 25-8 | 1 | $CF_3$ | Me | N=CHOPr-n | |
| 25-9 | 2 | $CF_3$ | Me | N=CHOPr-n | |
| 25-10 | 0 | $CF_3$ | Me | N=CHOPr-i | |
| 25-11 | 1 | $CF_3$ | Me | N=CHOPr-i | |
| 25-12 | 2 | $CF_3$ | Me | N=CHOPr-i | |
| 25-13 | 0 | $CF_3$ | Me | N=CHOBu-n | |
| 25-14 | 1 | $CF_3$ | Me | N=CHOBu-n | |
| 25-15 | 2 | $CF_3$ | Me | N=CHOBu-n | |
| 25-16 | 0 | $CF_3$ | Me | N=CHOBu-i | |
| 25-17 | 1 | $CF_3$ | Me | N=CHOBu-i | |
| 25-18 | 2 | $CF_3$ | Me | N=CHOBu-i | |
| 25-19 | 0 | $CF_3$ | Me | N=CHOBu-s | |
| 25-20 | 1 | $CF_3$ | Me | N=CHOBu-s | |
| 25-21 | 2 | $CF_3$ | Me | N=CHOBu-s | |
| 25-22 | 0 | $CF_3$ | Me | N=CHOBu-t | |
| 25-23 | 1 | $CF_3$ | Me | N=CHOBu-t | |
| 25-24 | 2 | $CF_3$ | Me | N=CHOBu-t | |
| 25-25 | 0 | $CF_3$ | Me | $NH_2$ | |
| 25-26 | 1 | $CF_3$ | Me | $NH_2$ | |
| 25-27 | 2 | $CF_3$ | Me | $NH_2$ | |

TABLE 26

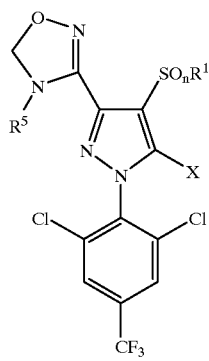

| Comp. No. | n | $R^1$ | $R^5$ | X | mp. (° C.) |
|---|---|---|---|---|---|
| 26-1 | 0 | $CF_3$ | Et | N=CHOMe | |
| 26-2 | 1 | $CF_3$ | Et | N=CHOMe | |
| 26-3 | 2 | $CF_3$ | Et | N=CHOMe | |
| 26-4 | 0 | $CF_3$ | Et | N=CHOEt | |
| 26-5 | 1 | $CF_3$ | Et | N=CHOEt | |
| 26-6 | 2 | $CF_3$ | Et | N=CHOEt | |
| 26-7 | 0 | $CF_3$ | Et | N=CHOPr-n | |
| 26-8 | 1 | $CF_3$ | Et | N=CHOPr-n | |
| 26-9 | 2 | $CF_3$ | Et | N=CHOPr-n | |
| 26-10 | 0 | $CF_3$ | Et | N=CHOPr-i | |
| 26-11 | 1 | $CF_3$ | Et | N=CHOPr-i | |
| 26-12 | 2 | $CF_3$ | Et | N=CHOPr-i | |
| 26-13 | 0 | $CF_3$ | Et | N=CHOBu-n | |
| 26-14 | 1 | $CF_3$ | Et | N=CHOBu-n | |
| 26-15 | 2 | $CF_3$ | Et | N=CHOBu-n | |
| 26-16 | 0 | $CF_3$ | Et | N=CHOBu-i | |
| 26-17 | 1 | $CF_3$ | Et | N=CHOBu-i | |
| 26-18 | 2 | $CF_3$ | Et | N=CHOBu-i | |
| 26-19 | 0 | $CF_3$ | Et | N=CHOBu-s | |
| 26-20 | 1 | $CF_3$ | Et | N=CHOBu-s | |
| 26-21 | 2 | $CF_3$ | Et | N=CHOBu-s | |
| 26-22 | 0 | $CF_3$ | Et | N=CHOBu-t | |
| 26-23 | 1 | $CF_3$ | Et | N=CHOBu-t | |
| 26-24 | 2 | $CF_3$ | Et | N=CHOBu-t | |
| 26-25 | 0 | $CF_3$ | Et | $NH_2$ | |
| 26-26 | 1 | $CF_3$ | Et | $NH_2$ | (amorphous)[20] |
| 26-27 | 2 | $CF_3$ | Et | $NH_2$ | |

TABLE 27

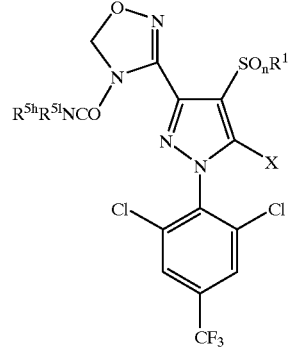

| Comp. No. | n | $R^1$ | $R^{5h}$ | $R^{5i}$ | X | mp. (° C.) |
|---|---|---|---|---|---|---|
| 27-1 | 0 | $CF_3$ | Me | n-Pr | N=CHOEt | |
| 27-2 | 1 | $CF_3$ | Me | n-Pr | N=CHOEt | |
| 27-3 | 2 | $CF_3$ | Me | n-Pr | N=CHOEt | 106–108 |
| 27-4 | 0 | $CF_3$ | Me | i-Pr | N=CHOEt | 126–128 |
| 27-5 | 1 | $CF_3$ | Me | i-Pr | N=CHOEt | 96–98 |
| 27-6 | 2 | $CF_3$ | Me | i-Pr | N=CHOEt | (oil)[21] |
| 27-7 | 0 | $CF_3$ | Me | n-Bu | N=CHOEt | |
| 27-8 | 1 | $CF_3$ | Me | n-Bu | N=CHOEt | 82–83 |
| 27-9 | 2 | $CF_3$ | Me | n-Bu | N=CHOEt | |
| 27-10 | 0 | $CF_3$ | Me | i-Bu | N=CHOEt | |
| 27-11 | 1 | $CF_3$ | Me | i-Bu | N=CHOEt | 102–103 |
| 27-12 | 2 | $CF_3$ | Me | i-Bu | N=CHOEt | |

TABLE 27-continued

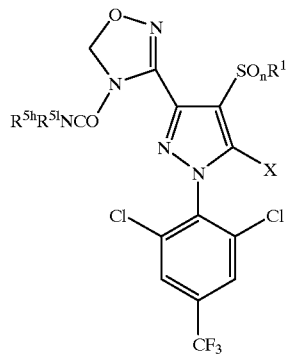

| Comp. No. | n | $R^1$ | $R^{5h}$ | $R^{5l}$ | X | mp. (° C.) |
|---|---|---|---|---|---|---|
| 27-13 | 0 | $CF_3$ | Me | s-Bu | N=CHOEt | |
| 27-14 | 1 | $CF_3$ | Me | s-Bu | N=CHOEt | |
| 27-15 | 2 | $CF_3$ | Me | s-Bu | N=CHOEt | |
| 27-16 | 0 | $CF_3$ | Me | t-Bu | N=CHOEt | (oil)[22] |
| 27-17 | 1 | $CF_3$ | Me | t-Bu | N=CHOEt | (amorphous)[23] |
| 27-18 | 2 | $CF_3$ | Me | t-Bu | N=CHOEt | (amorphous)[24] |
| 27-19 | 0 | $CF_3$ | Et | n-Pr | N=CHOEt | |
| 27-20 | 1 | $CF_3$ | Et | n-Pr | N=CHOEt | 101–102 |

TABLE 27-continued

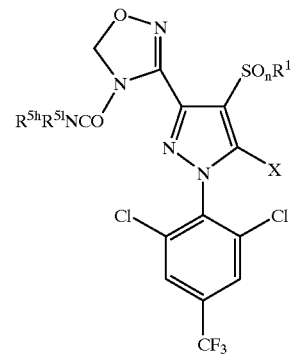

| Comp. No. | n | $R^1$ | $R^{5h}$ | $R^{5l}$ | X | mp. (° C.) |
|---|---|---|---|---|---|---|
| 27-21 | 2 | $CF_3$ | Et | n-Pr | N=CHOEt | |
| 27-22 | 0 | $CF_3$ | Et | i-Pr | N=CHOEt | |
| 27-23 | 1 | $CF_3$ | Et | i-Pr | N=CHOEt | (amorphous)[25] |
| 27-24 | 2 | $CF_3$ | Et | i-Pr | N=CHOEt | |
| 27-25 | 0 | $CF_3$ | Et | n-Bu | N=CHOEt | |
| 27-26 | 1 | $CF_3$ | Et | n-Bu | N=CHOEt | 84–85 |
| 27-27 | 2 | $CF_3$ | Et | n-Bu | N=CHOEt | |

TABLE 28

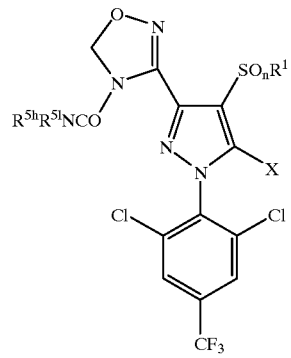

| Comp. No. | n | $R^1$ | $R^{5h}$ | $R^{5l}$ | X | mp. (° C.) |
|---|---|---|---|---|---|---|
| 28-1 | 0 | $CF_3$ | Et | i-Bu | N=CHOEt | |
| 28-2 | 1 | $CF_3$ | Et | i-Bu | N=CHOEt | |
| 28-3 | 2 | $CF_3$ | Et | i-Bu | N=CHOEt | |
| 28-4 | 0 | $CF_3$ | Et | s-Bu | N=CHOEt | |
| 28-5 | 1 | $CF_3$ | Et | s-Bu | N=CHOEt | |
| 28-6 | 2 | $CF_3$ | Et | s-Bu | N=CHOEt | |
| 28-7 | 0 | $CF_3$ | Et | t-Bu | N=CHOEt | |
| 28-8 | 1 | $CF_3$ | Et | t-Bu | N=CHOEt | 113–114 |
| 28-9 | 2 | $CF_3$ | Et | t-Bu | N=CHOEt | |
| 28-10 | 0 | $CF_3$ | n-Pr | n-Pr | N=CHOEt | |
| 28-11 | 1 | $CF_3$ | n-Pr | n-Pr | N=CHOEt | 109–111 |
| 28-12 | 2 | $CF_3$ | n-Pr | n-Pr | N=CHOEt | |
| 28-13 | 0 | $CF_3$ | n-Bu | n-Bu | N=CHOEt | |
| 28-14 | 1 | $CF_3$ | n-Bu | n-Bu | N=CHOEt | 97–98 |
| 28-15 | 2 | $CF_3$ | n-Bu | n-Bu | N=CHOEt | |
| 28-16 | 0 | $CF_3$ | i-Bu | i-Bu | N=CHOEt | |
| 28-17 | 1 | $CF_3$ | i-Bu | i-Bu | N=CHOEt | 114–115 |
| 28-18 | 2 | $CF_3$ | i-Bu | i-Bu | N=CHOEt | |
| 28-19 | 0 | $CF_3$ | H | $CH_2CH=CH_2$ | N=CHOEt | |

TABLE 28-continued

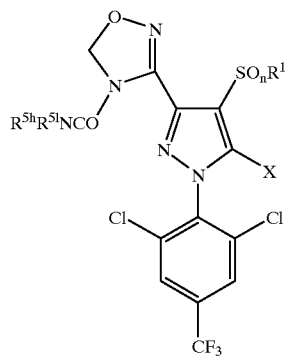

| Comp. No. | n | R¹ | $R^{5h}$ | $R^{5l}$ | X | mp. (° C.) |
|---|---|---|---|---|---|---|
| 28-20 | 1 | CF₃ | H | CH₂CH=CH₂ | N=CHOEt | 140–142 |
| 28-21 | 2 | CF₃ | H | CH₂CH=CH₂ | N=CHOEt | |
| 28-22 | 0 | CF₃ | Me | CH₂CH=CH₂ | N=CHOEt | |
| 28-23 | 1 | CF₃ | Me | CH₂CH=CH₂ | N=CHOEt | (oil)[26] |
| 28-24 | 2 | CF₃ | Me | CH₂CH=CH₂ | N=CHOEt | |
| 28-25 | 0 | CF₃ | CH₂CH=CH₂ | CH₂CH=CH₂ | N=CHOEt | |
| 28-26 | 1 | CF₃ | CH₂CH=CH₂ | CH₂CH=CH₂ | N=CHOEt | 132–133 |
| 28-27 | 2 | CF₃ | CH₂CH=CH₂ | CH₂CH=CH₂ | N=CHOEt | |

TABLE 29

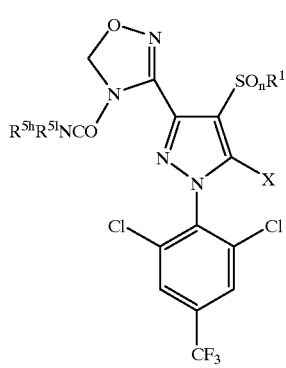

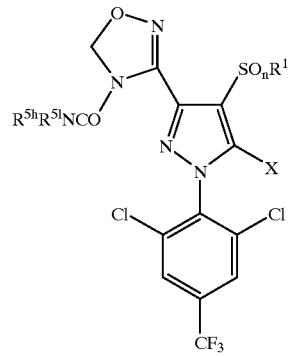

| Comp. No. | n | R¹ | $R^{5h}$ | $R^{5l}$ | X | mp. (° C.) |
|---|---|---|---|---|---|---|
| 29-1 | 0 | CF₃ | H | CH₂C≡CH | N=CHOEt | |
| 29-2 | 1 | CF₃ | H | CH₂C≡CH | N=CHOEt | 126–128 |
| 29-3 | 2 | CF₃ | H | CH₂C≡CH | N=CHOEt | |
| 29-4 | 0 | CF₃ | CH₂C≡CH | CH₂C≡CH | N=CHOEt | |
| 29-5 | 1 | CF₃ | CH₂C≡CH | CH₂C≡CH | N=CHOEt | 122–124 |
| 29-6 | 2 | CF₃ | CH₂C≡CH | CH₂C≡CH | N=CHOEt | |
| 29-7 | 0 | CF₃ | H | Ph | N=CHOEt | |
| 29-8 | 1 | CF₃ | H | Ph | N=CHOEt | 146–148 |
| 29-9 | 2 | CF₃ | H | Ph | N=CHOEt | |
| 29-10 | 0 | CF₃ | Me | Ph | N=CHOEt | |
| 29-11 | 1 | CF₃ | Me | Ph | N=CHOEt | 154–155 |
| 29-12 | 2 | CF₃ | Me | Ph | N=CHOEt | |
| 29-13 | 0 | CF₃ | Me | CH₂Ph | N=CHOEt | |
| 29-14 | 1 | CF₃ | Me | CH₂Ph | N=CHOEt | 124–126 |
| 29-15 | 2 | CF₃ | Me | CH₂Ph | N=CHOEt | |
| 29-16 | 0 | CF₃ | H | Me₂N | N=CHOEt | |
| 29-17 | 1 | CF₃ | H | Me₂N | N=CHOEt | 135–136 |
| 29-18 | 2 | CF₃ | H | Me₂N | N=CHOEt | |
| 29-19 | 0 | CF₃ | Et | EtNH | N=CHOEt | |
| 29-20 | 1 | CF₃ | Et | EtNH | N=CHOEt | (oil)[27] |
| 29-21 | 2 | CF₃ | Et | EtNH | N=CHOEt | |
| 29-22 | 0 | CF₃ | H | OH | N=CHOEt | |
| 29-23 | 1 | CF₃ | H | OH | N=CHOEt | (oil)[28] |
| 29-24 | 2 | CF₃ | H | OH | N=CHOEt | |
| 29-25 | 0 | CF₃ | H | OMe | N=CHOEt | |
| 29-26 | 1 | CF₃ | H | OMe | N=CHOEt | (oil)[29] |
| 29-27 | 2 | CF₃ | H | OMe | N=CHOEt | |

TABLE 30

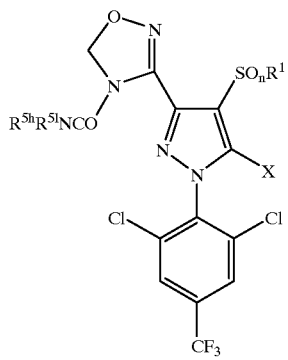

| Comp. No. | n | R$^1$ | R$^{5h}$ | R$^{5l}$ | X | mp. (° C.) |
|---|---|---|---|---|---|---|
| 30-1 | 0 | CF$_3$ | Me | OH | N=CHOEt | |
| 30-2 | 1 | CF$_3$ | Me | OH | N=CHOEt | (oil)[30] |
| 30-3 | 2 | CF$_3$ | Me | OH | N=CHOEt | |
| 30-4 | 0 | CF$_3$ | Me | OMe | N=CHOEt | |
| 30-5 | 1 | CF$_3$ | Me | OMe | N=CHOEt | 131.5–132.5 |
| 30-6 | 2 | CF$_3$ | Me | OMe | N=CHOEt | |
| 30-7 | 0 | CF$_3$ | Me | —⟨cyclohexyl⟩ | N=CHOEt | |
| 30-8 | 1 | CF$_3$ | Me | —⟨cyclohexyl⟩ | N=CHOEt | (amorphous)[31] |
| 30-9 | 2 | CF$_3$ | Me | —⟨cyclohexyl⟩ | N=CHOEt | |
| 30-10 | 0 | CF$_3$ | Et | —⟨cyclohexyl⟩ | N=CHOEt | |
| 30-11 | 1 | CF$_3$ | Et | —⟨cyclohexyl⟩ | N=CHOEt | 86–88 |

TABLE 30-continued

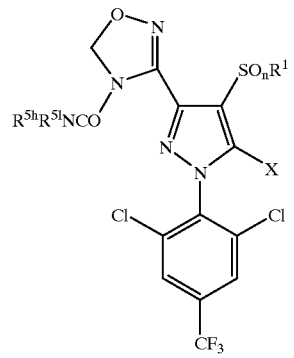

| Comp. No. | n | R$^1$ | R$^{5h}$ | R$^{5l}$ | X | mp. (° C.) |
|---|---|---|---|---|---|---|
| 30-12 | 2 | CF$_3$ | Et | —⟨cyclohexyl⟩ | N=CHOEt | |
| 30-13 | 0 | CF$_3$ | | —(CH$_2$)$_4$— | N=CHOEt | |
| 30-14 | 1 | CF$_3$ | | —(CH$_2$)$_4$— | N=CHOEt | 155–157 |
| 30-15 | 2 | CF$_3$ | | —(CH$_2$)$_4$— | N=CHOEt | |
| 30-16 | 0 | CF$_3$ | | —(CH$_2$)$_5$— | N=CHOEt | |
| 30-17 | 1 | CF$_3$ | | —(CH$_2$)$_5$— | N=CHOEt | (amorphous)[32] |
| 30-18 | 2 | CF$_3$ | | —(CH$_2$)$_5$— | N=CHOEt | |
| 30-19 | 0 | CF$_3$ | | —(CH$_2$)$_6$— | N=CHOEt | |
| 30-20 | 1 | CF$_3$ | | —(CH$_2$)$_6$— | N=CHOEt | 97–99 |
| 30-21 | 2 | CF$_3$ | | —(CH$_2$)$_6$— | N=CHOEt | |
| 30-22 | 0 | CF$_3$ | | —(CH$_2$)$_2$NMe(CH$_2$)$_2$— | N=CHOEt | |
| 30-23 | 1 | CF$_3$ | | —(CH$_2$)$_2$NMe(CH$_2$)$_2$— | N=CHOEt | (amorphous)[33] |
| 30-24 | 2 | CF$_3$ | | —(CH$_2$)$_2$NMe(CH$_2$)$_2$— | N=CHOEt | |
| 30-25 | 0 | CF$_3$ | | —(CH$_2$)$_2$O(CH$_2$)$_2$— | N=CHOEt | |
| 30-26 | 1 | CF$_3$ | | —(CH$_2$)$_2$O(CH$_2$)$_2$— | N=CHOEt | (amorphous)[34] |
| 30-27 | 2 | CF$_3$ | | —(CH$_2$)$_2$O(CH$_2$)$_2$— | N=CHOEt | |

TABLE 31

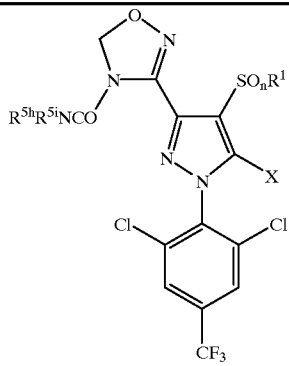

| Comp. No. | n | R$^1$ | R$^{5h}$ | R$^{5i}$ | X | mp. (° C.) |
|---|---|---|---|---|---|---|
| 31-1 | 0 | CF$_3$ | H | —⟨N-methylpiperidinyl⟩ | N=CHOEt | |

TABLE 31-continued

| Comp. No. | n | R¹ | R⁵ʰ | R⁵ⁱ | X | mp. (° C.) |
|---|---|---|---|---|---|---|
| 31-2 | 1 | CF₃ | H | N-methylpiperidinyl | N=CHOEt | 179~180 |
| 31-3 | 2 | CF₃ | H | N-methylpiperidinyl | N=CHOEt | |
| 31-4 | 0 | CF₃ | Me | Me | N=CHNMe₂ | |
| 31-5 | 1 | CF₃ | Me | Me | N=CHNMe₂ | 174~175 |
| 31-6 | 2 | CF₃ | Me | Me | N=CHNMe₂ | |
| 31-7 | 0 | CF₃ | Et | Et | N=CHNMe₂ | |
| 31-8 | 1 | CF₃ | Et | Et | N=CHNMe₂ | 156~158 |
| 31-9 | 2 | CF₃ | Et | Et | N=CHNMe₂ | |
| 31-10 | 1 | CF₃ | Et | Et | NHMe | 127~128 |
| 31-11 | 1 | CF₃ | Me | Me | NMe₂ | 176~178 |
| 31-12 | 0 | CF₃ | Me | Me | N=CH-(3-OMe-4-OH-phenyl) | 166~168 |
| 31-13 | 1 | CF₃ | Me | Me | N=CH-(3-OMe-4-OH-phenyl) | 174~175 |
| 31-14 | 1 | CF₃ | Et | Et | N=CH-(3-OMe-4-OH-phenyl) | (amorphous)⁴⁵⁾ |
| 31-15 | 1 | CF₃ | Me | Me | N-methylpyrrolyl | 244~246 |
| 31-16 | 1 | CF₃ | Me | Me | NHCH₂-(4-pyridyl) | (amorphous)⁴⁶⁾ |
| 31-17 | 1 | CF₃ | Et | Pr-i | NH₂ | 168~170 |
| 31-18 | 1 | CF₃ | Et | Me₂NCH₂CH₂ | N=CHOEt | 104~105.5 |
| 31-19 | 1 | CF₃ | H | CF₃CH₂ | NH₂ | 224~226 |

TABLE 32

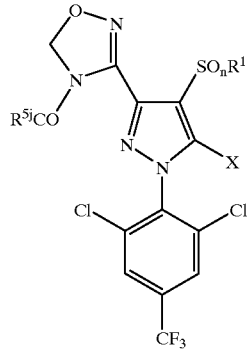

| Comp. No. | n | R¹ | R⁵ʲ | X | mp. (° C.) |
|---|---|---|---|---|---|
| 32-1 | 0 | CF₃ | n-C₅H₁₁ | N=CHOEt | |
| 32-2 | 1 | CF₃ | n-C₅H₁₁ | N=CHOEt | 94.0–94.5 |
| 32-3 | 2 | CF₃ | n-C₅H₁₁ | N=CHOEt | |
| 32-4 | 0 | CF₃ | n-C₆H₁₃ | N=CHOEt | |
| 32-5 | 1 | CF₃ | n-C₆H₁₃ | N=CHOEt | 92.5–93 |
| 32-6 | 2 | CF₃ | n-C₆H₁₃ | N=CHOEt | |
| 32-7 | 0 | CF₃ | n-C₇H₁₅ | N=CHOEt | |
| 32-8 | 1 | CF₃ | n-C₇H₁₅ | N=CHOEt | 73–74 |
| 32-9 | 2 | CF₃ | n-C₇H₁₅ | N=CHOEt | |
| 32-10 | 0 | CF₃ | n-C₈H₁₇ | N=CHOEt | |
| 32-11 | 1 | CF₃ | n-C₈H₁₇ | N=CHOEt | (oil)³⁵⁾ |
| 32-12 | 2 | CF₃ | n-C₈H₁₇ | N=CHOEt | |
| 32-13 | 0 | CF₃ | n-C₉H₁₉ | N=CHOEt | |
| 32-14 | 1 | CF₃ | n-C₉H₁₉ | N=CHOEt | (oil)³⁶⁾ |
| 32-15 | 2 | CF₃ | n-C₉H₁₉ | N=CHOEt | |
| 32-16 | 0 | CF₃ | Et₂CH | N=CHOEt | |
| 32-17 | 1 | CF₃ | Et₂CH | N=CHOEt | (oil)³⁷⁾ |
| 32-18 | 2 | CF₃ | Et₂CH | N=CHOEt | |
| 32-19 | 0 | CF₃ | n-Pr₂CH | N=CHOEt | |
| 32-20 | 1 | CF₃ | n-Pr₂CH | N=CHOEt | 94–95 |
| 32-21 | 2 | CF₃ | n-Pr₂CH | N=CHOEt | |
| 32-22 | 0 | CF₃ | t-BuCH₂ | N=CHOEt | |
| 32-23 | 1 | CF₃ | t-BuCH₂ | N=CHOEt | (amorphous)³⁸⁾ |
| 32-24 | 2 | CF₃ | t-BuCH₂ | N=CHOEt | |
| 32-25 | 0 | CF₃ | cyclopropyl | N=CHOEt | |
| 32-26 | 1 | CF₃ | cyclopropyl | N=CHOEt | 125–126 |
| 32-27 | 2 | CF₃ | cyclopropyl | N=CHOEt | |

TABLE 33

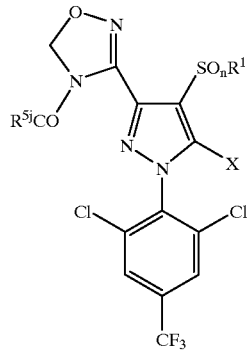

| Comp. No. | n | R¹ | R⁵ʲ | X | mp. (° C.) |
|---|---|---|---|---|---|
| 33-1 | 0 | CF₃ | cyclohexyl | N=CHOEt | |
| 33-2 | 1 | CF₃ | cyclohexyl | N=CHOEt | 91–92 |
| 33-3 | 2 | CF₃ | cyclohexyl | N=CHOEt | |
| 33-4 | 0 | CF₃ | —CH=CH₂ | N=CHOEt | |
| 33-5 | 1 | CF₃ | —CH=CH₂ | N=CHOEt | 52–53 |
| 33-6 | 2 | CF₃ | —CH=CH₂ | N=CHOEt | |
| 33-7 | 0 | CF₃ | —CH=CHMe | N=CHOEt | |
| 33-8 | 1 | CF₃ | —CH=CHMe | N=CHOEt | 112–113 |
| 33-9 | 2 | CF₃ | —CH=CHMe | N=CHOEt | |
| 33-10 | 0 | CF₃ | —CH=CHPh | N=CHOEt | |
| 33-11 | 1 | CF₃ | —CH=CHPh | N=CHOEt | (amorphous)³⁹⁾ |
| 33-12 | 2 | CF₃ | —CH=CHPh | N=CHOEt | |
| 33-13 | 0 | CF₃ | CH₂CH₂Ph | N=CHOEt | |
| 33-14 | 1 | CF₃ | CH₂CH₂Ph | N=CHOEt | 115–116 |
| 33-15 | 2 | CF₃ | CH₂CH₂Ph | N=CHOEt | |
| 33-16 | 0 | CF₃ | CH₂OMe | N=CHOEt | |
| 33-17 | 1 | CF₃ | CH₂OMe | N=CHOEt | 96–97 |
| 33-18 | 2 | CF₃ | CH₂OMe | N=CHOEt | |
| 33-19 | 0 | CF₃ | CH₂CF₃ | N=CHOEt | |
| 33-20 | 1 | CF₃ | CH₂CF₃ | N=CHOEt | 161–162 |
| 33-21 | 2 | CF₃ | CH₂CF₃ | N=CHOEt | |
| 33-23 | 0 | CF₃ | H | N=CHOEt | |
| 33-24 | 1 | CF₃ | H | N=CHOEt | 151–152 |
| 33-25 | 2 | CF₃ | H | N=CHOEt | |

TABLE 34

| Comp. No. | n | R¹ | R⁵ʲ | X | mp. (° C.) |
|---|---|---|---|---|---|
| 34-1 | 0 | CF₃ | MeO | N=CHOEt | |
| 34-2 | 1 | CF₃ | MeO | N=CHOEt | (oil)⁴⁰⁾ |
| 34-3 | 2 | CF₃ | MeO | N=CHOEt | |
| 34-4 | 0 | CF₃ | EtO | N=CHOEt | |
| 34-5 | 1 | CF₃ | EtO | N=CHOEt | (oil)⁴¹⁾ |
| 34-6 | 2 | CF₃ | EtO | N=CHOEt | |
| 34-7 | 0 | CF₃ | i-PrO | N=CHOEt | |
| 34-8 | 1 | CF₃ | i-PrO | N=CHOEt | (oil)⁴²⁾ |
| 34-9 | 2 | CF₃ | i-PrO | N=CHOEt | |
| 34-10 | 0 | CF₃ | t-BuO | N=CHOEt | 102–103 |
| 34-11 | 1 | CF₃ | t-BuO | N=CHOEt | (amorphous)⁴³⁾ |
| 34-12 | 2 | CF₃ | t-BuO | N=CHOEt | (amorphous)⁴⁴⁾ |

TABLE 35

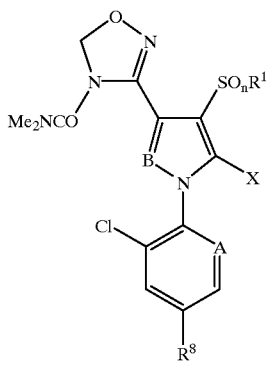

| Comp. No. | n | R¹ | R⁸ | A | B | X | mp. (° C.) |
|---|---|---|---|---|---|---|---|
| 35-1 | 1 | CF₃ | Cl | CCl | N | N=CHOPr-i | (oil)⁴⁷⁾ |
| 35-2 | 1 | CF₃ | OCF₃ | CCl | N | NH₂ | 110~114 |
| 35-3 | 1 | CF₃ | CF₃ | N | N | NH₂ | (amorphous)⁴⁸⁾ |
| 35-4 | 1 | CF₃ | CF₃ | CCN | N | N=CHOEt | |
| 35-5 | 1 | CF₃ | –C₆H₄–CF₃ | | CCl | N | N=CHOEt | |
| 35-6 | 1 | CF₃ | CF₃ | CCl | C | N=CHOEt | |

TABLE 36

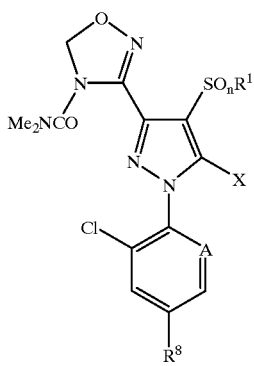

| Comp. No. | n | R¹ | R⁸ | A | X | mp. (° C.) |
|---|---|---|---|---|---|---|
| 36-1 | 0 | Et | CF₃ | CCl | NH₂ | 187.0–189.0 |
| 36-2 | 1 | Et | CF₃ | CCl | NH₂ | 223.0–225.0 |
| 36-3 | 2 | Et | CF₃ | CCl | NH₂ | 203.0–205.0 |
| 36-4 | 1 | CF₃ | OCF₃ | CCl | N=CHOPr-i | 105.0–105.6 |
| 36-5 | 0 | CF₃ | CF₃ | N | NH₂ | 123.0–124.5 |

$^1$H-NMR spectra of the oil and amorphous compounds in Tables 1 to 36 are shown below.

1) NMR(CDCl₃, δ) 1.09 (6H,d,J=7 Hz), 1.25 (3H,t,J=7 Hz), 2.61 (1H,qu,J=7 Hz), 4.16 (2H,q,J=7 Hz), 5.93 (2H,s), 7.76 (2H,s), 8.37 (1H,s)
2) NMR(CDCl₃, δ) 1.10 (6H,d,J=8 Hz), 1.22 (3H,t,J=7 Hz), 2.80 (1H,m), 4.12 (2H,m), 5.81 (1H,d,J=3 Hz), 6.00 (1H,d,J=3 Hz), 7.76 (2H,s), 8.60 (1H,s)
3) NMR(CDCl₃, δ) 0.83 (3H,t,J=8 Hz), 1.08 (3H,d,J=7 Hz), 1.25 (3H,t,J=7 Hz), 1.30–1.80 (1H,m), 2.44 (2H,q,J=7 Hz), 4.16 (2H,g,J=7 Hz), 5.87 (1H,d,J=2 Hz), 6.00 (1H,d,J=2 Hz), 7.75 (2H,s), 8.37 (1H,s)
4) NMR(CDCl₃, δ) 1.23 (3H,t,J=7 Hz), 1.31 (9H,s), 2.44 (2H,q,J=7 Hz), 4.14 (2H,q,J=7 Hz), 5.84 (2H,s), 7.71(2H, s), 8.34(1H,s)
5) NMR(CDCl₃, δ) 1.20 (3H,t,J=7 Hz), 2.94 (6H,s), 4.10 (2H,m), 5.51 (1H,d,J=2 Hz), 5.58 (1H,d,J=2 Hz), 7.72 (2H,m), 8.56(1H,s)
6) NMR(CDCl₃, δ) 1.10 (3H,d,J=6 Hz), 1.23 (3H,d,J=6 Hz), 2.95(6H,s),4.84 (1H,qu,J=6 Hz), 5.51 (1H,d,J=2 Hz), 5.59 (1H,d,J=2 Hz), 7.73 (2H,s), 8.56 (1H,s)
7) NMR(CDCl₃, δ) 1.19 (6H,d,J=6 Hz), 2.92 (6H,s), 4.94 (1H,qu,J=6 Hz), 5.67 (2H,s), 7.75 (2H,s), 8.00 (1H,s)
8) NMR(CDCl₃, δ) 0.84 (3H,t,J=7 Hz), 1.20–1.40 (2H,m), 1.5–1.6 (2H,m), 2.95 (6H,s), 4.10 (2H,dt,J=1 Hz,6.6 Hz), 5.58 (2H,s), 7.71–7.72 (2H,m), 8.35 (1H,s)
9) NMR(CDCl₃, δ) 0.82 (3H,t,J=7 Hz), 1.14 (6H,t,J=7 Hz), 1.58 (2H,m), 3.30 (4H,q,J=7 Hz), 3.99 (2H,m), 5.48 (1H,d,J=1 Hz), 5.55 (1H,d,J=1 Hz), 7.72 (2H,m), 8.61 (1H,s)
10) NMR(CDCl₃, δ) 0.84 (3H,t,J=7 Hz), 1.16 (6H,t,J=7 Hz), 1.61 (2H,m), 3.27 (4H,q,J=7 Hz), 4.07 (2H,t,J=7 Hz), 5.63 (2H,s),7.74 (2H,s), 8.06 (1H,s)
11) NMR(CDCl₃, δ) 1.17 (6H,t,J=7 Hz), 1.90 (6H,d,J=6 Hz), 3.32 (4H,q,J=7 Hz), 4.93 (1H,qu,J=6 Hz), 5.55 (2H,s), 7.70(2H,s), 8.29(1H,s)
12) NMR(CDCl3, δ) 1.12–1.23 (12H,m), 3.28 (4H,q,J=7 Hz), 4.83–5.05(1H,m), 5.63(2H,s), 7.74(2H,s), 7.99(1H, s)
13) NMR(CDCl₃, δ) 0.84 (3H,t,J=7 Hz), 1.17 (6H,t,J=7 Hz), 1.25–1.40 (2H,m), 1.49–1.63 (2H,m), 3.32 (4H#q,J=7 Hz), 4.10 (2H,t,J=6 Hz), 5.55 (2H,s), 7.71 (2H,s), 8.36 (1H,s)
14) NMR(CDCl₃, δ) 0.84 (3H,t,J=7 Hz), 1.17 (6H,t,J=7 Hz), 1.22–1.36 (2H,m), 1.48–1.59 (2H,m), 3.28 (4H,q,J=7 Hz), 4.13 (2H,t,J=6 Hz), 5.64 (2H,s), 7.74 (2H,s), 8.05 (1H,s)
15) NMR(CDCl₃, δ) 1.17 (3H,t,J=7 Hz), 1.26 (3H,t,J=7 Hz), 2.90(3H,s), 3.30 (2H,q,J=7 Hz), 4.17 (2H,d,J=7 Hz), 5.65 (2H,s), 7.75 (2H,s), 8.05 (1H,s)

16) NMR(CDCl$_3$, δ) 1.26–1.14 (9H,m), 2.93 (3H,s), 3.33 (2H,q,J=7 Hz), 4.94 (1H,qu,J=6 Hz), 5.57 (2H,s), 7.71 (2H,s), 8.29 (1H,s)
17) NMR(CDCl$_3$, δ) 1.17 (3H,t,J=7 Hz), 1.19 (6H,d,J=6 Hz), 2.90 (3H,s), 3.29 (2H,q,J=7 Hz), 4.94 (1H,qu,J=6 Hz), 5.66 (2H,s), 7.75 (2H,s), 8.00 (1H,s)
18) NMR(CDCl$_3$, δ) 0.84 (3H,t,J=7 Hz), 1.33–1.14 (5H,m), 1.57 (2H,qu,J=6 Hz), 2.93 (3H,s), 3.33 (4H,q,J=7 Hz), 4.10 (2H,t,J=7 Hz), 5.57 (2H,s), 7.71 (2H,s), 8.35 (1H,s)
19) NMR(CDCl$_3$, δ) 0.83 (3H,t,J=7 Hz), 1.17 (3H,t,J=7 Hz), 1.25 (2H,m), 1.55 (2H,m), 2.89 (3H,s), 3.29 (2H,t,J=7 Hz), 4.13 (2H,t,J=7 Hz), 5.65 (2H,s), 7.74 (2H,s), 8.05 (1H,s)
20) NMR(CDCl$_3$, δ) 1.14 (3H,t,J=7 Hz), 3.4–3.7 (2H,m), 5.18 (2H,br), 5.38 (2H,d,J=7 Hz). 7.82 (2H,s)
21) NMR(CDCl$_3$, δ) 1.14 (6H,d,J=7 Hz), 1.23 (3H,t,J=7 Hz), 2.86 (3H,s), 4.17 (2H,q,J=7 Hz), 4.42 (1H,qu,J=7 Hz), 5.88 (2H,s), 7.74 (2H,s), 8.03 (1H,s)
22) NMR(CDCl$_3$, δ) 1.23 (3H,t,J=7 Hz), 1.36 (9H,s), 2.93 (3H,s), 4.07–4.19 (2H,m), 5.56 (2H,s), 7.71 (2H,s), 8.35 (1H,s)
23) NMR(CDCl$_3$, δ) 1.20 (3H,t,J=7 Hz), 1.35 (9H,s), 2.91 (3H,s), 4.00–4.19 (2H,m), 5.46 (1H,d,J=2 Hz), 5.57 (1H, d,J=2 Hz), 7.71–7.74 (2H,m), 8.60 (1H,s)
24) NMR(CDCl$_3$, δ) 1.23 (3H,t,J=7 Hz), 1.33 (9H,s), 4.17 (2H,q,J=7 Hz), 5.63 (2H,s), 7.75 (2H,s),8.06 (1H,s)
25) NMR(CDCl$_3$, δ) 1.12–1.26 (12H,m), 3.22 (2H,q,J=7 Hz), 4.00–4.20 (2H,m), 5.48 (1H,d,J=1 Hz), 5.54 (1H,d, J=1 Hz), 7.72–7.74 (2H,m), 8.59 (1H,s)
26) NMR(CDCl$_3$, δ) 1.20 (3H,t,J=7 Hz), 2.91.(3H,s), 4.03–3.73 (4H,m), 5.16 (1H,q,J=2 Hz), 5.23 (1H,d,J=2 Hz), 5.48 (2H,d,J=2 Hz), 5.58 (1H,d,J=2 Hz), 5.66–5.86 (1H,m), 7.74 (2H,s), 8.57 (1H,s)
27) NMR(CDCl$_3$, δ) 1.04 (3H,t,J=7 Hz), 1.14 (3H,t,J=7 Hz), 1.20 (3H,t,J=7 Hz), 2.85(2H,m), 3.52 (2H,m), 4.10 (2H, m), 5.66 (1H,d,J=2 Hz), 5.70 (1H,d,J=2 Hz), 7.71 (2H,m), 8.59 (1H,s)
28) NMR(CDCl$_3$, δ) 1.21 (3H,t,J=7 Hz), 3.99–4.26 (2H,m), 5.75 (1H,d,J=2 Hz), 5.99 (1H,d,J=2 Hz), 7.69 (1H,brs), 7.79 (2H,m), 8.51 (1H,s), 9.77 (1H,s)
29) NMR(CDCl$_3$, δ)1.21(3H,t,J=7 Hz),3.68(3H,s), 3.99–4.26 (2H,m), 5.80 (1H,d,J=2 Hz), 6.06 (1H,d,J=2 Hz), 7.81 (2H,s), 8.54 (1H,s), 9.90 (1H,s)
30) NMR(CDCl$_3$, δ) 1.21 (3H,t,J=7 Hz), 3.12 (3H,s), 3.98–4.25 (2H,m), 5.57 (1H,d,J=3 Hz), 5.71 (1H,d,J=3 Hz), 7.70–7.82 (2H,m), 8.06 (1H,brs), 8.45 (1H,s)
31) NMR(CDCl$_3$, δ) 1.20 (3H,t,J=7 Hz.), 1.00–1.50 (4H,m), 1.60–1.80 (6H,m), 2.83 (3H,s), 3.70,–3.90(1H,m), 4.00–4.20 (2H,m), 5.48 (1H,d,J=2 Hz), 5.55 (1H,d,J=2 Hz), 7.71–7.74 (2H,m), 8.58 (1H,s)
32) NMR(CDCl$_3$, δ) 1.20 (3H,t,J=7 Hz), 1.60 (6H,br), 3.30–3.40 (4H,m), 4.00–4.20 (2H,m), 5.49 (1H,d,J=2 Hz), 5.56 (1H,d,J=2 Hz), 7.72–7.75 (2H,m), 8.59 (1H,s)
33) NMR(CDCl$_3$, δ) 1.20 (3H,t,J=7 Hz), 2.25 (3H,s), 2.38 (4H,t,J=5 Hz), 3.46 (4H,t,J=5 Hz), 4.10 (2H,m), 5.59 (1H,d,J=2 Hz), 5.76 (1H,d,J=2 Hz), 7.73 (2H,m), 8.57 (1H,s)
34) NMR(CDCl$_3$, δ) 1.21 (3H,t,J=7 Hz), 3.42–3.47 (4H,m), 3.67 (4H,t,J=5 Hz), 4.00–4.20 (2H,m), 5.49 (1H,d,J=2 Hz), 5.57 (1H,d,J=2 Hz), 7.72–7.77 (2H,m), 8.57 (1H,s)
35) NMR(CDCl$_3$, δ) 0.81–1.67 (18H,m), 2.20–2.50 (2H,m), 3.98–4.27 (2H,m), 5.82 (1H,d,J=3 Hz), 6.00 (1H,d,J=3 Hz), 7.73–7.81 (2H,m), 8.61 (1H,s)
36) NMR(CDCl$_3$, δ) 0.81–1.67 (20H,m), 2.20–2.50 (2H,m), 3.98–4.27 (2H,m), 5.82 (1H,d,J=3 Hz), 6.00 (1H,d,J=3 Hz), 7.73–7.81 (2H,m), 8.61 (1H,s)
37) NMR(CDCl$_3$, δ) 1.22 (3H,t,J=7 Hz), 1.45–1.74 (4H,m), 2.55 (1H,m), 4.11 (2H,m), 5.81 (1H,d,J=3 Hz), 6.04 (1H,d,J=3 Hz), 7.76 (2H,m), 8.62 (1H,s)
38) NMR(CDCl$_3$, δ) 1.00 (9H,s), 1.22 (3H,t,J=7 Hz), 2.25 (1H,d,J=15.3 Hz), 2.31 (1H,d,J=15.3 Hz), 3.99–4.27 (2H, m), 5.81 (1H,d,J=3 Hz), 5.98 (1H,d,J=3 Hz), 7.73–7.81 (2H,m), 8.62(1H,s)
39) NMR(CDCl$_3$, δ) 1.21 (3H,t,J=7 Hz), 3.98–4.25 (2H,m), 5.98 (1H,d,J=3 Hz), 6.05 (1H,d,J=3 Hz), 6.47 (1H,d,J=15 Hz), 7.27–7.45 (5H,m), 7.63–7.71 (2H,m), 7.76 (1H,d,J=15 Hz),8.58(1H,s)
40) NMR(CDCl$_3$, δ) 1.22 (3H,t,J=7 Hz), 3.75 (3H,s), 3.98–4.26 (2H,m), 5.73 (1H,d,J=2 Hz), 5.86 (1H,d,J=2 Hz), 7.72–7.78 (2H,m), 8.60 (1H,s)
41) NMR(CDCl$_3$,,) 1.22 (3H,t,J=7 Hz), 1.24 (3H,t,J=7 Hz), 4.11 (2H,m), 5.73 (1H,d,J=2 Hz), 4.22 (2H,q,J=7 Hz), 5.76 (1H,d,J=2 Hz), 5.83 (1H,d,J=2 Hz), 7.75 (2H,m), 8.59 (1H,s)
42) NMR(CDCl$_3$, δ) 1.17–1.29 (9H,m), 3.98–4.27 (2H,m), 5.00 (1H,sep,J=6 Hz), 5.77 (1H,d,J=2 Hz), 5.80 (1H,d,J=2 Hz), 7.72–7.79 (2H,m), 8.59(1H,s)
43) NMR(CDCl$_3$, δ) 1.22 (3H,t,J=7 Hz), 1.45 (9H,s), 3.98–4.26 (2H,m), 5.73 (1H,d,J=2 Hz), 5.78 (1H,d,J=2 Hz), 7.72–7.78 (2H,m), 8.61(1H,s)
44) NMR(CDCl$_3$, δ) 1.24 (3H,t,J=7 Hz), 1.44 (9H,s), 4.17 (2H,q,J=7 Hz), 5.78 (2H,s), 7.76 (2H,m), 8.13 (1H,s)
45) NMR(CDCl$_3$, δ) 1.16 (6H,t,J=7 Hz), 3.32 (4H,q,J=7 Hz), 3.83 (3H,s), 5.51 (1H,d,J=1 Hz), 5.59 (1H,d,J=1 Hz), 6.14 (1H,s), 6.93 (1H,d,J=8 Hz), 7.18 (1H,d,J=2 Hz), 7.32 (1H,dd,J=1.8 Hz,8.2 Hz), 7.70–7.80 (2H,m), 9.12 (1H,s)
46) NMR(CDCl$_3$, δ) 2.92 (6H,s), 4.12 (2H,d,J=7.0 Hz), 5.44 (1H,d,J=2 Hz), 5.53 (1H,d,J=2 Hz), 6.90 (2H,d,J=6 Hz), 7.00 (1H,t,J=7 Hz),7.45 (1H,m), 7.55 (1H,m),8.40 (2H, d,J=6 Hz)
47) NMR(CDCl$_3$, δ) 1.13 (3H,d,J=6 Hz), 1.20 (3H,d,J=6 Hz), 2.93 (6H,s), 4.86 (1H,sep,J=6 Hz), 5.50 (1H,d,J=2 Hz), 5.58 (1H,d,J=2 Hz), 7.47 (2H,m), 8.50 (1H,s)
48) NMR(CDCl$_3$, δ) 2.99 (6H,s), 5.54 (2H,s), 5.77 (2H,brs), 8.17 (1H,m), 8.63 (1H,m)

Example 26

An emulsifiable concentrate is produced by sufficiently mixing the compound No. 1–5 (20% by weight), xylene (75% by weight) and polyoxyethylene glycol ether (Nonipol 85 (trade name)) (5% by weight).

Example 27

A wettable powder is produced by sufficiently mixing the compound No. 1–5 (30% by weight), sodium lignin sulfonate (5% by weight), polyoxyethylene glycol ether (Nonipol 85 (trade name)) (5% by weight), white carbon (30% by weight) and clay (30% by weight).

Example 28

A dust is produced by sufficiently mixing the compound No. 1–5 (3% by weight), white carbon (3% by weight) and clay (94% by weight).

Example 29

A granule is produced by mixing the compound No. 1–5 (10% by weight), sodium lignin sulfonate (5% by weight) and clay (85% by weight) with pulverizing, adding water and kneading them, followed by granulating and further drying.

Example 30

An insecticidal dust is produced by sufficiently mixing the compound No. 1–5 (1.275% by weight) cartap 52.2% by weight), white carbon (0.5% by weight) and clay (96.025% by weight).

Example 31

An insecticidal/fungicidal dust is produced by sufficiently mixing the compound No. 1–5 (1.275% by weight), validamycin (0.33% by weight), white carbon (0.5% by weight) and clay (97.895% by weight).

Example 32

An emulsifiable concentrate was produced by sufficiently mixing the compound No. 20-1 (5.5% by weight), NK98147TX [mixture of polyoxyethylene allyl phenyl ether, calcium alkylbenzene sulfonate and aromatic hydrocarbon (solvesso 100 (trade name))](7% by weight), and N-methylpyrrolidone (AGSOREX 1 (trade name))(87.5% by weight).

Example 33

A flowable concentrates was produced by sufficiently mixing the compound No. 20–11 (5.5% by weight), polyoxyethylene alkyl allyl ether(Noigen EA177(trade name)) (2% by weight), silica/alumina mixture (Aerosil COK84 (trade name))(2% by weight), xanthan gum (Rhodopol 23 (trade name)) (0.1% by weight), ethylene glycol (7% by weight), silicone emulsion defoaming agent (Anti-foam E-20) (0.2% by weight), n-butyl p-hydroxybenzoate (0.1% by weight) and ion-exchange water (83.1% by weight).

Test Example 1

Insecticidal Effect Against *Chilo suppressalis*

Five milligrams each of test compounds (designated by each compound number assigned to the compound prepared in the above-described Examples) were respectively dissolved in 0.5 ml of acetone containing Tween 20 (trade name) and diluted with a 3,000-fold aqueous solution of Dyne to a predetermined concentration (100 ppm). This solution was applied to the leaves and stems of young rice seedlings at the 2 to 3-leaf stage raised in a nursery box (planting of 6 to 7 stubs) at a rate of 20 ml/pot by a spray gun. After the solution was dried, the young rice seedlings were put into a test tube (i: 3 cm, h: 20 cm) together with 5 ml of tap water. After the relase of ten 3-instar larvae of *Chio suppressalis* to the test tube. The test tube was placed in an incubator (27° C.). After five days, the total of the dead larvae was counted and the damage of young rice seedlings was observed. The mortality was calculated by the following equation:

Mortality (%)=(number of the dead larvae/number of the applited larvae)×100.

The damage of young rice seadlings was evaluated according to the following criteria:

Damage Criteria

0 The damage is scarcely recognized.

1 The damage is slightly recognized (not more than about 1/10 of non-treated young seedlings).

2 The damage is recognized less than about ½ of non-treated young seedlings.

3 The damage is recognized not less than about ½ of non-treated young seedlings.

4 The damage equivalent to non-treated young seedlings is recognized.

The results are shown in Table 37.

TABLE 37

| Comp. No. | Mortality (%) | Damage |
|---|---|---|
| 1-2 | 100 | 0 |
| 1-5 | 100 | 0 |
| 1-7 | 100 | 0 |
| 1-26 | 100 | 0 |
| 2-5 | 100 | 0 |
| 2-8 | 100 | 0 |
| 3-5 | 100 | 0 |
| 4-4 | 100 | 0 |
| 4-5 | 100 | 0 |
| 4-6 | 100 | 0 |
| 5-5 | 100 | 0 |
| 6-5 | 100 | 0 |
| 7-4 | 100 | 0 |
| 7-5 | 100 | 0 |
| 7-6 | 100 | 0 |
| 8-4 | 100 | 0 |
| 8-5 | 100 | 0 |
| 8-6 | 100 | 0 |
| 9-5 | 100 | 0 |
| 10-5 | 100 | 0 |
| 11-5 | 100 | 0 |
| 11-26 | 100 | 0 |
| 12-5 | 100 | 0 |
| 13-5 | 100 | 0 |
| 14-5 | 100 | 0 |
| 15-5 | 100 | 0 |
| 16-5 | 100 | 0 |
| 17-26 | 100 | 0 |
| 18-5 | 100 | 0 |
| 20-2 | 100 | 0 |
| 20-4 | 100 | 0 |
| 20-5 | 100 | 0 |
| 20-6 | 100 | 0 |
| 20-7 | 100 | 0 |
| 20-10 | 100 | 0 |
| 20-11 | 100 | 0 |
| 20-12 | 100 | 0 |
| 20-13 | 100 | 0 |
| 20-14 | 100 | 0 |
| 20-15 | 100 | 0 |
| 20-25 | 100 | 0 |
| 20-26 | 100 | 0 |
| 20-27 | 100 | 0 |
| 21-4 | 100 | 0 |
| 21-5 | 100 | 0 |
| 21-6 | 100 | 0 |
| 21-7 | 100 | 0 |
| 21-8 | 100 | 0 |
| 21-9 | 100 | 0 |
| 21-10 | 100 | 0 |
| 21-11 | 100 | 0 |
| 21-12 | 100 | 0 |
| 21-13 | 100 | 0 |
| 21-14 | 100 | 0 |
| 21-15 | 100 | 0 |
| 21-25 | 100 | 0 |
| 21-26 | 100 | 0 |
| 21-27 | 100 | 0 |
| 22-4 | 100 | 0 |
| 22-5 | 100 | 0 |
| 22-6 | 100 | 0 |
| 22-10 | 100 | 0 |
| 22-11 | 100 | 0 |
| 22-12 | 100 | 0 |
| 22-13 | 100 | 0 |
| 22-14 | 100 | 0 |
| 22-15 | 100 | 0 |
| 22-26 | 100 | 0 |
| 22-27 | 100 | 0 |
| 23-27 | 100 | 0 |
| 24-5 | 100 | 0 |
| 24-27 | 100 | 0 |
| 26-26 | 100 | 0 |
| 27-2 | 100 | 0 |
| 27-4 | 100 | 0 |

TABLE 37-continued

| Comp. No. | Mortality (%) | Damage |
|---|---|---|
| 27-5 | 100 | 0 |
| 27-6 | 100 | 0 |
| 27-8 | 100 | 0 |
| 27-11 | 100 | 0 |
| 27-16 | 100 | 0 |
| 27-17 | 100 | 0 |
| 27-18 | 100 | 0 |
| 27-20 | 100 | 0 |
| 27-23 | 100 | 0 |
| 27-26 | 100 | 0 |
| 28-8 | 100 | 0 |
| 28-11 | 100 | 0 |
| 28-14 | 100 | 0 |
| 28-17 | 100 | 0 |
| 28-20 | 100 | 0 |
| 28-23 | 100 | 0 |
| 28-26 | 100 | 0 |
| 29-2 | 100 | 0 |
| 29-5 | 100 | 0 |
| 29-8 | 100 | 0 |
| 29-11 | 100 | 0 |
| 29-14 | 100 | 0 |
| 29-17 | 100 | 0 |
| 29-20 | 100 | 0 |
| 29-23 | 100 | 0 |
| 29-26 | 100 | 0 |
| 30-2 | 100 | 0 |
| 30-5 | 100 | 0 |
| 30-8 | 100 | 0 |
| 30-11 | 100 | 0 |
| 30-14 | 100 | 0 |
| 30-17 | 100 | 0 |
| 30-20 | 100 | 0 |
| 30-23 | 100 | 0 |
| 30-26 | 100 | 0 |
| 31-2 | 100 | 0 |
| 31-10 | 100 | 0 |
| 31-11 | 100 | 0 |
| 31-12 | 100 | 0 |
| 31-13 | 100 | 0 |
| 31-14 | 100 | 0 |
| 31-15 | 100 | 0 |
| 31-16 | 100 | 0 |
| 31-17 | 100 | 0 |
| 31-18 | 100 | 0 |
| 31-19 | 100 | 0 |
| 32-2 | 100 | 0 |
| 32-5 | 100 | 0 |
| 32-8 | 100 | 0 |
| 32-11 | 100 | 0 |
| 32-14 | 100 | 0 |
| 32-17 | 100 | 0 |
| 32-20 | 100 | 0 |
| 32-23 | 100 | 0 |
| 32-26 | 100 | 0 |
| 33-2 | 100 | 0 |
| 33-5 | 100 | 0 |
| 33-8 | 100 | 0 |
| 33-11 | 100 | 0 |
| 33-14 | 100 | 0 |
| 33-17 | 100 | 0 |
| 33-20 | 100 | 0 |
| 33-24 | 100 | 0 |
| 34-2 | 100 | 0 |
| 34-5 | 100 | 0 |
| 34-8 | 100 | 0 |
| 34-10 | 100 | 0 |
| 34-11 | 100 | 0 |
| 34-12 | 100 | 0 |
| 35-1 | 100 | 0 |
| 35-2 | 100 | 0 |
| 35-3 | 100 | 0 |

From Table 37, it is shown that the compounds [I] of the present invention have excellent insecticidal activities and are excellent compounds having no damage.

[Industrial Applicability]

The compounds [I] (Oxadiazoline derivatives) or their salts of the present invention have excellent insecticidal activities and less toxicity against fishes. Therefore, the agrochemical compositions (insecticidal compositions) containing the compound [I] or a salt thereof of the present invention can protect crops, etc. from harmful pests and can contribute to an agricultural success.

What is claimed is:

1. A compound represented by the formula [I]:

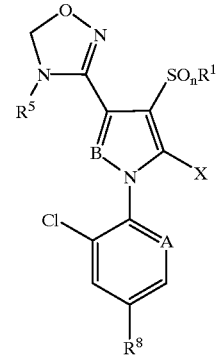

wherein $R^1$ is a $C_{1-6}$ alkyl group or a $C_{1-6}$ haloalkyl group;
n is 0, 1 or 2;
X is (1) a group of $-NR^2R^3$ wherein $R^2$ and $R^3$ independently represent (i) a hydrogen atom or (ii) a $C_{1-6}$ alkyl group which may optionally be substituted with pyridyl group,
(2) a group of $-N=CHOR^4$ wherein $R^4$ represents a $C_{1-6}$ alkyl group,
(3) a group of $-N=CHNR^6R^7$ wherein $R^6$ and $R^7$ independently represent (i) a hydrogen atom or (ii) a $C_{1-6}$ alkyl group,
(4) a group of $-N=CHAr$ wherein Ar represents a phenyl group which may optionally be substituted with a substituent or substituents selected from the group consisting of hydroxy and $C_{1-3}$ alkoxy groups, or
(5) a pyrrolyl group;
$R^5$ is an optionally substituted alkyl group or an optionally substituted acyl group;
$R^8$ is (1) a halogen atom, (2) a $C_{1-6}$ haloalkyl group, (3) a $C_{1-6}$ haloalkoxy group or (4) phenyl which may optionally be substituted with a $C_{1-6}$ haloalkyl group;
A is (1) a nitrogen atom or (2) a group of

wherein $R_9$ is a chlorine atom or cyano; and
B is a nitrogen atom or

or a salt thereof.

2. The compound as claimed in claim 1 wherein $R^1$ is a trifluoromethyl group, or a salt thereof.

3. The compound as claimed in claim 1 wherein X is (1) a group of —NR²R₃ wherein R² and R³ independently represent (i) a hydrogen atom or (ii) a C₁alkyl group, or (2) a group of —N═CHOR⁴ wherein R⁴ represents a C₁₋₆ alkyl group, or a salt thereof.

4. The compound as claimed in claim 1 wherein X is —NH₂ or a group of —N═CHOR⁴ wherein R⁴ represents a C₁₋₆ alkyl group, or a salt thereof.

5. The compound as claimed in claim 1 wherein R⁵ is an optionally substituted carbamoyl group, or a salt thereof.

6. The compound as claimed in claim 1 wherein R⁵ is (1) a C₁₋₆alkyl group which may optionally be substituted with one to three C₁₋₆ alkoxy groups, (2) a C₂₋₁₀ alkanoyl group which may optionally be substituted with one to three substituents selected from the group consisting of (i) amino which may optionally be substituted with one or two C₁₋₆ alkyl groups, (ii) a C₁₋₄ alkoxy group, (iii) phenyl and (iv) a halogen atom, (3) a C₄₋₁₀ cycloalkanoyl group, (4) a C₃₋₁₀ alkenylcarbonyl group, (5) benzoyl, (6) carbamoyl which may optionally be substituted with one or two substituents selected from the group consisting of (i) a C₁₋₆ alkyl group which may optionally be substituted with the substituents selected from the group consisting of phenyl, halogen and amino which may optionally be substituted with C₁₋₆ alkyl, (ii) a C₃₋₉ cycloalkyl group, (iii) a C₂₋₆ alkenyl group, (iv) a C₂₋₆ alkynyl group, (v) phenyl, (vi) amino which may optionally be substituted with one or two C₁₋₆ alkyl groups, (vii) a cyclic amino group, (viii) hydroxy and (ix) a C₁₋₆ alkoxy group, (7) a cyclic amino-carbonyl group, or (8) a C₁₋₆ alkoxy-carbonyl group or (9) formyl, or a salt thereof.

7. The compound as claimed in claim 1 wherein R⁸ is a trifluoromethyl group, or a salt thereof.

8. The compound as claimed in claim 1 wherein A is

or a salt thereof.

9. The compound as claimed in claim 1 wherein B is a nitrogen atom, or a salt thereof.

10. The compound as claimed in claim 1 wherein X is (1) a group of —NR²R³ wherein R² and R³ independently represent (i) a hydrogen atom or (ii) a C₁₋₆ alkyl group,
  (2) a group of —N═CHOR⁴ wherein R⁴represents a C₁₋₆ alkyl group, or
  (3) a group of —N═CHNR⁶R⁷ wherein R⁶ and R⁷ independently represent (i) a hydrogen atom or (ii) a C₁₋₆ alkyl group;
R⁸ is trifluoromethyl;
A is

and

B is a nitrogen atom, or a salt thereof.

11. The compound as claimed in claim 10 wherein X is (1) a group of —NR²R³ wherein R² and R³ independently represent (i) a hydrogen atom or (ii) a C₁₋₆ alkyl group, or (2) a group of —N═CHOR⁴wherein R⁴represents a C₁₋₆ alkyl group, or a salt thereof.

12. The compound as claimed in claim 1 which is 1-(2,6-dichloro-4-trifluoromethylphenyl)-3-{4-(N,N-dimethylcarbamoyl)-Δ²-1,2,4-oxadiazolin-3-yl}-5-isopropoxymethyleneamino-4-trifluoromethylsulfinylpyrazole or a salt thereof.

13. The compound as claimed in claim 1 which is 1-(2,6-dichloro-4-trifluoromethylphenyl)-3-{4-(N,N-dimethylcarbamoyl)-Δ²-1,2,4-oxadiazolin-3-yl}-5-ethoxymethyleneamino-4-trifluoromethylsulfinylpyrazole or a salt thereof.

14. The compound as claimed in claim 1 which is 1-(2,6-dichloro-4-trifluoromethylphenyl)-5-ethoxymethyleneamino-3-{4-(morpholinocarbonyl)-Δ²-1,2,4-oxadiazolin-3-yl}-4-trifluoromethylsulfinylpyrazole or a salt thereof.

15. The compound as claimed in claim 1 which is 1-(2,6-dichloro-4-trifluoromethylphenyl)-5-ethoxymethyleneamino-3-{4-isobutylyl-Δ²-1,2,4-oxadiazolin-3-yl}-4-trifluoromethylsulfinylpyrazole or a salt thereof.

16. An agrochemical composition which comprises an effective amount of the compound as claimed in claim 1 or a salt thereof together with a carrier.

17. The agrochemical composition as claimed in claim 16 which is an insecticidal composition.

18. A method of combatting an insect, which comprises applying or administering an effective dose of the compound as claimed in claim 1 or a salt thereof to a vertebrate, a paddy field, plowland, orchard, non-cropland or house.

19. A method of making an agrochemical composition, which comprises mixing the compound as claimed in claim 1 or a salt thereof with a carrier.

* * * * *

UNITED STATES PATENT AND TRADEMARK OFFICE
CERTIFICATE OF CORRECTION

PATENT NO. : 6,288,088 B1  
DATED : September 11, 2001  
INVENTOR(S) : Yasuyuki Kando et al.

Page 1 of 1

It is certified that error appears in the above-identified patent and that said Letters Patent is hereby corrected as shown below:

<u>Title page,</u>  
Item [75], Inventors, the name of the second inventor "Makota Noguchi" should read as -- Makoto Noguchi --.

Signed and Sealed this

Second Day of April, 2002

*Attest:*

JAMES E. ROGAN  
*Attesting Officer*     *Director of the United States Patent and Trademark Office*